(12) United States Patent
Akama et al.

(10) Patent No.: US 9,493,490 B1
(45) Date of Patent: Nov. 15, 2016

(54) BORON-CONTAINING SMALL MOLECULES

(71) Applicant: Anacor Pharmaceuticals, Inc., Palo Alto, CA (US)

(72) Inventors: Tsutomu Akama, Sunnyvale, CA (US); Kurt Jarnagin, San Mateo, CA (US); Yong-Kang Zhang, San Jose, CA (US); Yasheen Zhou, Moraga, CA (US); Jacob J. Plattner, Berkeley, CA (US); David C. Sullivan, Mountain View, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 14/906,849

(22) PCT Filed: Jul. 22, 2014

(86) PCT No.: PCT/US2014/047675
§ 371 (c)(1),
(2) Date: Jan. 21, 2016

(87) PCT Pub. No.: WO2015/013318
PCT Pub. Date: Jan. 29, 2015

Related U.S. Application Data

(60) Provisional application No. 61/857,049, filed on Jul. 22, 2013.

(51) Int. Cl.
| | |
|---|---|
| *C07F 5/02* | (2006.01) |
| *A61K 31/69* | (2006.01) |
| *A61K 45/06* | (2006.01) |

(52) U.S. Cl.
CPC ............... *C07F 5/025* (2013.01); *A61K 31/69* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2010/0256092 A1 | 10/2010 | Xia et al. | |
| 2011/0166104 A1 | 7/2011 | Zhou et al. | |

FOREIGN PATENT DOCUMENTS

| | | | |
|---|---|---|---|
| WO | 2010028005 | * | 3/2010 |
| WO | 2015013318 | * | 1/2015 |

OTHER PUBLICATIONS

Akama et al., Journal of Pharmacology and Experimental Therapeutics (2013), 347(3), 615-625.*
Inoue et al., Progress in Retinal and Eye Research 37 (2013) 1-12.*
U.S. Appl. No. 13/861,846, filed Apr. 12, 2013, now abandoned.
U.S. Appl. No. 13/673,860, filed Nov. 9, 2012, now abandoned.
U.S. Appl. No. 13/607,321, filed Sep. 7, 2012, now abandoned.
U.S. Appl. No. 13/607,405, filed Sep. 7, 2012, now abandoned.
U.S. Appl. No. 13/607,250, filed Sep. 7, 2012, now abandoned.
U.S. Appl. No. 15/134,286, filed Apr. 20, 2016.
U.S. Appl. No. 15/091,394, filed Apr. 5, 2016.
U.S. Appl. No. 15/068,352, filed Mar. 11, 2016.
U.S. Appl. No. 15/046,322, filed Feb. 17, 2016.
U.S. Appl. No. 14/977,052, filed Dec. 21, 2015.
U.S. Appl. No. 14/537,771, filed Nov. 10, 2014.
U.S. Appl. No. 14/537,694, filed Nov. 10, 2014, now abandoned.
U.S. Appl. No. 14/201,459, filed Mar. 7, 2014, now U.S. Pat. No. 9,353,133.
U.S. Appl. No. 14/165,428, filed Mar. 7, 2014, now abandoned.
U.S. Appl. No. 13/874,329, filed Apr. 30, 2013, now U.S. Pat. No. 8,889,656.
U.S. Appl. No. 13/224,252, filed Sep. 1, 2011, now U.S. Pat. No. 8,440,642.
U.S. Appl. No. 13/356,488, filed Jan. 23, 2012, now U.S. Pat. No. 8,722,917.
U.S. Appl. No. 12/629,753, filed Dec. 2, 2009, now U.S. Pat. No. 8,115,026.
U.S. Appl. No. 11/357,687, filed Feb. 16, 2006, now U.S. Pat. No. 7,582,621.
U.S. Appl. No. 11/505,591, filed Aug. 16, 2006, now U.S. Pat. No. 7,767,657.
U.S. Appl. No. 12/507,010, filed Jul. 21, 2009, now U.S. Pat. No. 8,039,451.
U.S. Appl. No. 11/676,120, filed Feb. 16, 2007, now U.S. Pat. No. 8,168,641.
U.S. Appl. No. 13/453,682, filed Apr. 23, 2012, now U.S. Pat. No. 8,501,712.
U.S. Appl. No. 13/954,770, filed Jul. 30, 2013, now U.S. Pat. No. 9,029,353.
U.S. Appl. No. 14/688,581, filed Apr. 16, 2015.
U.S. Appl. No. 11/762,038, filed Jun. 12, 2007, now abandoned.
U.S. Appl. No. 11/865,725, filed Oct. 1, 2007, now abandoned.
U.S. Appl. No. 12/142,692, filed Jun. 19, 2008, now U.S. Pat. No. 7,816,344.
U.S. Appl. No. 12/752,789, filed Apr. 1, 2010, now abandoned.
U.S. Appl. No. 12/848,051, filed Jul. 30, 2010, now U.S. Pat. No. 8,895,534.
U.S. Appl. No. 12/399,015, filed Mar. 5, 2009, now U.S. Pat. No. 8,039,450.
U.S. Appl. No. 13/236,543, filed Sep. 19, 2011, now U.S. Pat. No. 8,461,135.
U.S. Appl. No. 14/536,483, filed Nov. 7, 2014.
U.S. Appl. No. 13/915,494, filed Jun. 11, 2013, now U.S. Pat. No. 9,012,431.

(Continued)

*Primary Examiner* — Karl J Puttlitz
(74) *Attorney, Agent, or Firm* — Morgan, Lewis & Bockius LLP

(57) ABSTRACT

This invention provides novel compounds of the following formula and pharmaceutical compositions containing such compounds.

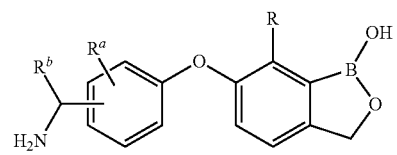

19 Claims, No Drawings

(56) References Cited

OTHER PUBLICATIONS

U.S. Appl. No. 14/666,075, filed Mar. 23, 2015.
U.S. Appl. No. 13/062,450, filed Mar. 4, 2011.
U.S. Appl. No. 12/464,829, filed May 12, 2009, now abandoned.
U.S. Appl. No. 13/062,466, filed Mar. 4, 2011, now U.S. Pat. No. 8,470,803.
U.S. Appl. No. 12/641,318, filed Dec. 17, 2009, now U.S. Pat. No. 8,461,364.
U.S. Appl. No. 12/873,036, filed Aug. 31, 2010, now abandoned.
U.S. Appl. No. 12/844,748, filed Jul. 27, 2010, now U.S. Pat. No. 8,343,944.
U.S. Appl. No. 13/062,491, filed Mar. 4, 2011, now U.S. Pat. No. 8,461,336.
U.S. Appl. No. 13/503,016, filed Jun. 25, 2012, now allowed.
U.S. Appl. No. 12/857,305, filed Aug. 16, 2010, now abandoned.
U.S. Appl. No. 12/852,351, filed Aug. 6, 2010.
U.S. Appl. No. 12/944,690, filed Nov. 11, 2010, now U.S. Pat. No. 8,461,134.
U.S. Appl. No. 13/015,487, filed Jan. 27, 2011, now U.S. Pat. No. 8,716,478.
U.S. Appl. No. 14/133,537, filed Dec. 18, 2013, now U.S. Pat. No. 9,145,429.
U.S. Appl. No. 14/852,122, filed Sep. 11, 2015.
U.S. Appl. No. 12/944,699, filed Nov. 11, 2010, now abandoned.
U.S. Appl. No. 13/639,594, filed Sep. 7, 2012, now U.S. Pat. No. 9,243,003.
U.S. Appl. No. 14/969,467, filed Dec. 15, 2015.
U.S. Appl. No. 13/227,444, filed Sep. 7, 2011, now U.S. Pat. No. 8,703,742.
U.S. Appl. No. 14/221,637, filed Mar. 21, 2014.
U.S. Appl. No. 13/678,576, filed Nov. 16, 2012, now U.S. Pat. No. 8,853,186.
U.S. Appl. No. 14/507,453, filed Oct. 14, 2014, now U.S. Pat. No. 9,156,860.
U.S. Appl. No. 14/852,220, filed Sep. 11, 2015.
U.S. Appl. No. 13/678,578, filed Nov. 16, 2012, now U.S. Pat. No. 8,546,357.
U.S. Appl. No. 14/760,208, filed Jul. 10, 2015.
U.S. Appl. No. 14/394,427, filed Oct. 14, 2014.
U.S. Appl. No. 14/765,152, filed Jul. 31, 2015; and.
U.S. Appl. No. 14/910,996, filed Feb. 8, 2016.
Tsutomu Akama, et al. "Structure-activity relationships of 6-(aminomethylphenoxy)benzoxaborole derivatives as anti-inflammatory agent", Bioorganic & Medicianl Chemistry Letters, vol. 23, No. 6, Mar. 1, 2013, pp. 1680-1683.
Yi Xia, et al. "Synthesis and SAR of novel benzoxaboroles as a new class of p-lactamase inhibitors", Bioorganic & Medicianl Chemistry Letters, vol. 21, No. 8, Apr. 1, 2013, pp. 2533-2536.

* cited by examiner

BORON-CONTAINING SMALL MOLECULES

CROSS-REFERENCE TO RELATED APPLICATIONS

This application is a National Stage of International Patent Application No. PCT/US2014/047675 filed Jul. 22, 2014 and published as WO 2015/013318 A1, which claims priority to U.S. Provisional Application No. 61/857,049 filed Jul. 22, 2013, the entire contents of which applications is incorporated herein for all purposes by this reference.

BACKGROUND FOR THE INVENTION

ROCK kinase was first characterized in 1996 by Matsui et al. as a Rho regulated kinase from the AGC subfamily of Ser/Thr kinases. [Matsui T, et al. *EMBO J*. 1996 May 1; 15(9):2208-16; Pearce L R, et al. *Nat Rev Mol Cell Biol*. 2010 January; 11(1):9-22; Olson M F, *Curr Opin Cell Biol*. 2008 April; 20(2):242-8]. Two genes encode the highly related enzymes ROCK1 and ROCK2, which are both widely distributed in many tissues [Mueller B K, *Nat Rev Drug Discov*. 2005 May; 4(5):387-98. Both contain a N-terminal kinase domain, a coil-coiled domain associated with dimerization, a mid-protein Rho-binding domain (RBD) and C-terminal, membrane association Plextrin homology (PH) domain, and a further C-terminal cysteine rich domain that binds lipid substrates [Pearce L R et al., *Nat Rev Mol Cell Biol*. 2010 January; 11(1):9-22; Mueller B K et al, *Nat Rev Drug Discov*. 2005 May; 4(5):387-98]. Binding of Rho-GTP to the Rho-binding domain releases auto-inhibition and allows the kinase to phosphorylate substrates. At least 11 different substrates have been demonstrated for ROCK kinases many of which are involved in the regulation of myosin-actin skeleton, and cell adhesion and mobility [Pearce L R et al., *Nat Rev Mol Cell Biol*. 2010 January; 11(1):9-22; Haas M A et al., *J Neurosci Res*. 2007 January; 85(1):34-46; Matsui T et al., *J Cell Biol*. 1998 Feb. 9; 140(3):647-57; Ivetic A et al., *Immunology*, 2004 June; 112(2):165-76]. The best characterized substrates are myosin light chain (MLC), and myosin phosphatase-1 (MYPT1) which together activate myosin and increase myosin fiber contraction; these actions lead to the tonic smooth muscle contraction in the vasculature, and lungs [Uehata M, et al., *Nature* 1997 Oct. 30; 389(6654):990-4; Kaneko-Kawano T et al., *PLoS One* 2012; 7(6):e39269].

The first synthetic kinase inhibitor to be approved was a ROCK inhibitor, Fasudil approved in 1995 for cerebral venospasm secondary to aneurysm, (Ono-Saito N, et al., *Pharmacol Ther*. 1999 May-June; 82(2-3):123-31). This compound was discovered while examining calmodulin inhibitors of the naphthalene-sulfonamide family, and noting a group that inhibited AGC family kinases; subsequently, ROCK was identified as the highest affinity target (Takayasu M, et al., *J Neurosurg*. 1986 July; 65(1):80-5; Ono-Saito N et al., *Pharmacol Ther*. 1999 May-June; 82(2-3):123-31; Uehata M et al., *Nature* 1997 Oct. 30; 389(6654):990-4). Other clinical studies have also shown that Fasudil leads to beneficial outcomes in angina (Shimokawa H et al., *J Cardiovasc Pharmacol*. 2002 November; 40(5):751-61), and pulmonary hypertension (Fukumoto Y et al., *Heart* 2005 March; 91(3):391-2; Fukumoto Y et al., *Tohoku J Exp Med*. 2007 April; 211(4):309-20). Trials for use of ROCK kinase inhibitors in glaucoma have been initiated with five different compounds (Chen J et al., *Clin Ophthalmol*. 2011; 5:667-77); however, early studies have shown that adequate pressure lowering and hyperemia—redness—might limit application (Williams R D, et al., *Am J Ophthalmol*. 2011 November; 152(5):834-41; Tanihara H, et al., *Arch Ophthalmol*. 2008 March; 126(3):309-15).

Human tissue and animal studies have shown that ROCK inhibitors have a role in wound healing (Bond J E et al., *Plast Reconstr Surg*. 2011 November; 128(5):438e-450e); treatment of spinal cord injury (Impellizzeri D et al., *J Pharmacol Exp Ther*. 2012 October; 343(1):21-33); and treatment of neuropathic pain (reviewed in Mueller B K et al., *Nat Rev Drug Discov*. 2005 May; 4(5):387-98). Human-genome-wide association studies connected the ROCK pathway with memory defects and Alzheimer's disease (Huentelman M J et al., *Behav Neurosci*. 2009 February; 123(1):218-23) which led to successful tests showing ROCK inhibitors improve memory in aged rats. Cardiac hypertrophy, and fibrosis in mice and rats are reduced by ROCK inhibitors, by a mechanism that may involve the ROCK mediated phosphorylation of PTEN-phosphatase and subsequent activation of the Akt pathway (reviewed in McKinsey T A et al., *Nat Rev Drug Discov*. 2007 August; 6(8):617-35). Together these findings indicate that ROCK inhibitors may find application in several important therapeutic areas.

Inflammation is strongly affected by ROCK inhibitors since cytoskeletal reorganization is important for the formation of the immune synapse and for chemotaxis (Takesono A. et al., *PLoS One* 2010 Jan. 19; 5(1):e8774; Hogg N et al., *J Cell Sci*. 2003 Dec. 1; 116(Pt 23):4695-705) Indeed, the beneficial effects of Fasudil on cerebral venospasm are associated with a reduction in the number of neutrophils at lesion sites (Satoh S et al., *Jpn J Pharmacol*. 1999 May; 80(1):41-8.). Inflammation suppression maybe part of the mechanism behind the beneficial effects of ROCK inhibitors on spinal cord injury (Impellizzeri D et al., *J Pharmacol Exp Ther*. 2012 October; 343(1):21-33) and arthritis (He Y et al., *Arthritis Rheum*. 2008 November; 58(11):3366-76). Given the effects on smooth muscle contraction and inflammation, which are the outcomes and the cause of asthma, respectively, asthma is an obvious application for ROCK inhibitors. In mice, guinea pigs and in human tissues, inhaled and systemic administration of ROCK inhibitors block eosinophilia, airway contraction and hyper-responsiveness, endpoints associated with asthma suppression. (Schaafsma D. et al., *Respir Res*. 2006 Sep. 26; 7:121; Kume H. et al., *Curr Med Chem*. 2008; 15(27):2876-85; Henry P J et al., *Pulm Pharmacol Ther*. 2005; 18(1):67-74; Hashimoto K et al., *Thorax*. 2002 June; 57(6):524-7; Schaafsma D et al., *Eur J Pharmacol*. 2006 Feb. 15; 531(1-3):145 50; Schaafsma D et al., *Am J Physiol Lung Cell Mol Physiol*. 2008 July; 295 (1):L214-9; Schaafsma D et al., *Eur J Pharmacol*. 2008 May 13; 585(2-3):398-406; Iizuka K et al., *Eur J Pharmacol*. 2000 Oct. 13; 406(2):273-9; Yoshii A, *Am J Respir Cell Mol Biol*. 1999 June; 20(6):1190-200)

Compounds which can inhibit the biological moieties described above, or treat diseases involving those biological moieties, would be a significant advance in the art.

SUMMARY OF THE INVENTION

In a first aspect, the invention provides a compound of the invention which is described herein.

The invention also provides pharmaceutical formulations, and methods of making and using the compounds described herein.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino) pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2(pddf)$ is 1,1'-Bis(diphenylphosphino) ferrocene]dichloropalladium(II); Pd/C is the catalyst known as palladium on carbon; $Pd_2(dba)_3$ is an organometallic catalyst known as tris(dibenzylideneacetone) dipalladium(0); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr. or Pyr or Py as used herein means pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TFA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride; 3-F-4-$NO_2$-$PhSO_2Cl$ is 3-fluoro-4-nitrophenylsulfonyl chloride; 2-MeO-4-$NO_2$-$PhSO_2Cl$ is 2-methoxy-4-nitrophenylsulfonyl chloride; and $(EtO)_2POCH_2COOEt$ is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

The term "poly" as used herein means at least 2. For example, a polyvalent metal ion is a metal ion having a valency of at least 2.

"Moiety" refers to a radical of a molecule that is attached to the remainder of the molecule.

The symbol ⌇, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —$CH_2CH_2CH_2CH_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkyl.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined herein. Thus, the term "arylalkyl" is meant to include those radicals in which an aryl group is attached to an alkyl group (e.g., benzyl, phenethyl, pyridiylethyl and the like) including those alkyl groups in which a carbon atom (e.g. a methylene group) has been replaced by, for example, an oxygen atom (e.g., phenoxymethyl, 2-pyridyloxymethyl, 3-(1-naphthyloxy)propyl, and the like).

For brevity, the term "heteroaryl" when used in combination with other terms (e.g., heteroaryloxy, heteroarylthioxy, heteroarylalkyl) includes those radicals in which a heteroaryl group is attached through the next moiety to the rest of the molecule. Thus, the term "heteroarylalkyl" is meant to include those radicals in which a heteroaryl group is attached to an alkyl group (e.g., pyridylmethyl and the like). The term "heteroaryloxy" is meant to include those radicals in which a heteroaryl group is attached to an oxygen atom. The term "heteroaryloxyalkyl" is meant to include those radicals in which an aryl group is attached to an oxygen atom which is then attached to an alkyl group. (e.g., 2-pyridyloxymethyl and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to (2m'+1), where m' is the total number of carbon atoms in such radical. R', R", R'", R"" and R""' each preferably independently refer to hydrogen, substituted or unsubstituted heteroalkyl, substituted or unsubstituted aryl, e.g., aryl substituted with 1 or 2 or 3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR''''—C(NR'R"R''')=NR'''', —NR''''—C(NR'R")=NR''', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', R'''' and R''''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''', R'''' and R''''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer from 0 or 1 or 2 or 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer from 1 or 2 or 3 or 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers from 0 or 1 or 2 or 3, and X is –O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$ or C$_2$ or C$_3$ or C$_4$ or C$_5$ or C$_6$)alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), and boron (B).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "pharmaceutically effective," or "therapeutically effective" amount refers to the amount of drug needed to effect the desired therapeutic result.

The term "pharmaceutically acceptable salt" is meant to include a salt of a compound of the invention which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, or l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, *J. Chem. Ed.* 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

The term "excipients" is conventionally known to mean carriers, diluents and/or vehicles used in formulating drug compositions effective for the desired use.

The term "microbial infection" or "infection by a microorganism" refers to any infection of a host tissue by an infectious agent including, but not limited to, bacteria or protozoa (see, e.g., Harrison's Principles of Internal Medicine, pp. 93-98 (Wilson et al., eds., 12th ed. 1991); Williams et al., J. of Medicinal Chem. 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of a domain of a protein. In an exemplary embodiment, the domain is the A site of a 50S subunit of a ribosome.

Boron is able to form additional covalent or dative bonds with oxygen, sulfur or nitrogen under some circumstances in this invention.

Embodiments of the invention also encompass compounds that are poly- or multi-valent species, including, for example, species such as dimers, trimers, tetramers and higher homologs of the compounds of use in the invention or reactive analogues thereof.

"Salt counterion", as used herein, refers to positively charged ions that associate with a compound of the invention when the boron is fully negatively or partially negatively charged. Examples of salt counterions include H$^+$, H$_3$O$^+$, ammonium, potassium, calcium, magnesium, organic amino (such as choline or diethylamine or amino acids such as d-arginine, l-arginine, d-lysine, or l-lysine) and sodium.

The compounds comprising a boron bonded to a carbon and three heteroatoms (such as three oxygens described in this section) can optionally contain a fully negatively charged boron or partially negatively charged boron. Due to the negative charge, a positively charged counterion may associate with this compound, thus forming a salt. Examples of positively charged counterions include H$^+$, H$_3$O$^+$, ammonium, potassium, calcium, magnesium, organic amino (such as choline or diethylamine or amino acids such as d-arginine, l-arginine, d-lysine, l-lysine), and sodium. These salts of the compounds are implicitly contained in descriptions of these compounds.

II. Introduction

The present invention has multiple aspects. These aspects include inventions directed to compounds, pharmaceutical formulations, methods of treating a condition, enhancing an effect, increasing the production of a cytokine and/or chemokine, decreasing the production of a cytokine and/or chemokine, increasing the release of a cytokine and/or chemokine, decreasing the release of a cytokine and/or chemokine, or inhibiting a phosphodiesterase.

III. Compounds

IIIa.

In a first aspect, the invention provides a compound of the invention. In an exemplary embodiment, the invention provides a compound described herein. In an exemplary embodiment, the invention provides a compound of the invention which is described in an example provided herein. In an exemplary embodiment, the compound is a member selected from A, B, C, D, E, F, and G. In an exemplary embodiment, the compound is a member selected from L, M, and N.

In an exemplary embodiment, the compound, or a salt thereof, has a structure which is

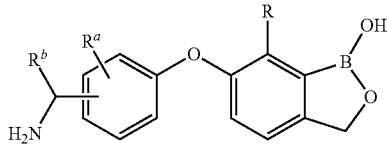

wherein $R^a$ is halogen, $R^b$ is H or unsubstituted $C_1$-$C_4$ alkyl, when $R^b$ is unsubstituted $C_1$-$C_4$ alkyl, then R is H or halogen or unsubstituted $C_1$-$C_4$ alkyl, when $R^b$ is H, then R is halogen or unsubstituted $C_1$-$C_4$ alkyl.

In an exemplary embodiment, the compound, or a salt thereof, has a structure which is

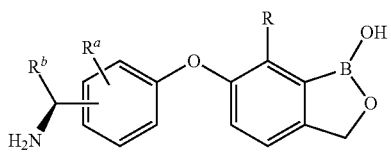

wherein $R^a$ is halogen, $R^b$ is H or unsubstituted $C_1$-$C_4$ alkyl, when $R^b$ is unsubstituted $C_1$-$C_4$ alkyl, then R is H or halogen or unsubstituted $C_1$-$C_4$ alkyl, when $R^b$ is H, then R is halogen or unsubstituted $C_1$-$C_4$ alkyl.

In an exemplary embodiment, the compound, or a salt thereof, has a structure which is

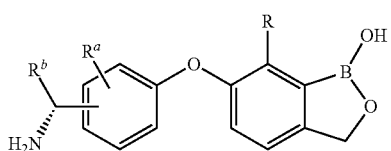

wherein $R^a$ is halogen, $R^b$ is H or unsubstituted $C_1$-$C_4$ alkyl, when $R^b$ is unsubstituted $C_1$-$C_4$ alkyl, then R is H or halogen or unsubstituted $C_1$-$C_4$ alkyl, when $R^b$ is H, then R is halogen or unsubstituted $C_1$-$C_4$ alkyl.

In an exemplary embodiment, the compound, or a salt thereof, has a structure which is

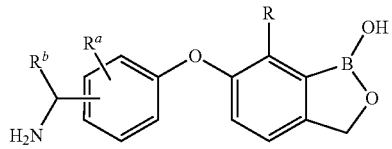

wherein $R^a$ is halogen, $R^b$ is unsubstituted $C_1$-$C_4$ alkyl, and R is H or halogen or unsubstituted $C_1$-$C_4$ alkyl.

In an exemplary embodiment, the compound, or a salt thereof, has a structure which is

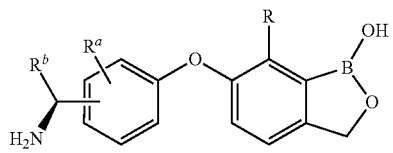

wherein $R^a$ is halogen, $R^b$ is unsubstituted $C_1$-$C_4$ alkyl, and R is H or halogen or unsubstituted $C_1$-$C_4$ alkyl.

In an exemplary embodiment, the compound, or a salt thereof, has a structure which is

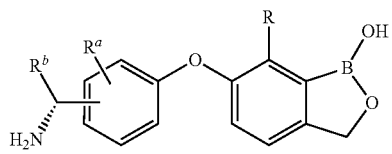

wherein $R^a$ is halogen, $R^b$ is unsubstituted $C_1$-$C_4$ alkyl, and R is H or halogen or unsubstituted $C_1$-$C_4$ alkyl.

In an exemplary embodiment, the compound, or a salt thereof, has a structure which is

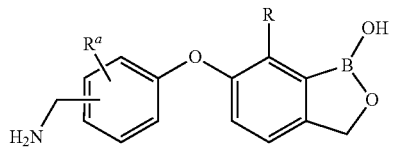

wherein $R^a$ is halogen, and R is halogen or unsubstituted $C_1$-$C_4$ alkyl.

In an exemplary embodiment, the compound, or a salt thereof, has a structure which is

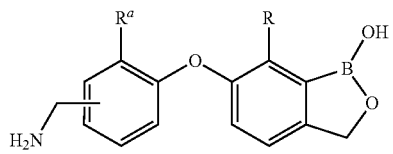

wherein $R^a$ is halogen, and R is halogen or unsubstituted $C_1$-$C_4$ alkyl.

In an exemplary embodiment, the compound, or a salt thereof, has a structure which is

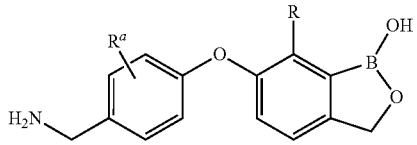

wherein $R^a$ is halogen, and R is halogen or unsubstituted $C_1$-$C_4$ alkyl.

In an exemplary embodiment, the compound, or a salt thereof, has a structure which is

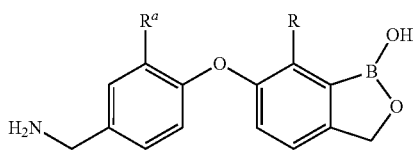

wherein $R^a$ is halogen, and R is halogen or unsubstituted $C_1$-$C_4$ alkyl.

In an exemplary embodiment, the compound, or a salt thereof, has a structure which is

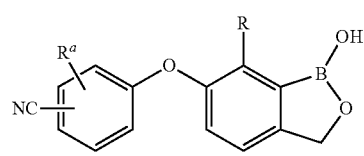

wherein $R^a$ is halogen, and R is halogen or unsubstituted $C_1$-$C_4$ alkyl.

In an exemplary embodiment, the compound, or a salt thereof, has a structure which is

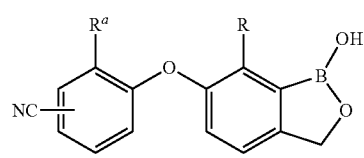

wherein $R^a$ is halogen, and R is halogen or unsubstituted $C_1$-$C_4$ alkyl.

In an exemplary embodiment, the compound, or a salt thereof, has a structure which is

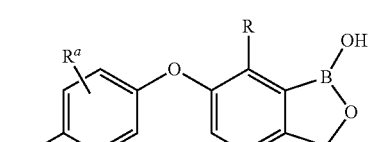

wherein $R^a$ is halogen, and R is halogen or unsubstituted $C_1$-$C_4$ alkyl.

In an exemplary embodiment, the compound, or a salt thereof, has a structure which is

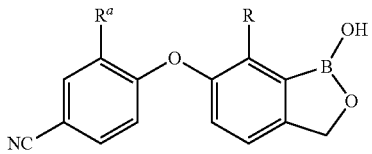

wherein $R^a$ is halogen, and R is halogen or unsubstituted $C_1$-$C_4$ alkyl.

In an exemplary embodiment, the compound, or a salt thereof, has a structure which is

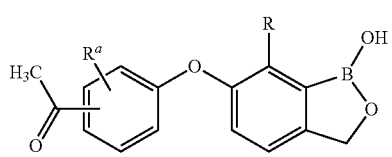

wherein $R^a$ is halogen, and R is halogen or unsubstituted $C_1$-$C_4$ alkyl.

In an exemplary embodiment, the compound, or a salt thereof, has a structure which is

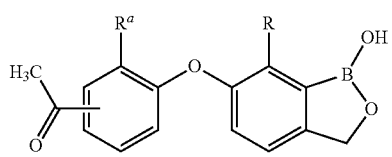

wherein $R^a$ is halogen, and R is halogen or unsubstituted $C_1$-$C_4$ alkyl.

In an exemplary embodiment, the compound, or a salt thereof, has a structure which is

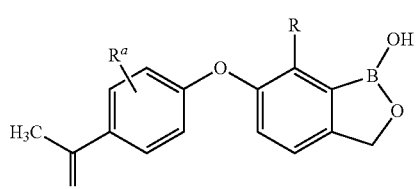

wherein $R^a$ is halogen, and R is halogen or unsubstituted $C_1$-$C_4$ alkyl.

In an exemplary embodiment, the compound, or a salt thereof, has a structure which is

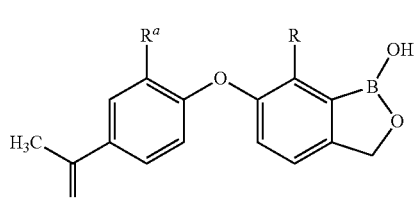

wherein $R^a$ is halogen, and R is halogen or unsubstituted $C_1$-$C_4$ alkyl.

In an exemplary embodiment, the compound, or a salt thereof, has a structure which is

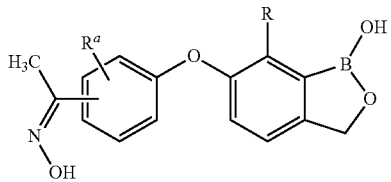

wherein $R^a$ is halogen, and R is halogen or unsubstituted $C_1$-$C_4$ alkyl.

In an exemplary embodiment, the compound, or a salt thereof, has a structure which is

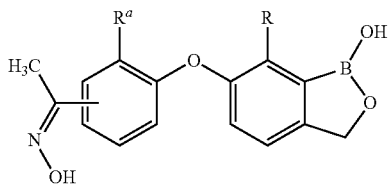

wherein $R^a$ is halogen, and R is halogen or unsubstituted $C_1$-$C_4$ alkyl.

In an exemplary embodiment, the compound, or a salt thereof, has a structure which is

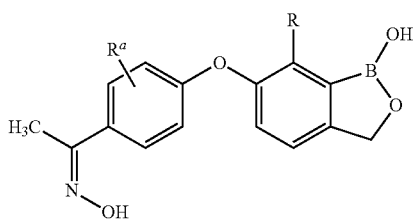

wherein $R^a$ is halogen, and R is halogen or unsubstituted $C_1$-$C_4$ alkyl.

In an exemplary embodiment, the compound, or a salt thereof, has a structure which is

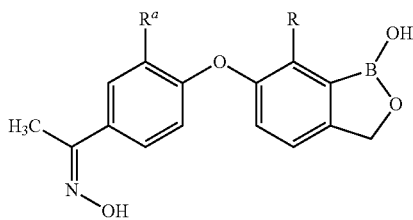

wherein $R^a$ is halogen, and R is halogen or unsubstituted $C_1$-$C_4$ alkyl.

In an exemplary embodiment, the compound, or a salt thereof, has a structure which is

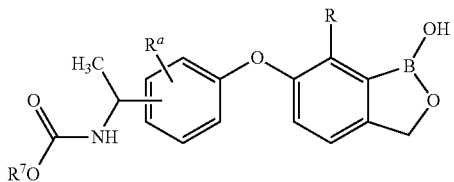

wherein $R^a$ is halogen, R is halogen or unsubstituted $C_1$-$C_4$ alkyl, and $R^7$ is H or unsubstituted $C_1$-$C_6$ alkyl. In an exemplary embodiment, $R^a$ and R are as described herein, and $R^7$ is H. In an exemplary embodiment, $R^a$ and R are as described herein, and $R^7$ is unsubstituted $C_1$-$C_6$ alkyl. In an exemplary embodiment, $R^a$ and R are as described herein, and $R^7$ is t-butyl.

In an exemplary embodiment, the compound, or a salt thereof, has a structure which is

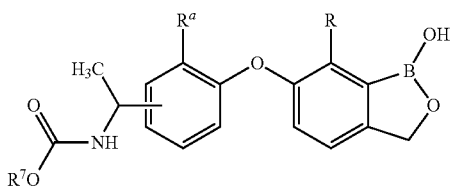

wherein $R^a$ is halogen, R is halogen or unsubstituted $C_1$-$C_4$ alkyl, and $R^7$ is H or unsubstituted $C_1$-$C_6$ alkyl. In an exemplary embodiment, $R^a$ and R are as described herein, and $R^7$ is H. In an exemplary embodiment, $R^a$ and R are as described herein, and $R^7$ is unsubstituted $C_1$-$C_6$ alkyl. In an exemplary embodiment, $R^a$ and R are as described herein, and $R^7$ is t-butyl.

In an exemplary embodiment, the compound, or a salt thereof, has a structure which is

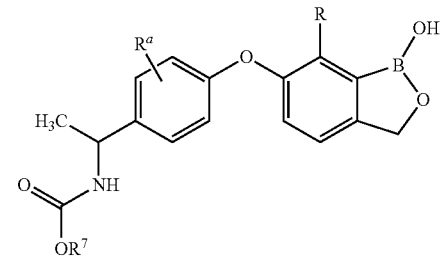

wherein $R^a$ is halogen, R is halogen or unsubstituted $C_1$-$C_4$ alkyl, and $R^7$ is H or unsubstituted $C_1$-$C_6$ alkyl. In an exemplary embodiment, $R^a$ and R are as described herein, and $R^7$ is H. In an exemplary embodiment, $R^a$ and R are as described herein, and $R^7$ is unsubstituted $C_1$-$C_6$ alkyl. In an exemplary embodiment, $R^a$ and R are as described herein, and $R^7$ is t-butyl.

In an exemplary embodiment, the compound, or a salt thereof, has a structure which is

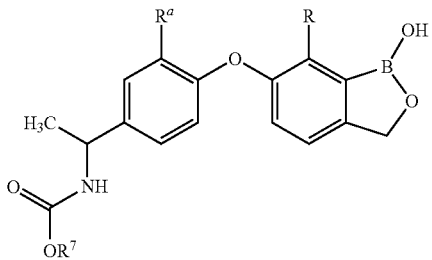

wherein $R^a$ is halogen, R is halogen or unsubstituted $C_1$-$C_4$ alkyl, and $R^7$ is H or unsubstituted $C_1$-$C_6$ alkyl. In an exemplary embodiment, $R^a$ and R are as described herein, and $R^7$ is H. In an exemplary embodiment, $R^a$ and R are as described herein, and $R^7$ is unsubstituted $C_1$-$C_6$ alkyl. In an exemplary embodiment, $R^a$ and R are as described herein, and $R^7$ is t-butyl.

In an exemplary embodiment, the compound, or a salt thereof, has a structure described herein, and $R^b$ and $R^a$ are as described herein, and R is halogen or unsubstituted $C_1$-$C_4$ alkyl, or a salt thereof. In an exemplary embodiment, the compound, or a salt thereof, has a structure described herein, and $R^b$ and $R^a$ are as described herein, and R is Br. In an exemplary embodiment, the compound, or a salt thereof, has a structure described herein, and $R^b$ and $R^a$ are as described herein, and R is Cl. In an exemplary embodiment, the compound, or a salt thereof, has a structure described herein, and $R^b$ and $R^a$ are as described herein, and R is F. In an exemplary embodiment, the compound, or a salt thereof, has a structure described herein, and $R^b$ and $R^a$ are as described herein, and R is unsubstituted $C_1$ or $C_2$ or $C_3$ or $C_4$ alkyl. In an exemplary embodiment, the compound, or a salt thereof, has a structure described herein, and $R^b$ and $R^a$ are as described herein, and R is methyl. In an exemplary embodiment, the compound, or a salt thereof, has a structure described herein, and $R^b$ and $R^a$ are as described herein, and R is ethyl. In an exemplary embodiment, the compound, or a salt thereof, has a structure described herein, and $R^b$ and $R^a$ are as described herein, and R is propyl. In an exemplary embodiment, the compound, or a salt thereof, has a structure described herein, and $R^b$ and $R^a$ are as described herein, and R is isopropyl. In an exemplary embodiment, the compound, or a salt thereof, has a structure described herein, and $R^b$ and $R^a$ are as described herein, and R is butyl. In an exemplary embodiment, the compound, or a salt thereof, has a structure described herein, and $R^b$ and $R^a$ are as described herein, and R is isobutyl.

In an exemplary embodiment, the compound, or a salt thereof, has a structure described herein, and $R^b$ is as described herein, and R is halogen or unsubstituted $C_1$-$C_4$ alkyl, or a salt thereof. In an exemplary embodiment, the compound, or a salt thereof, has a structure described herein, and $R^b$ is as described herein, and R is Br. In an exemplary embodiment, the compound, or a salt thereof, has a structure described herein, and $R^b$ is as described herein, and R is Cl. In an exemplary embodiment, the compound, or a salt thereof, has a structure described herein, and $R^b$ is as described herein, and R is F. In an exemplary embodiment, the compound, or a salt thereof, has a structure described herein, and $R^b$ is as described herein, and R is unsubstituted $C_1$ or $C_2$ or $C_3$ or $C_4$ alkyl. In an exemplary embodiment, the compound, or a salt thereof, has a structure described herein, and $R^b$ is as described herein, and R is methyl. In an exemplary embodiment, the compound, or a salt thereof, has a structure described herein, and $R^b$ is as described herein, and R is ethyl. In an exemplary embodiment, the compound, or a salt thereof, has a structure described herein, and $R^b$ is as described herein, and R is propyl. In an exemplary embodiment, the compound, or a salt thereof, has a structure described herein, and $R^b$ is as described herein, and R is isopropyl. In an exemplary embodiment, the compound, or a salt thereof, has a structure described herein, and $R^b$ is as described herein, and R is butyl. In an exemplary embodiment, the compound, or a salt thereof, has a structure described herein, and $R^b$ is as described herein, and R is isobutyl.

In an exemplary embodiment, the compound, or a salt thereof, has a structure which is

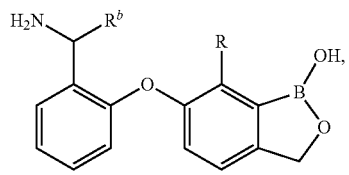

or a salt thereof, wherein R and $R^b$ are as described herein. In an exemplary embodiment, the compound, or a salt thereof, has a structure which is

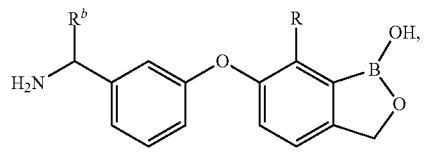

or a salt thereof, wherein R and $R^b$ are as described herein. In an exemplary embodiment, the compound, or a salt thereof, has a structure which is

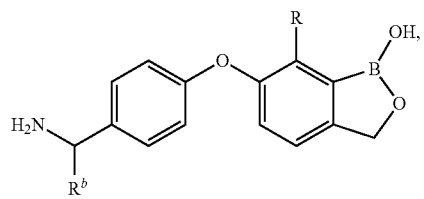

or a salt thereof, wherein R and $R^b$ are as described herein. In an exemplary embodiment, the compound, or a salt thereof, R is methyl, and $R^b$ is as described herein. In an exemplary embodiment, the compound, or a salt thereof, R is ethyl, and $R^b$ is as described herein. In an exemplary embodiment, the compound, or a salt thereof, R is isopropyl, and $R^b$ is as described herein. In an exemplary embodiment, the compound, or a salt thereof, $R^b$ is methyl, and R is as described herein.

In an exemplary embodiment, the compound, or a salt thereof, has a structure which is

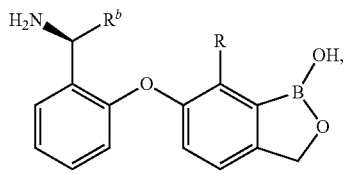

or a salt thereof, wherein R and $R^b$ are as described herein. In an exemplary embodiment, the compound, or a salt thereof, has a structure which is

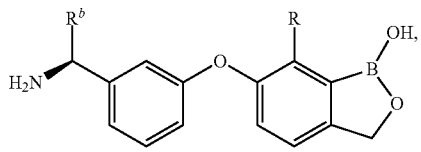

or a salt thereof, wherein R and $R^b$ are as described herein. In an exemplary embodiment, the compound, or a salt thereof, has a structure which is

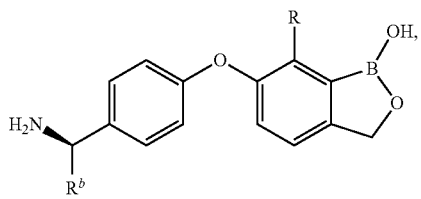

or a salt thereof, wherein R and $R^b$ are as described herein. In an exemplary embodiment, the compound, or a salt thereof, R is methyl, and $R^b$ is as described herein. In an exemplary embodiment, the compound, or a salt thereof, R is ethyl, and $R^b$ is as described herein. In an exemplary embodiment, the compound, or a salt thereof, R is isopropyl, and $R^b$ is as described herein. In an exemplary embodiment, the compound, or a salt thereof, $R^b$ is methyl, and R is as described herein.

In an exemplary embodiment, the compound, or a salt thereof, has a structure which is

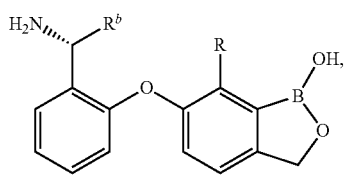

or a salt thereof, wherein R and $R^b$ are as described herein. In an exemplary embodiment, the compound, or a salt thereof, has a structure which is

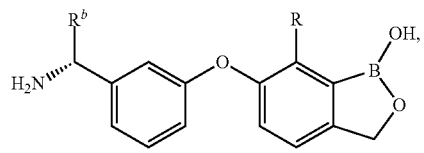

or a salt thereof, wherein R and $R^b$ are as described herein. In an exemplary embodiment, the compound, or a salt thereof, has a structure which is

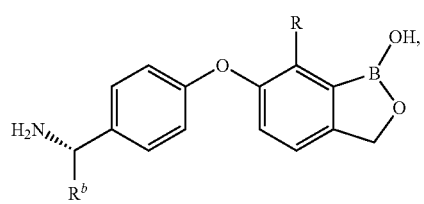

or a salt thereof, wherein R and $R^b$ are as described herein. In an exemplary embodiment, the compound, or a salt thereof, R is methyl, and $R^b$ is as described herein. In an exemplary embodiment, the compound, or a salt thereof, R is ethyl, and $R^b$ is as described herein. In an exemplary embodiment, the compound, or a salt thereof, R is isopropyl, and $R^b$ is as described herein. In an exemplary embodiment, the compound, or a salt thereof, $R^b$ is methyl, and R is as described herein.

In an exemplary embodiment, the compound, or a salt thereof, has a structure which is

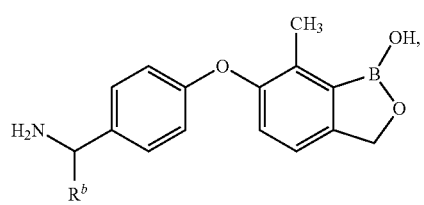

wherein $R^b$ is as described herein. In an exemplary embodiment, the compound, or a salt thereof, has a structure which is

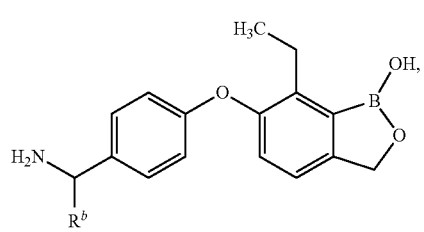

wherein R$^b$ is as described herein. In an exemplary embodiment, the compound, or a salt thereof, has a structure which is

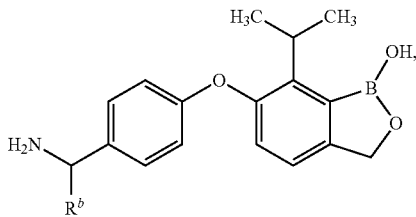

wherein R$^b$ is as described herein. In an exemplary embodiment, the compound, or a salt thereof, has a structure which is

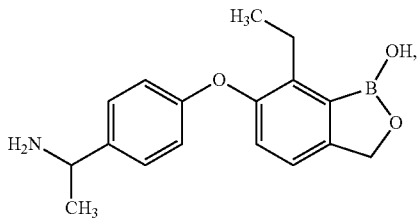 [SMILES: CCc1c(Oc2ccc(C(C)N)cc2)ccc2c1B(O)OC2]

In an exemplary embodiment, the compound, or a salt thereof, has a structure which is

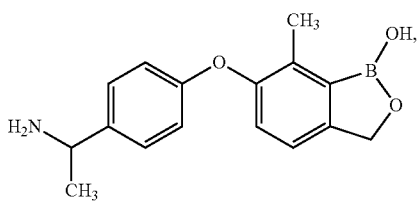

In an exemplary embodiment, the compound, or a salt thereof, has a structure which is

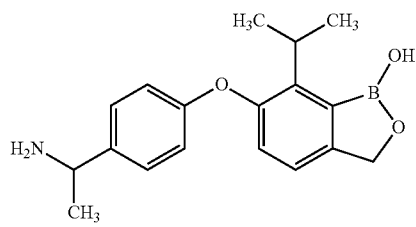 [SMILES: CC(C)c1c(Oc2ccc(C(C)N)cc2)ccc2c1B(O)OC2]

In an exemplary embodiment, the compound, or a salt thereof, has a structure which is

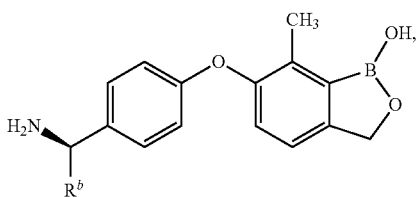

wherein R$^b$ is as described herein. In an exemplary embodiment, the compound, or a salt thereof, has a structure which is

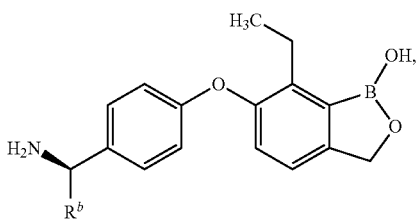

wherein R$^b$ is as described herein. In an exemplary embodiment, the compound, or a salt thereof, has a structure which is

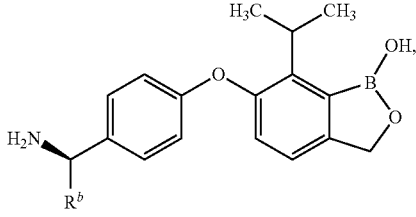

wherein R$^b$ is as described herein. In an exemplary embodiment, the compound, or a salt thereof, has a structure which is

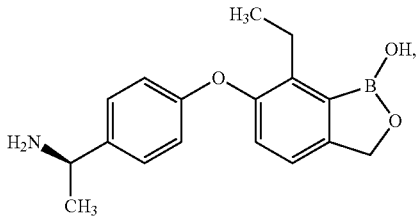

In an exemplary embodiment, the compound, or a salt thereof, has a structure which is

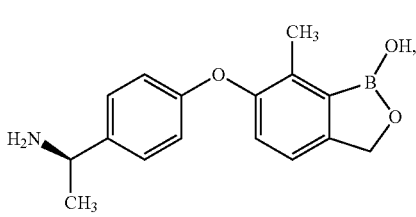

In an exemplary embodiment, the compound, or a salt thereof, has a structure which is

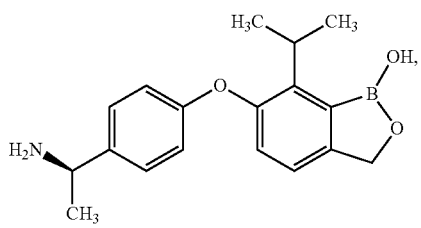 [SMILES: CC(C)c1c(Oc2ccc([C@@H](C)N)cc2)ccc2c1B(O)OC2]

In an exemplary embodiment, the compound, or a salt thereof, has a structure which is

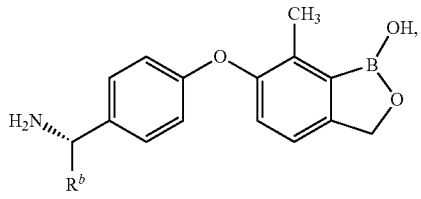

wherein $R^b$ is as described herein. In an exemplary embodiment, the compound, or a salt thereof, has a structure which is

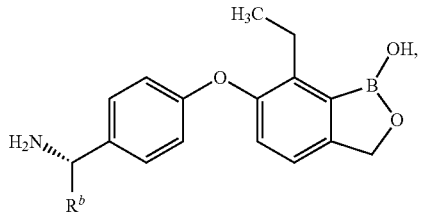

wherein $R^b$ is as described herein. In an exemplary embodiment, the compound, or a salt thereof, has a structure which is

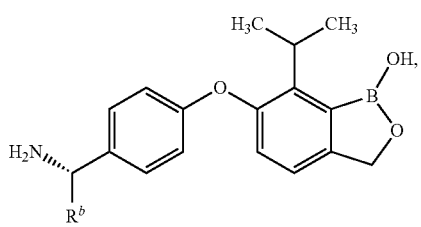

wherein $R^b$ is as described herein. In an exemplary embodiment, the compound, or a salt thereof, has a structure which is

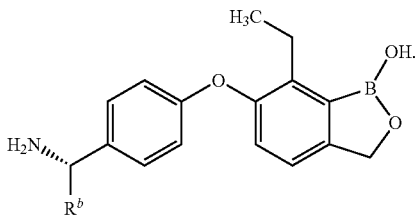

In an exemplary embodiment, the compound, or a salt thereof, has a structure which is

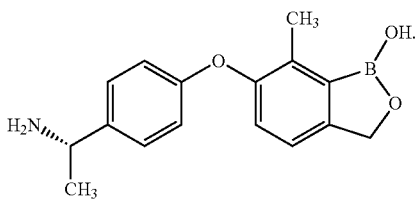 [SMILES: Cc1c(Oc2ccc([C@H](C)N)cc2)ccc2c1B(O)OC2]

In an exemplary embodiment, the compound, or a salt thereof, has a structure which is

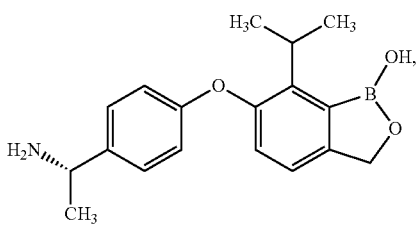

In an exemplary embodiment, the compound, or a salt thereof, has a structure which is

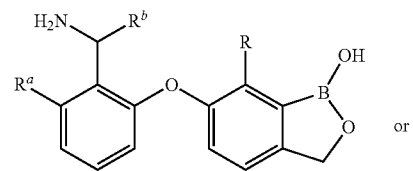

or

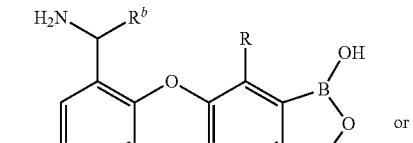

or

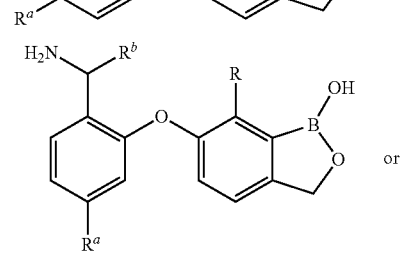

or

-continued

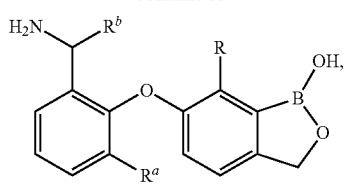

wherein R, $R^a$ and $R^b$ are as described herein. In an exemplary embodiment, the compound, or a salt thereof, has a structure which is

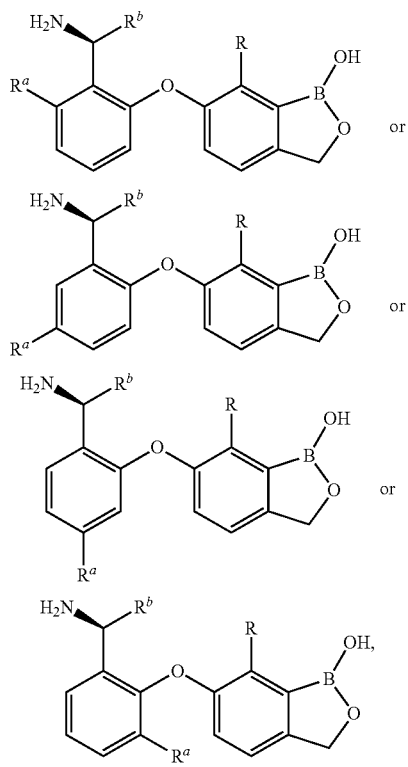

wherein R, $R^a$ and $R^b$ are as described herein. In an exemplary embodiment, the compound, or a salt thereof, has a structure which is

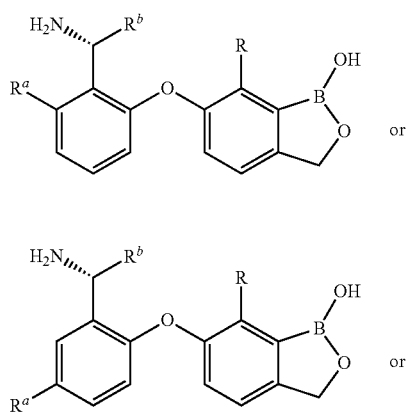

-continued

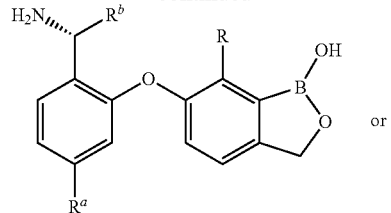

or

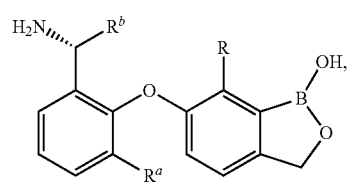

wherein R, $R^a$ and $R^b$ are as described herein. In an exemplary embodiment, the compound, or a salt thereof, wherein $R^a$ and $R^b$ are as described herein, and R is Br. In an exemplary embodiment, the compound, or a salt thereof, wherein $R^a$ and $R^b$ are as described herein, and R is Cl. In an exemplary embodiment, the compound, or a salt thereof, wherein $R^a$ and $R^b$ are as described herein, and R is F. In an exemplary embodiment, the compound, or a salt thereof, wherein $R^a$ and $R^b$ are as described herein, and R is unsubstituted $C_1$ or $C_2$ or $C_3$ or $C_4$ alkyl. In an exemplary embodiment, the compound, or a salt thereof, wherein $R^a$ and $R^b$ are as described herein, and R is methyl. In an exemplary embodiment, the compound, or a salt thereof, wherein $R^a$ and $R^b$ are as described herein, and R is ethyl. In an exemplary embodiment, the compound, or a salt thereof, wherein $R^a$ and $R^b$ are as described herein, and R is isopropyl.

In an exemplary embodiment, the compound, or a salt thereof, has a structure which is

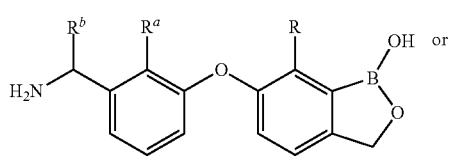

or

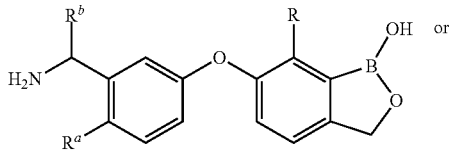

or

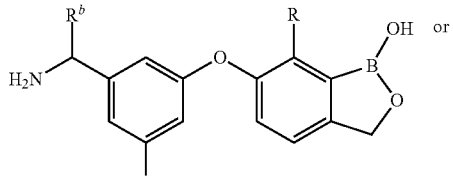

or

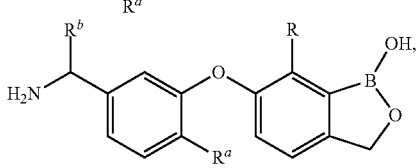

wherein R, $R^a$ and $R^b$ are as described herein. In an exemplary embodiment, the compound, or a salt thereof, has a structure which is

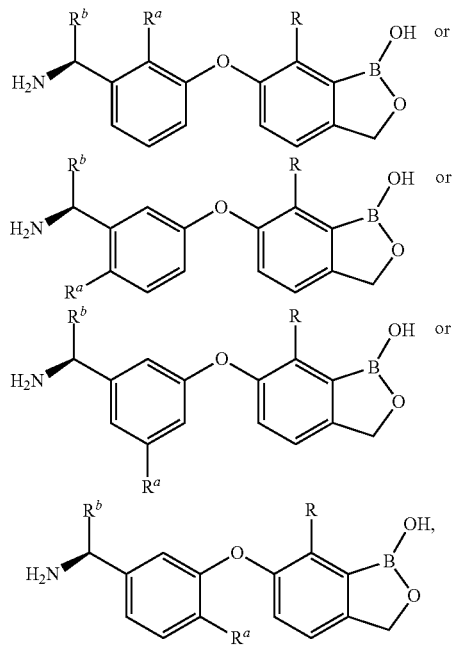

wherein R, $R^a$ and $R^b$ are as described herein. In an exemplary embodiment, the compound, or a salt thereof, has a structure which is

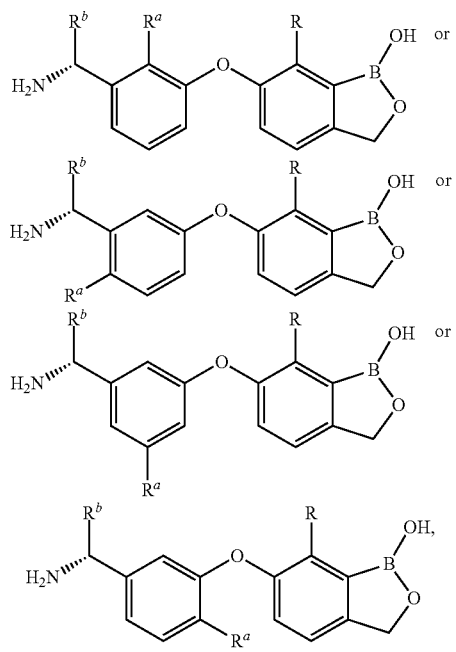

wherein R, $R^a$ and $R^b$ are as described herein. In an exemplary embodiment, the compound, or a salt thereof, wherein $R^a$ and $R^b$ are as described herein, and R is Br. In an exemplary embodiment, the compound, or a salt thereof, wherein $R^a$ and $R^b$ are as described herein, and R is Cl. In an exemplary embodiment, the compound, or a salt thereof, wherein $R^a$ and $R^b$ are as described herein, and R is F. In an exemplary embodiment, wherein $R^a$ and $R^b$ are as described herein, and R is unsubstituted $C_1$ or $C_2$ or $C_3$ or $C_4$ alkyl. In an exemplary embodiment, wherein $R^a$ and $R^b$ are as described herein, and R is methyl. In an exemplary embodiment, wherein $R^a$ and $R^b$ are as described herein, and R is ethyl. In an exemplary embodiment, wherein $R^a$ and $R^b$ are as described herein, and R is isopropyl.

In an exemplary embodiment, the compound, or a salt thereof, has a structure which is

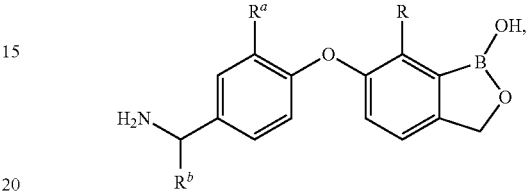

wherein R, $R^a$ and $R^b$ are as described herein. In an exemplary embodiment, the compound, or a salt thereof, has a structure which is

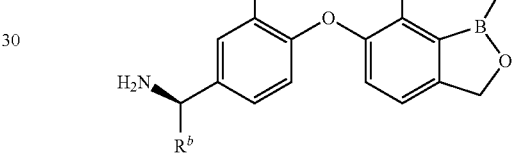

wherein R, $R^a$ and $R^b$ are as described herein. In an exemplary embodiment, the compound, or a salt thereof, has a structure which is

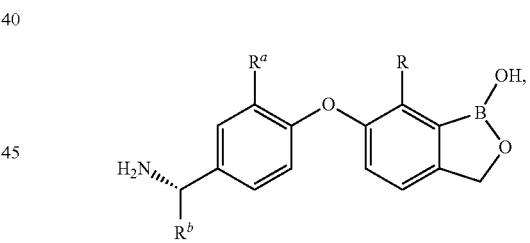

wherein R, $R^a$ and $R^b$ are as described herein. In an exemplary embodiment, the compound, or a salt thereof, wherein $R^a$ and $R^b$ are as described herein, and R is Br. In an exemplary embodiment, the compound, or a salt thereof, wherein $R^a$ and $R^b$ are as described herein, and R is Cl. In an exemplary embodiment, the compound, or a salt thereof, wherein $R^a$ and $R^b$ are as described herein, and R is F. In an exemplary embodiment, the compound, or a salt thereof, wherein $R^a$ and $R^b$ are as described herein, and R is unsubstituted $C_1$ or $C_2$ or $C_3$ or $C_4$ alkyl. In an exemplary embodiment, the compound, or a salt thereof, wherein $R^a$ and $R^b$ are as described herein, and R is methyl. In an exemplary embodiment, the compound, or a salt thereof, wherein $R^a$ and $R^b$ are as described herein, and R is ethyl. In an exemplary embodiment, the compound, or a salt thereof, wherein $R^a$ and $R^b$ are as described herein, and R is isopropyl.

In an exemplary embodiment, the compound, or a salt thereof, has a structure which is

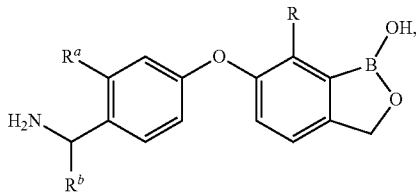

wherein R, R$^a$ and R$^b$ are as described herein. In an exemplary embodiment, the compound, or a salt thereof, has a structure which is

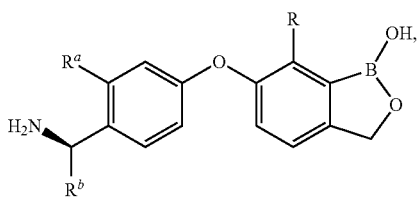

wherein R, R$^a$ and R$^b$ are as described herein. In an exemplary embodiment, the compound, or a salt thereof, has a structure which is

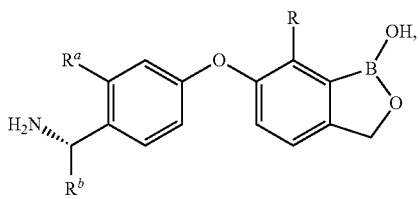

wherein R, R$^a$ and R$^b$ are as described herein. In an exemplary embodiment, the compound, or a salt thereof, wherein R$^a$ and R$^b$ are as described herein, and R is Br. In an exemplary embodiment, the compound, or a salt thereof, wherein R$^a$ and R$^b$ are as described herein, and R is Cl. In an exemplary embodiment, the compound, or a salt thereof, wherein R$^a$ and R$^b$ are as described herein, and R is F. In an exemplary embodiment, the compound, or a salt thereof, wherein R$^a$ and R$^b$ are as described herein, and R is unsubstituted C$_1$ or C$_2$ or C$_3$ or C$_4$ alkyl. In an exemplary embodiment, the compound, or a salt thereof, wherein R$^a$ and R$^b$ are as described herein, and R is methyl. In an exemplary embodiment, the compound, or a salt thereof, wherein R$^a$ and R$^b$ are as described herein, and R is ethyl. In an exemplary embodiment, the compound, or a salt thereof, wherein R$^a$ and R$^b$ are as described herein, and R is isopropyl. In an exemplary embodiment, the compound, or a salt thereof, wherein R$^b$ is as described herein, R$^a$ is F, and R is Br. In an exemplary embodiment, the compound, or a salt thereof, wherein R$^b$ is as described herein, R$^a$ is Cl, and R is Br. In an exemplary embodiment, the compound, or a salt thereof, wherein R$^b$ is as described herein, R$^a$ is F, and R is Cl. In an exemplary embodiment, the compound, or a salt thereof, wherein R$^b$ is as described herein, R$^a$ is Cl, and R is Cl. In an exemplary embodiment, the compound, or a salt thereof, wherein R$^b$ is as described herein, R$^a$ is F, and R is F. In an exemplary embodiment, the compound, or a salt thereof, wherein R$^b$ is as described herein, R$^a$ is Cl, and R is F. In an exemplary embodiment, the compound, or a salt thereof, wherein R$^b$ is as described herein, R$^a$ is F, and R is unsubstituted C$_1$ or C$_2$ or C$_3$ or C$_4$ alkyl. In an exemplary embodiment, the compound, or a salt thereof, wherein R$^b$ is as described herein, R$^a$ is Cl, and R is unsubstituted C$_1$ or C$_2$ or C$_3$ or C$_4$ alkyl. In an exemplary embodiment, the compound, or a salt thereof, wherein R$^b$ is as described herein, R$^a$ is F, and R is methyl. In an exemplary embodiment, the compound, or a salt thereof, wherein R$^b$ is as described herein, R$^a$ is Cl, and R is methyl. In an exemplary embodiment, the compound, or a salt thereof, wherein R$^b$ is as described herein, R$^a$ is F, and R is ethyl. In an exemplary embodiment, the compound, or a salt thereof, wherein R$^b$ is as described herein, R$^a$ is Cl, and R is ethyl. In an exemplary embodiment, the compound, or a salt thereof, wherein R$^b$ is as described herein, R$^a$ is F, and R is isopropyl. In an exemplary embodiment, the compound, or a salt thereof, wherein R$^b$ is as described herein, R$^a$ is Cl, and R is isopropyl. In an exemplary embodiment, the compound, or a salt thereof, wherein R$^b$ is methyl, R$^a$ is F, and R is Br. In an exemplary embodiment, the compound, or a salt thereof, wherein R$^b$ is methyl, R$^a$ is Cl, and R is Br. In an exemplary embodiment, the compound, or a salt thereof, wherein R$^b$ is methyl, R$^a$ is F, and R is Cl. In an exemplary embodiment, the compound, or a salt thereof, wherein R$^b$ is methyl, R$^a$ is Cl, and R is Cl. In an exemplary embodiment, the compound, or a salt thereof, wherein R$^b$ is methyl, R$^a$ is F, and R is F. In an exemplary embodiment, the compound, or a salt thereof, wherein R$^b$ is methyl, R$^a$ is Cl, and R is F. In an exemplary embodiment, the compound, or a salt thereof, wherein R$^b$ is methyl, R$^a$ is F, and R is unsubstituted C$_1$ or C$_2$ or C$_3$ or C$_4$ alkyl. In an exemplary embodiment, the compound, or a salt thereof, wherein R$^b$ is methyl, R$^a$ is Cl, and R is unsubstituted C$_1$ or C$_2$ or C$_3$ or C$_4$ alkyl. In an exemplary embodiment, the compound, or a salt thereof, wherein R$^b$ is methyl, R$^a$ is F, and R is methyl. In an exemplary embodiment, the compound, or a salt thereof, wherein R$^b$ is methyl, R$^a$ is Cl, and R is methyl. In an exemplary embodiment, the compound, or a salt thereof, wherein R$^b$ is methyl, R$^a$ is F, and R is ethyl. In an exemplary embodiment, the compound, or a salt thereof, wherein R$^b$ is methyl, R$^a$ is Cl, and R is ethyl. In an exemplary embodiment, the compound, or a salt thereof, wherein R$^b$ is methyl, R$^a$ is F, and R is isopropyl. In an exemplary embodiment, the compound, or a salt thereof, wherein R$^b$ is methyl, R$^a$ is Cl, and R is isopropyl.

In an exemplary embodiment, the compound, or a salt thereof, has a structure which is

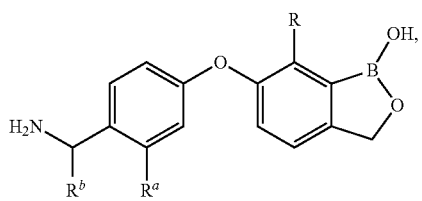

wherein R, $R^a$ and $R^b$ are as described herein. In an exemplary embodiment, the compound, or a salt thereof, has a structure which is

[Chemical structure showing a compound with H₂N, $R^b$, $R^a$, R, OH, B, O groups]

wherein R, $R^a$ and $R^b$ are as described herein. In an exemplary embodiment, the compound, or a salt thereof, has a structure which is

[Chemical structure showing a compound with H₂N (with wedge bond), $R^b$, $R^a$, R, OH, B, O groups]

wherein R, $R^a$ and $R^b$ are as described herein. In an exemplary embodiment, the compound, or a salt thereof, wherein $R^a$ and $R^b$ are as described herein, and R is Br. In an exemplary embodiment, the compound, or a salt thereof, wherein $R^a$ and $R^b$ are as described herein, and R is Cl. In an exemplary embodiment, the compound, or a salt thereof, wherein $R^a$ and $R^b$ are as described herein, and R is F. In an exemplary embodiment, the compound, or a salt thereof, wherein $R^a$ and $R^b$ are as described herein, and R is unsubstituted $C_1$ or $C_2$ or $C_3$ or $C_4$ alkyl. In an exemplary embodiment, the compound, or a salt thereof, wherein $R^a$ and $R^b$ are as described herein, and R is methyl. In an exemplary embodiment, the compound, or a salt thereof, wherein $R^a$ and $R^b$ are as described herein, and R is ethyl. In an exemplary embodiment, the compound, or a salt thereof, wherein $R^a$ and $R^b$ are as described herein, and R is isopropyl. In an exemplary embodiment, the compound, or a salt thereof, wherein $R^b$ is as described herein, $R^a$ is F, and R is Br. In an exemplary embodiment, the compound, or a salt thereof, wherein $R^b$ is as described herein, $R^a$ is Cl, and R is Br. In an exemplary embodiment, the compound, or a salt thereof, wherein $R^b$ is as described herein, $R^a$ is F, and R is Cl. In an exemplary embodiment, the compound, or a salt thereof, wherein $R^b$ is as described herein, $R^a$ is Cl, and R is Cl. In an exemplary embodiment, the compound, or a salt thereof, wherein $R^b$ is as described herein, $R^a$ is F, and R is F. In an exemplary embodiment, the compound, or a salt thereof, wherein $R^b$ is as described herein, $R^a$ is Cl, and R is F. In an exemplary embodiment, the compound, or a salt thereof, wherein $R^b$ is as described herein, $R^a$ is F, and R is unsubstituted $C_1$ or $C_2$ or $C_3$ or $C_4$ alkyl. In an exemplary embodiment, the compound, or a salt thereof, wherein $R^b$ is as described herein, $R^a$ is Cl, and R is unsubstituted $C_1$ or $C_2$ or $C_3$ or $C_4$ alkyl. In an exemplary embodiment, the compound, or a salt thereof, wherein $R^b$ is as described herein, $R^a$ is F, and R is methyl. In an exemplary embodiment, the compound, or a salt thereof, wherein $R^b$ is as described herein, $R^a$ is Cl, and R is methyl. In an exemplary embodiment, the compound, or a salt thereof, wherein $R^b$ is as described herein, $R^a$ is F, and R is ethyl. In an exemplary embodiment, the compound, or a salt thereof, wherein $R^b$ is as described herein, $R^a$ is Cl, and R is ethyl. In an exemplary embodiment, the compound, or a salt thereof, wherein $R^b$ is as described herein, $R^a$ is F, and R is isopropyl. In an exemplary embodiment, the compound, or a salt thereof, wherein $R^b$ is as described herein, $R^a$ is Cl, and R is isopropyl. In an exemplary embodiment, the compound, or a salt thereof, wherein $R^b$ is methyl, $R^a$ is F, and R is Br. In an exemplary embodiment, the compound, or a salt thereof, wherein $R^b$ is methyl, $R^a$ is Cl, and R is Br. In an exemplary embodiment, the compound, or a salt thereof, wherein $R^b$ is methyl, $R^a$ is F, and R is Cl. In an exemplary embodiment, the compound, or a salt thereof, wherein $R^b$ is methyl, $R^a$ is Cl, and R is Cl. In an exemplary embodiment, the compound, or a salt thereof, wherein $R^b$ is methyl, $R^a$ is F, and R is F. In an exemplary embodiment, the compound, or a salt thereof, wherein $R^b$ is methyl, $R^a$ is Cl, and R is F. In an exemplary embodiment, the compound, or a salt thereof, wherein $R^b$ is methyl, $R^a$ is F, and R is unsubstituted $C_1$ or $C_2$ or $C_3$ or $C_4$ alkyl. In an exemplary embodiment, the compound, or a salt thereof, wherein $R^b$ is methyl, $R^a$ is Cl, and R is unsubstituted $C_1$ or $C_2$ or $C_3$ or $C_4$ alkyl. In an exemplary embodiment, the compound, or a salt thereof, wherein $R^b$ is methyl, $R^a$ is F, and R is methyl. In an exemplary embodiment, the compound, or a salt thereof, wherein $R^b$ is methyl, $R^a$ is Cl, and R is methyl. In an exemplary embodiment, the compound, or a salt thereof, wherein $R^b$ is methyl, $R^a$ is F, and R is ethyl. In an exemplary embodiment, the compound, or a salt thereof, wherein $R^b$ is methyl, $R^a$ is Cl, and R is ethyl. In an exemplary embodiment, the compound, or a salt thereof, wherein $R^b$ is methyl, $R^a$ is F, and R is isopropyl. In an exemplary embodiment, the compound, or a salt thereof, wherein $R^b$ is methyl, $R^a$ is Cl, and R is isopropyl.

In an exemplary embodiment, the compound, or a salt thereof, has a structure which is

[Chemical structure showing a compound with H₂N, $R^b$, $R^a$, R, OH, B, O groups]

wherein R, $R^a$ and $R^b$ are as described herein. In an exemplary embodiment, the compound, or a salt thereof, has a structure which is

[Chemical structure showing a compound with H₂N (with wedge bond), $R^b$, $R^a$, R, OH, B, O groups]

wherein R, $R^a$ and $R^b$ are as described herein. In an exemplary embodiment, the compound, or a salt thereof, has a structure which is

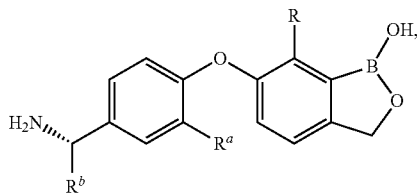

wherein R, $R^a$ and $R^b$ are as described herein. In an exemplary embodiment, the compound, or a salt thereof, wherein $R^a$ and $R^b$ are as described herein, and R is Br. In an exemplary embodiment, the compound, or a salt thereof, wherein $R^a$ and $R^b$ are as described herein, and R is Cl. In an exemplary embodiment, the compound, or a salt thereof, wherein $R^a$ and $R^b$ are as described herein, and R is F. In an exemplary embodiment, the compound, or a salt thereof, wherein $R^a$ and $R^b$ are as described herein, and R is unsubstituted $C_1$ or $C_2$ or $C_3$ or $C_4$ alkyl. In an exemplary embodiment, the compound, or a salt thereof, wherein $R^a$ and $R^b$ are as described herein, and R is methyl. In an exemplary embodiment, the compound, or a salt thereof, wherein $R^a$ and $R^b$ are as described herein, and R is ethyl. In an exemplary embodiment, the compound, or a salt thereof, wherein $R^a$ and $R^b$ are as described herein, and R is isopropyl. In an exemplary embodiment, the compound, or a salt thereof, wherein $R^b$ is as described herein, $R^a$ is F, and R is Br. In an exemplary embodiment, the compound, or a salt thereof, wherein $R^b$ is as described herein, $R^a$ is Cl, and R is Br. In an exemplary embodiment, the compound, or a salt thereof, wherein $R^b$ is as described herein, $R^a$ is F, and R is Cl. In an exemplary embodiment, the compound, or a salt thereof, wherein $R^b$ is as described herein, $R^a$ is Cl, and R is Cl. In an exemplary embodiment, the compound, or a salt thereof, wherein $R^b$ is as described herein, $R^a$ is F, and R is F. In an exemplary embodiment, the compound, or a salt thereof, wherein $R^b$ is as described herein, $R^a$ is Cl, and R is F. In an exemplary embodiment, the compound, or a salt thereof, wherein $R^b$ is as described herein, $R^a$ is F, and R is unsubstituted $C_1$ or $C_2$ or $C_3$ or $C_4$ alkyl. In an exemplary embodiment, the compound, or a salt thereof, wherein $R^b$ is as described herein, $R^a$ is Cl, and R is unsubstituted $C_1$ or $C_2$ or $C_3$ or $C_4$ alkyl. In an exemplary embodiment, the compound, or a salt thereof, wherein $R^b$ is as described herein, $R^a$ is F, and R is methyl. In an exemplary embodiment, the compound, or a salt thereof, wherein $R^b$ is as described herein, $R^a$ is Cl, and R is methyl. In an exemplary embodiment, the compound, or a salt thereof, wherein $R^b$ is as described herein, $R^a$ is F, and R is ethyl. In an exemplary embodiment, the compound, or a salt thereof, wherein $R^b$ is as described herein, $R^a$ is Cl, and R is ethyl. In an exemplary embodiment, the compound, or a salt thereof, wherein $R^b$ is as described herein, $R^a$ is F, and R is isopropyl. In an exemplary embodiment, the compound, or a salt thereof, wherein $R^b$ is as described herein, $R^a$ is Cl, and R is isopropyl. In an exemplary embodiment, the compound, or a salt thereof, wherein $R^b$ is methyl, $R^a$ is F, and R is Br. In an exemplary embodiment, the compound, or a salt thereof, wherein $R^b$ is methyl, $R^a$ is Cl, and R is Br. In an exemplary embodiment, the compound, or a salt thereof, wherein $R^b$ is methyl, $R^a$ is F, and R is Cl. In an exemplary embodiment, the compound, or a salt thereof, wherein $R^b$ is methyl, $R^a$ is Cl, and R is Cl. In an exemplary embodiment, the compound, or a salt thereof, wherein $R^b$ is methyl, $R^a$ is F, and R is F. In an exemplary embodiment, the compound, or a salt thereof, wherein $R^b$ is methyl, $R^a$ is Cl, and R is F. In an exemplary embodiment, the compound, or a salt thereof, wherein $R^b$ is methyl, $R^a$ is F, and R is unsubstituted $C_1$ or $C_2$ or $C_3$ or $C_4$ alkyl. In an exemplary embodiment, the compound, or a salt thereof, wherein $R^b$ is methyl, $R^a$ is Cl, and R is unsubstituted $C_1$ or $C_2$ or $C_3$ or $C_4$ alkyl. In an exemplary embodiment, the compound, or a salt thereof, wherein $R^b$ is methyl, $R^a$ is F, and R is methyl. In an exemplary embodiment, the compound, or a salt thereof, wherein $R^b$ is methyl, $R^a$ is Cl, and R is methyl. In an exemplary embodiment, the compound, or a salt thereof, wherein $R^b$ is methyl, $R^a$ is F, and R is ethyl. In an exemplary embodiment, the compound, or a salt thereof, wherein $R^b$ is methyl, $R^a$ is Cl, and R is ethyl. In an exemplary embodiment, the compound, or a salt thereof, wherein $R^b$ is methyl, $R^a$ is F, and R is isopropyl. In an exemplary embodiment, the compound, or a salt thereof, wherein $R^b$ is methyl, $R^a$ is Cl, and R is isopropyl.

In another exemplary embodiment, the invention provides poly- or multi-valent species of the compounds of the invention. In an exemplary embodiment, the invention provides a dimer of a compound of the invention. In an exemplary embodiment, the invention provides a dimer of a compound described herein.

In an exemplary embodiment, the invention provides an anhydride of a compound of the invention. In an exemplary embodiment, the invention provides an anhydride of a compound described herein.

In an exemplary embodiment, the invention provides a trimer of a compound of the invention. In an exemplary embodiment, the invention provides a trimer of a compound described herein.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is linear alkyl. In an exemplary embodiment, alkyl is branched alkyl. In an exemplary embodiment, heteroalkyl is linear heteroalkyl. In an exemplary embodiment, heteroalkyl is branched heteroalkyl.

III.b) Preparation of Boron-Containing Compounds

Compounds of use in the present invention can be prepared using commercially available starting materials or known intermediates. Compounds of use in the present invention can be prepared using synthetic methods known in the art or described herein.

The following exemplary schemes illustrate methods of preparing boron-containing molecules of the present invention. These methods are not limited to producing the compounds shown, but can be used to prepare a variety of molecules such as the compounds and complexes described herein. The compounds of the present invention can also be synthesized by methods not explicitly illustrated in the schemes but are well within the skill of one in the art. The compounds can be prepared using readily available materials of known intermediates.

Scheme 1

In one embodiment, the compound of the invention can be synthesized according to the following scheme:

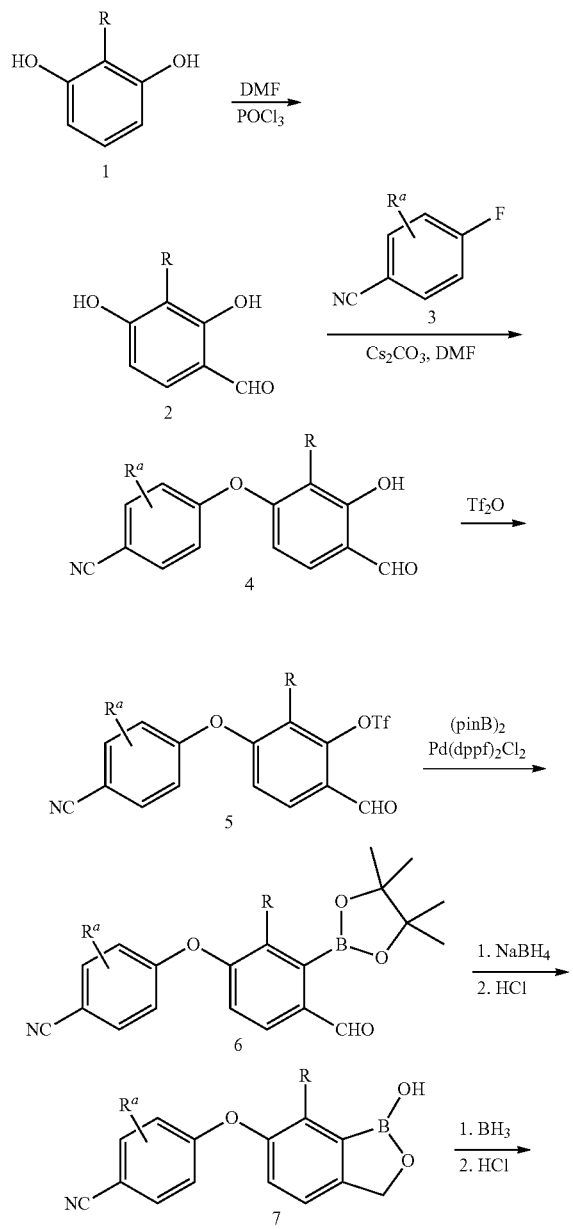

Scheme 2

In one embodiment, the compound of the invention can be synthesized according to the following scheme:

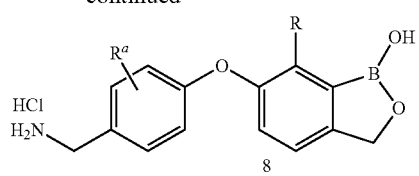

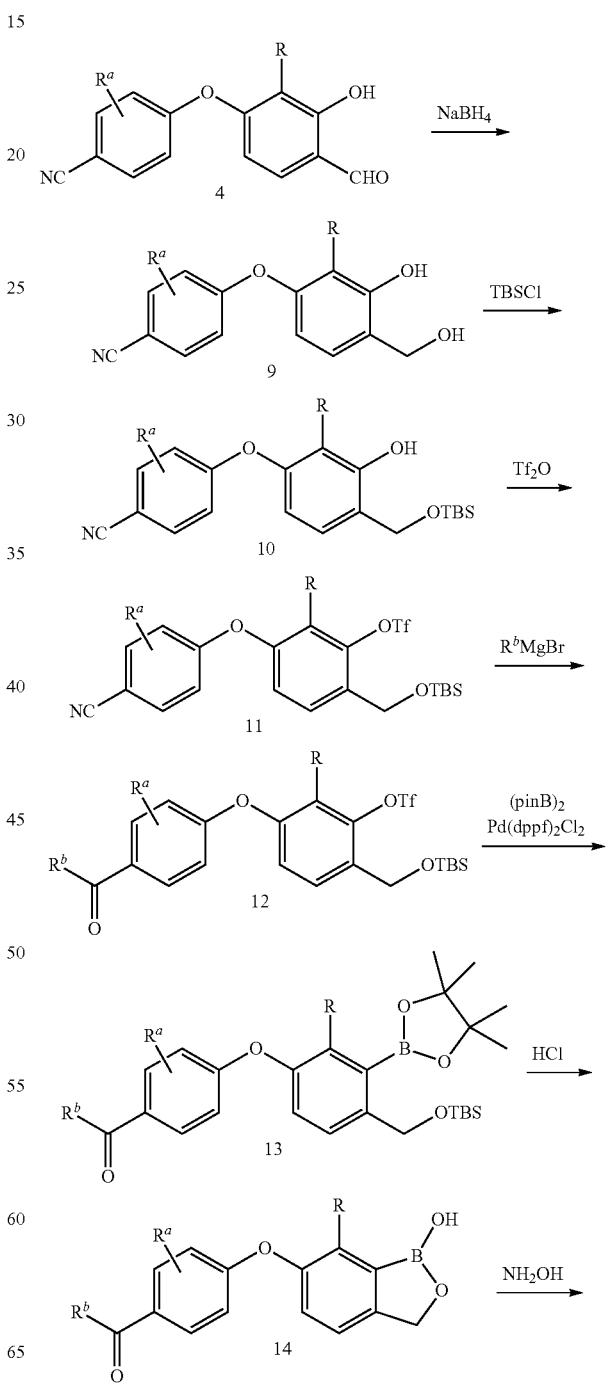

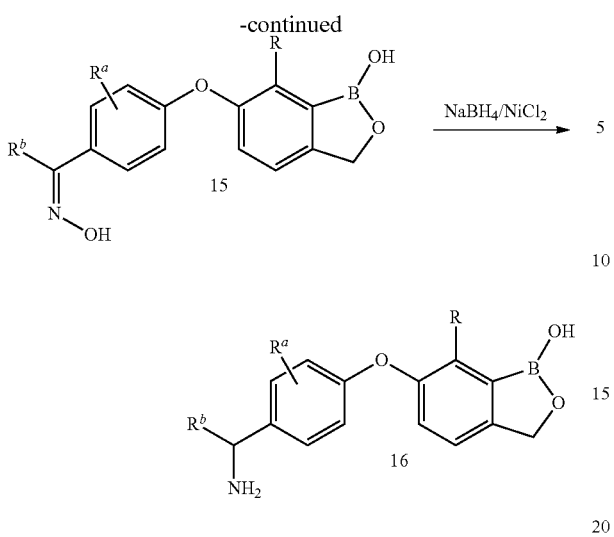
Scheme 3
In one embodiment, the compound of the invention can be synthesized according to the following scheme:
Scheme 4
In one embodiment, the compound of the invention can be synthesized according to the following scheme:
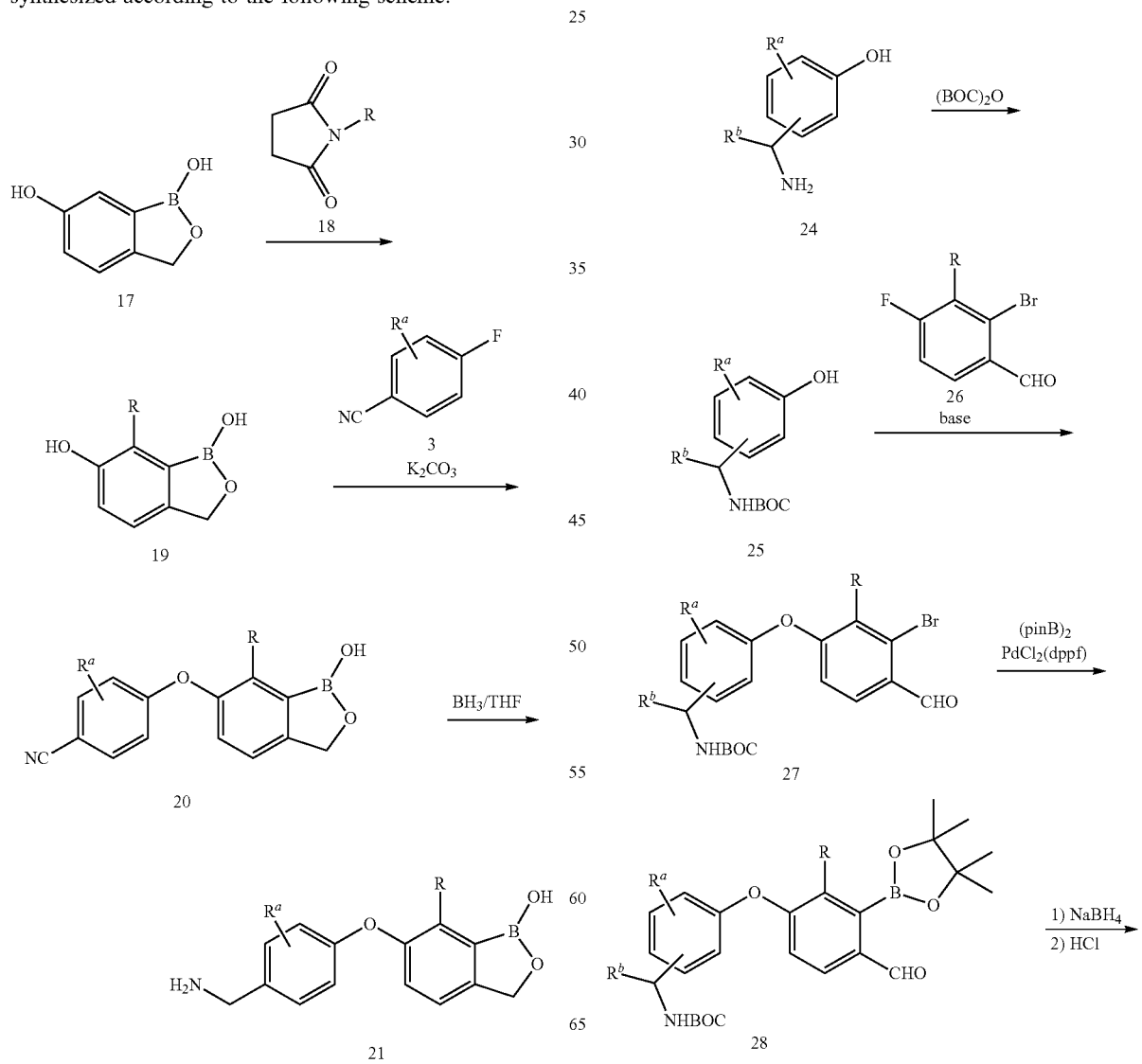

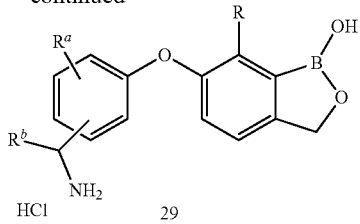

Compounds described herein can be converted into hydrates and solvates by methods similar to those described herein.

III.c) Combinations Comprising Additional Therapeutic Agents

The compounds of the invention may also be used in combination with additional therapeutic agents. The invention thus provides, in a further aspect, a combination comprising a compound described herein or a pharmaceutically acceptable salt thereof together with at least one additional therapeutic agent. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom. In an exemplary embodiment, the additional therapeutic agent is a compound described in sections III a)-b).

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

IV. The Methods a) Kinases

In another aspect, the invention provides a method for inhibiting a kinase, the method comprising: contacting the kinase with a compound of the invention, wherein the kinase is inhibited. In an exemplary embodiment, the kinase includes a hinge region. In an exemplary embodiment, the kinase is a serine/threonine kinase. In an exemplary embodiment, the kinase is an ACG kinase. In an exemplary embodiment, the kinase is a Rho kinase. In an exemplary embodiment, the kinase is ROCK1. In an exemplary embodiment, the kinase is ROCK2. In an exemplary embodiment, the kinase is a NAK kinase. In an exemplary embodiment, the kinase is AAK1. In an exemplary embodiment, the compound of the invention is a compound described herein or a pharmaceutically acceptable salt thereof. In an exemplary embodiment, the compound of the invention is a compound described herein. In an exemplary embodiment, the amount is a therapeutically effective amount. In an exemplary embodiment, the compound is according to a formula described herein.

b) Conditions and Effects

In another aspect, the invention provides a method of treating and/or preventing a condition, or enhancing an effect, in an animal, the method comprising administering to the animal an amount of a compound of the invention, thereby treating or preventing the condition, or enhancing the effect. In an exemplary embodiment, the invention provides a method of treating a condition, in an animal in need of treatment thereof, the method comprising administering to the animal an amount of a compound of the invention, thereby treating the condition. In an exemplary embodiment, the invention provides a method of preventing a condition, in an animal in need of prevention, the method comprising administering to the animal an amount of a compound of the invention, thereby preventing the condition. In an exemplary embodiment, the invention provides a method of enhancing an effect, in an animal in need of enhancement thereof, the method comprising administering to the animal an amount of a compound of the invention, thereby enhancing the effect. In an exemplary embodiment, the condition is a disease. In an exemplary embodiment, the condition is a disease. In an exemplary embodiment, the compound of the invention is a compound described herein or a pharmaceutically acceptable salt thereof. In an exemplary embodiment, the compound of the invention is a compound described herein. In an exemplary embodiment, the amount is a therapeutically effective amount.

In an exemplary embodiment, the condition is selected from the group consisting of glaucoma, asthma, pulmonary hypertension, angina, heart failure, wound healing, and spinal cord injury. In an exemplary embodiment, the condition is pulmonary hypertension.

In an exemplary embodiment, the condition is glaucoma. In an exemplary embodiment, the glaucoma is selected from the group consisting of a primary glaucoma, a developmental glaucoma, a secondary glaucoma and absolute glaucoma. In an exemplary embodiment, glaucoma is selected from the group consisting of primary open-angle glaucoma (chronic open-angle glaucoma, chronic simple glaucoma or glaucoma simplex), low-tension glaucoma or primary angle-closure glaucoma (primary closed-angle glaucoma, narrow-angle glaucoma, pupil-block glaucoma or acute congestive glaucoma). In an exemplary embodiment, the glaucoma is selected from the group consisting of an acute angle-closure glaucoma or chronic angle-closure glaucoma or intermittent angle-closure glaucoma. In an exemplary embodiment, the developmental glaucoma is selected from the group consisting of primary congenital glaucoma or infantile glaucoma or hereditary glaucoma. In an exemplary embodiment, the secondary glaucoma is selected from the group consisting of inflammatory glaucoma, phacogenic glaucoma, glaucoma secondary to intraocular hemorrhage, traumatic glaucoma, neovascular glaucoma, drug-induced glaucoma and toxic glaucoma. In an exemplary embodiment, the drug-induced glaucoma is corticosteroid induced glaucoma. In an exemplary embodiment, the glaucoma is pigmentary glaucoma or exfoliation glaucoma. In an exemplary embodiment, the glaucoma is inflammatory glaucoma, and said inflammatory glaucoma is uveitis or Fuchs heterochromic iridocyclitis.

In an exemplary embodiment, the invention provides a method of treating pulmonary hypertension, comprising administering to an animal in need of treatment a therapeutically effective amount of a compound of the invention, thereby treating pulmonary hypertension. In an exemplary embodiment, the invention provides a method of treating pulmonary hypertension, comprising administering to an animal in need of treatment a therapeutically effective amount of a compound described herein, thereby treating pulmonary hypertension.

In an exemplary embodiment, the invention provides a method of treating glaucoma, comprising administering to an animal in need of treatment a therapeutically effective amount of a compound of the invention, thereby treating glaucoma. In an exemplary embodiment, the invention provides a method of treating glaucoma, comprising administering to an animal in need of treatment a therapeutically effective amount of a compound described herein, thereby treating glaucoma.

In an exemplary embodiment, the invention provides a method of preventing glaucoma, comprising administering to an animal in need of treatment a therapeutically effective amount of a compound of the invention, thereby preventing glaucoma. In an exemplary embodiment, the invention provides a method of preventing glaucoma, comprising administering to an animal in need of treatment a therapeutically effective amount of a compound described herein, thereby preventing glaucoma.

In an exemplary embodiment, the invention provides a method of reducing intra-ocular pressure, comprising administering to an animal in need of treatment a therapeutically effective amount of a compound of the invention, thereby reducing said intra-ocular pressure. In an exemplary embodiment, the invention provides a method of reducing intra-ocular pressure, comprising administering to an animal in need of treatment a therapeutically effective amount of a compound described herein, thereby reducing said intra-ocular pressure.

In an exemplary embodiment, the invention provides a method of treating and/or preventing ocular nerve neuropathy, comprising administering to an animal in need of treatment a therapeutically effective amount of a compound of the invention, thereby treating and/or preventing ocular nerve neuropathy. In an exemplary embodiment, the invention provides a method of treating and/or preventing ocular nerve neuropathy, comprising administering to an animal in need of treatment a therapeutically effective amount of a compound described herein, thereby treating and/or preventing ocular nerve neuropathy.

In an exemplary embodiment, the invention provides a method of reducing blood pressure, comprising administering to an animal in need of treatment a therapeutically effective amount of a compound of the invention, thereby reducing the blood pressure. In an exemplary embodiment, the invention provides a method of reducing blood pressure, comprising administering to an animal in need of treatment a therapeutically effective amount of a compound of the invention, thereby reducing the blood pressure.

In an exemplary embodiment, for any of the methods described herein, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, for any of the methods described herein, the animal is a member selected from a human, cattle, goat, pig, sheep, horse, cow, bull, dog, guinea pig, gerbil, rabbit, cat, chicken and turkey. In another exemplary embodiment, for any of the methods described herein, the animal is a human.

In an exemplary embodiment, for any of the methods described herein, a compound of the invention and/or a pharmaceutical formulation described herein can be used.

In another exemplary embodiment, in any of the methods of treating/preventing a condition or enhancing an effect described herein, the animal being administered the compound of the invention is not otherwise in need of treatment with the compound of the invention.

In another exemplary embodiment, the condition is glaucoma, and the animal being administered the compound of the invention is not otherwise in need of treatment with the compound of the invention.

In another exemplary embodiment, the condition is pulmonary hypertension, and the animal being administered the compound of the invention is not otherwise in need of treatment with the compound of the invention.

In another exemplary embodiment, in any of the methods of treating/preventing a condition or enhancing an effect described herein, the animal being administered the compound of the invention is not otherwise in need of treatment with a compound of the invention.

V. Pharmaceutical Formulations

In another aspect, the invention provides a pharmaceutical formulation comprising: (a) a compound of the invention; and (b) a pharmaceutically acceptable excipient.

Information regarding excipients of use in the formulations of the invention can be found in *Remington: The Science and Practice of Pharmacy*, 21st Ed., Pharmaceutical Press (2011) which is incorporated herein by reference.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention.

Exemplary embodiments are summarized herein below.

In an exemplary embodiment, the invention provides a compound having a structure according to the following formula:

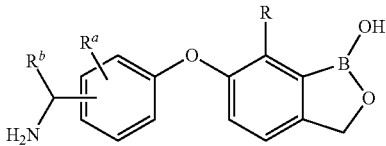

wherein $R^a$ is halogen, $R^b$ is H or unsubstituted $C_1$-$C_4$ alkyl, when $R^b$ is unsubstituted $C_1$-$C_4$ alkyl, then R is H or halogen or unsubstituted $C_1$-$C_4$ alkyl, when $R^b$ is H, then R is halogen or unsubstituted $C_1$-$C_4$ alkyl, or a salt thereof.

In an exemplary embodiment, according to the above paragraph, the compound, or a salt thereof, has a structure according to the following formula:

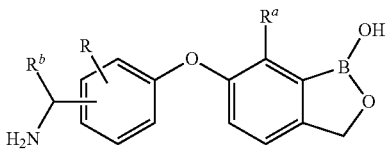

wherein $R^a$ is halogen, $R^b$ is unsubstituted $C_1$-$C_4$ alkyl, R is H or halogen or unsubstituted $C_1$-$C_4$ alkyl.

In an exemplary embodiment, according to any of the above paragraphs, the compound, or a salt thereof, which has a structure which is:

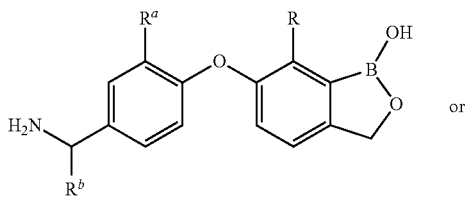

or

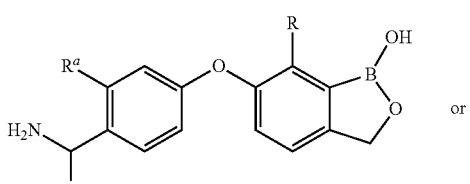

or

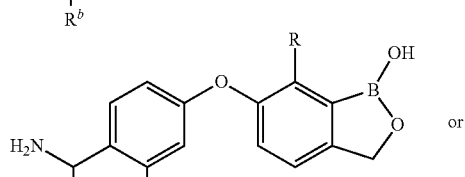

or

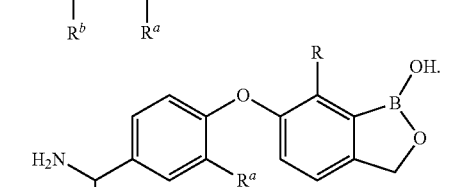

In an exemplary embodiment, according to any of the above paragraphs, the compound, or a salt thereof, which has a structure which is:

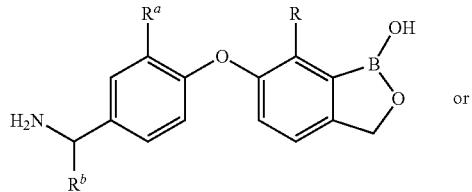

or

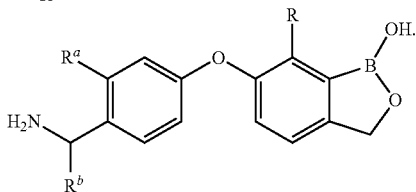

In an exemplary embodiment, according to any of the above paragraphs, the compound, or a salt thereof, in which R is F, Cl, methyl, ethyl, or isopropyl.

In an exemplary embodiment, according to any of the above paragraphs, the compound, or a salt thereof, in which $R^a$ is F or Cl.

In an exemplary embodiment, according to any of the above paragraphs, the compound, or a salt thereof, in which $R^b$ is methyl.

In an exemplary embodiment, according to any of the above paragraphs, the compound, or a salt thereof, in which $R^a$ is F or Cl, and $R^b$ is methyl.

In an exemplary embodiment, according to any of the above paragraphs, the compound, or a salt thereof, in which $R^a$ is Cl and $R^b$ is methyl.

In an exemplary embodiment, according to any of the above paragraphs, the compound, or a salt thereof, in which $R^a$ is F or Cl, $R^b$ is methyl, R is methyl.

In an exemplary embodiment, according to any of the above paragraphs, the compound, or a salt thereof, in which $R^a$ is F or Cl, $R^b$ is methyl, R is ethyl.

In an exemplary embodiment, according to any of the above paragraphs, the compound, or a salt thereof, in which $R^a$ is F or Cl, $R^b$ is methyl, R is isopropyl.

In an exemplary embodiment, the invention provides a combination comprising the compound according to any of the above paragraphs, together with at least one other therapeutically active agent.

In an exemplary embodiment, the invention provides a pharmaceutical formulation comprising: a) the compound according to any of the above paragraphs, or a salt thereof; and b) a pharmaceutically acceptable excipient.

In an exemplary embodiment, according to any of the above paragraphs, the pharmaceutical formulation is a unit dosage form.

In an exemplary embodiment, according to any of the above paragraphs, the salt of the compound according to any of the above paragraphs is a pharmaceutically acceptable salt.

In an exemplary embodiment, the invention is a method of treating and/or preventing a disease, comprising administering to an animal in need of treatment a therapeutically effective amount of a boron-containing compound in any of the above paragraphs, thereby treating the disease.

In an exemplary embodiment, according to the above method paragraph, the disease implicates a kinase.

In an exemplary embodiment, according to any of the above method paragraphs, the disease is caused by the overexpression, underexpression or malfunction of said kinase.

In an exemplary embodiment, according to any of the above method paragraphs, the disease is glaucoma, and glaucoma is a member selected from a primary glaucoma, a developmental glaucoma, a secondary glaucoma and absolute glaucoma.

In an exemplary embodiment, according to any of the above method paragraphs, the disease is glaucoma, and glaucoma is a member selected from primary open-angle glaucoma (chronic open-angle glaucoma, chronic simple glaucoma or glaucoma simplex), low-tension glaucoma or primary angle-closure glaucoma (primary closed-angle glaucoma, narrow-angle glaucoma, pupil-block glaucoma or acute congestive glaucoma).

In an exemplary embodiment, according to any of the above method paragraphs, the disease is glaucoma, and glaucoma is a member selected from acute angle-closure glaucoma or chronic angle-closure glaucoma or intermittent angle-closure glaucoma.

In an exemplary embodiment, according to any of the above method paragraphs, the disease is developmental glaucoma, and said developmental glaucoma is a member selected from primary congenital glaucoma or infantile glaucoma or hereditary glaucoma.

In an exemplary embodiment, according to any of the above method paragraphs, the disease is secondary glaucoma, and said secondary glaucoma is a member selected from inflammatory glaucoma or phacogenic glaucoma or glaucoma secondary to intraocular hemorrhage or traumatic glaucoma or neovascular glaucoma or drug-induced glaucoma or toxic glaucoma.

In an exemplary embodiment, according to any of the above method paragraphs, the disease is secondary glaucoma, and said drug-induced glaucoma is a member selected from corticosteroid induced glaucoma.

In an exemplary embodiment, according to any of the above method paragraphs, the disease is glaucoma, and glaucoma is a member selected from pigmentary glaucoma or exfoliation glaucoma.

In an exemplary embodiment, according to any of the above method paragraphs, the disease is inflammatory glaucoma, and said inflammatory glaucoma is a member selected from uveitis or Fuchs heterochromic iridocyclitis.

In an exemplary embodiment, according to any of the above method paragraphs, the disease is pulmonary hypertension.

In an exemplary embodiment, according to any of the above method paragraphs, the animal is a human.

In an exemplary embodiment, according to any of the above method paragraphs, there is a proviso that the animal is not otherwise in need of treatment with a compound of the invention.

The invention is further illustrated by the Examples that follow. The Examples are not intended to define or limit the scope of the invention.

EXAMPLES

Proton NMR are recorded on Varian AS 300 (300 MHz) or AS400 (400 MHz) spectrometer and chemical shifts are reported as δ (ppm) down field from tetramethylsilane. Mass spectra are determined on Micromass Quattro II or Waters MS consisting of an Alliance 2795 (LC) and Waters Micromass ZQ detector at 120° C. The mass spectrometer was equipped with an electrospray ion source (ES) operated in a positive or negative mode.

All solvents used were commercially available and were used without further purification. Reactions were typically run using anhydrous solvents under an inert atmosphere of nitrogen.

$^1$H and $^{13}$C NMR spectra were recorded at 400 MHz for proton and 100 MHz for carbon-13 on a Varian 300 MercuryPlus station with an Oxford AS400 Spectrometer equipped with a Varian 400 ATB PFG probe. All deuterated solvents contained typically 0.03% to 0.05% v/v tetramethylsilane, which was used as the reference signal (set at δ 0.00 for both $^1$H and $^{13}$C).

Compounds are named using ChemDraw7.0, or using their catalogue name if commercially available.

HPLC analyses were performed on a Water 600 Controller system with a Waters 717 Plus Autosampler and a Waters 2996 Photodiode Array Detector. The column used was an ACE $C_{18}$, 5 μm, 4.6×150 mm. A linear gradient was applied, starting at 95% A (A: 0.1% $H_3PO_4$ in water) and ending at 90% B (B: MeCN) over 6 min and then maintained at 90% B until the 10 min mark. The column is then re-equilibrated over 3 min to 95:5 with a total run time of 20 min. The column temperature was at ambient temperature with the flow rate of 1.0 mL/min. The Diode Array Detector was scanned from 200-400 nm.

Thin layer chromatography (TLC) was performed on Alugram® (Silica gel 60 $F_{254}$) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), vanillin (generated by dissolving about 1 g vanillin in 100 mL 10% $H_2SO_4$), ninhydrin (available commercially from Aldrich), or Magic Stain (generated by thoroughly mixing 25 g $(NH_4)_6Mo_7O_{24}.4H_2O$, 5 g $(NH_4)_2Ce(IV)(NO_3)_6$ in 450 mL water and 50 mL concentrated $H_2SO_4$) to visualize the compound. Flash chromatography was preformed using typically 40-63 μm (230-400 mesh) silica gel from Silicycle following analogous techniques to those disclosed in Still, W. C.; Kahn, M.; and Mitra, M. Journal of Organic Chemistry, 1978, 43, 2923-2925. Typical solvents used for flash chromatography or thin layer chromatography were mixtures of chloroform/methanol, dichloromethane/methanol, ethyl acetate/methanol and hexanes/ethyl acetate. Reverse phase column chromatography were performed on a Biotage® using a Biotage $C_{18}$ cartridges and a water/methanol gradient (typically eluting from 5% MeOH/$H_2O$ to 90% MeOH/$H_2O$).

Preparative chromatography was performed on either a Waters Prep LC 4000 System using a Waters 2487 Diode Array or on a Waters LC Module 1 plus. The column used was a Waters XTerra Prep $C_{18}$, 5 μm, 30×100 mm or Phenomenex Luna $C_{18}$, 5 μm, 21.6×250 mm or Phenomenex Gemini $C_{18}$, 5 μm, 100×30 mm. Narrow gradients with acetonitrile/water, with the water containing either 0.1% trifluoroacetic acid or 0.1% acetic acid, were used to elute the compound at a flow rate of approximately 20 mL/min and a total run time between 20-30 min.

Example 1

Example 1

6-(4-(Aminomethyl)-2-chlorophenoxy)-7-ethylbenzo[c][1,2]oxaborol-1(3H)-ol (A)

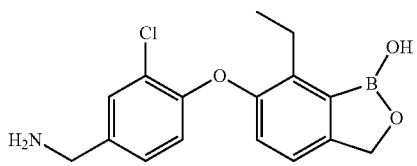 [SMILES: CCc1c(Oc2ccc(CN)cc2Cl)ccc2c1B(O)OC2]

Preparation of 2-ethylbenzene-1,3-diol

To a mixture of 1-(2,6-dihydroxyphenyl)ethan-1-one (20.0 g, 0.130 mol) in TFA (650 mL) was added Et$_3$SiH (33.6 g, 0.29 mol) dropwise at 0° C., the resulting solution was then stirred at room temperature for 3 h. Water was added and the product was extracted with ether. The residue was recrystallized with DCM/n-hexane to give 2-ethylbenzene-1,3-diol as light yellow solid (10.0 g, 56%).

$^1$H NMR (400 MHz CDCl$_3$) δ 6.931-6.891 (t, 1H), 6.391-6.371 (d, 2H), 4.678 (s, 2H), 2.690-2.633 (m, 2H), 1.212-1.153 (m, 3H).

Preparation of 3-ethyl-2,4-dihydroxybenzaldehyde

DMF (126 mL) was placed in a flask followed by addition of POCl$_3$ (84 g, 0.54 mol) dropwise at 0° C. The mixture was stirred at −5° C. for 30 min followed by addition of a solution of compound 2 (25 g, 0.18 mol) in DMF (117 mL). After 3.5 h, the reaction mixture was poured into 2M NaOH, and extracted with EtOAc. The remained aqueous solution was neutralized with 5M HCl to pH 5, extracted with EtOAc, and organic phase was concentrated and purified by column chromatography to give 3-ethyl-2,4-dihydroxybenzaldehyde as brown solid (25 g, 83%).

$^1$H NMR (400 MHz CDCl$_3$) δ 11.621 (s, 1H), 10.771 (s, 1H), 9.697 (s, 1H), 7.441-7.420 (d, 1H), 6.567-6.546 (d, 1H), 2.553-2.504 (m, 2H), 1.054-1.016 (t, 3H).

Preparation of 3-chloro-4-(2-ethyl-4-formyl-3-hydroxyphenoxy)benzonitrile

To a mixture of 3-ethyl-2,4-dihydroxybenzaldehyde (25 g, 150.5 mmol) and 3-chloro-4-fluorobenzonitrile (23.4 g, 150.5 mol) in DMF (300 ml) was added Cs$_2$CO$_3$ (59 g, 180.6 mmol). The mixture was heated at 130° C. for 6 h. After cool down to room temperature, a mixture of EtOAc and water was added. After stirring for 20 min, the organic layer was separated and aqueous layer was extracted with more EtOAc. The combined organic layers were washed with brine, dried over Na$_2$SO$_4$, concentrated and the residue was purified by chromatography to give 3-chloro-4-(2-ethyl-4-formyl-3-hydroxyphenoxy)benzonitrile as light yellow solid (24 g, 53%).

$^1$H NMR (400 MHz CDCl$_3$) δ 11.626 (s, 1H), 9.842 (s, 1H), 7.830-7.825 (d, 1H), 7.583-7.556 (m, 1H), 7.423-7.402 (d, 1H), 7.036-7.015 (d, 1H), 6.410-6.389 (d, 1H), 2.773-2.754 (m, 2H), 1.221-1.198 (t, 3H).

Preparation of 3-(2-chloro-4-cyanophenoxy)-2-ethyl-6-formylphenyl trifluoromethanesulfonate To a mixture of 3-chloro-4-(2-ethyl-4-formyl-3-hydroxyphenoxy)benzonitrile (35 g, 116.22 mmol) and pyridine (45.2 g, 581 mmol) in DCM (600 mL) at 0° C. was slowly added Tf$_2$O (82 g, 290.6 mmol). The reaction mixture was stirred for 3 h and diluted with DCM, washed with aq. NH$_4$Cl solution twice, the organic solution was dried (Na$_2$SO$_4$) and concentrated. The crude product was purified by chromatography to give 3-(2-chloro-4-cyanophenoxy)-2-ethyl-6-formylphenyl trifluoromethanesulfonate (38 g, 76%).

$^1$H NMR (400 MHz CDCl$_3$) δ 10.106 (s, 1H), 7.783-7.762 (m, 2H), 7.572-7.546 (m, 1H), 7.073-7.052 (d, 1H), 6.731-6.709 (d, 1H), 2.881-2.824 (m, 2H), 1.253-1.216 (t, 3H).

Preparation of 3-chloro-4-(2-ethyl-4-formyl-3-(4,4,5,5-tetramethyl-1,3,2-dioxaborolan-2-yl)phenoxy)benzonitrile A mixture of 3-(2-chloro-4-cyanophenoxy)-2-ethyl-6-formylphenyl trifluoromethanesulfonate (5.00 g, 11.5 mmol) in 1,4-dioxane was bubbled with nitrogen gas for 30 min and to this mixture was added Pin$_2$B$_2$ (9.00 g, 34.5 mmol), KOAc (2.2 g, 23 mmol) and Pd(dppf)Cl$_2$ (0.4 g, 0.6 mmol) in one portion. The mixture was degassed twice then stirred at 90° C. overnight under nitrogen protection. After the reaction was completed, the mixture was filtered and the crude product was purified by silica gel column chromatography. Twelve parallel reactions were operated and a total of 37 g of 3-chloro-4-(2-ethyl-4-formyl-3-(4,4,5,5-tetramethyl-1,3,2-dioxaborolan-2-yl)phenoxy)benzonitrile was obtained (67%).

$^1$H NMR (400 MHz CDCl$_3$) δ 9.91 (s, 1H), 7.80 (s, 1H), 7.65 (d, 1H, J=8.0 Hz), 7.51 (d, 1H, J=8.0 Hz), 6.90 (d, 1H, J=8.0 Hz), 2.75 (t, 2H, J=7.2 Hz), 1.49 (s, 12H), 1.25 (t, 3H, J=7.2 Hz).

Preparation of Compound 8

To a solution of 3-chloro-4-(2-ethyl-4-formyl-3-(4,4,5,5-tetramethyl-1,3,2-dioxaborolan-2-yl)phenoxy)benzonitrile (18.0 g, 43.8 mmol) in THF (200 mL) was added NaBH$_4$ (5.00 g, 131 mmol) in one portion at ice-water bath. Then 5 mL of methanol was added dropwise to the mixture, the resulting mixture was stirred at room temperature for 30 min, TLC showed the reaction was completed. The mixture was adjusted to pH 2 with 12M HCl and then poured into cold water, extracted three times with EtOAc, the organic layers were combined and washed with brine, dried over Na$_2$SO$_4$ and concentrated to give 3-chloro-4-((7-ethyl-1-hydroxy-1,3-dihydrobenzo[c][1,2]oxaborol-6-yl)oxy)benzonitrile as white solid (8.6 g, 63%)

$^1$H NMR (400 MHz CDCl$_3$) δ 7.73 (s, 1H), 7.37 (d, 1H, J=8.0 Hz), 7.36 (s, 1H), 7.17 (d, 1H, J=8.0 Hz), 7.07 (d, 1H, J=8.0 Hz), 6.64 (d, 1H, J=8.0 Hz), 5.04 (s, 2H), 2.70 (q, 2H), 1.10 (t, 3H).

Preparation of A

The mixture of 3-chloro-4-((7-ethyl-1-hydroxy-1,3-dihydrobenzo[c][1,2]oxaborol-6-yl)oxy)benzonitrile (31 g, 100 mmol) in anhydrous THF (500 mL) was a solution of borane-THF complex solution (500 mL, 0.5 mol) at 0° C., the mixture was stirred at room temperature overnight and HPLC showed most starting material consumed. 2M HCl (50 mL) was added to adjust the pH to 4, the mixture was concentrated and the residue was purified by preparative HPLC (column: luna 300×50 mm, liquid phase: [A—H₂O+ 0.05% HCl; B—MeCN] B %: 10%-40%, 25 min), the solvent was concentrated to give A as white solid (16.7 g, 48%)

¹H NMR (400 MHz DMSO-d₆) δ 9.09 (s, 1H), 8.42 (s, 3H), 7.78 (s, 1H), 7.38 (d, 1H, J=8.0 Hz), 7.27 (d, 1H, J=8.0 Hz), 6.98 (d, 1H, J=8.0 Hz), 6.77 (d, 1H, J=8.0 Hz), 4.98 (s, 2H), 4.00 (s, 2H), 2.75 (m, 2H), 1.10 (t, 3H); ESI-MS (m/z): 301 (M−NH₂)⁺

Example 2

6-(4-(aminomethyl)-2-chlorophenoxy)-7-chlorobenzo[c][1,2]oxaborol-1(3H)-ol (B)

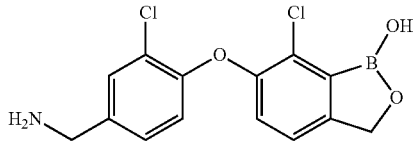

Preparation of 7-chlorobenzo[c][1,2]oxaborole-1,6(3H)-diol

To a solution of benzo[c][1,2]oxaborole-1,6(3H)-diol (15 g, 0.1 mol) in DMF/DCM (500 mL, 1:10) was added N-chlorosuccinimide (19.5 g, 0.11 mol) and stirred at 30° C. overnight. The precipitates were filtered and dried to give 7-chlorobenzo[c][1,2]oxaborole-1,6(3H)-diol.

¹H NMR (400 MHz DMSO-d₆) δ 9.93 (1H, s), 8.99 (1H, s), 7.15-7.07 (2H, m), 4.88 (1H, s).

Preparation of 3-chloro-4-((7-chloro-1-hydroxy-1,3-dihydrobenzo[c][1,2]oxaborol-6-yl)oxy)benzonitrile To a solution of 7-chlorobenzo[c][1,2]oxaborole-1,6(3H)-diol (1.86 g, 12 mmol) in DMF (20 mL) were added 3-chloro-4-fluorobenzonitrile (1.85 g, 10 mmol) and K₂CO₃, then stirred at 70° C. overnight. The mixture was then poured into H₂O (200 mL), acidified by HCl to pH=5. After extracting with EtOAc and concentration, crude 3-chloro-4-((7-chloro-1-hydroxy-1,3-dihydrobenzo[c][1,2]oxaborol-6-yl)oxy)benzonitrile was obtained.

¹H NMR (400 MHz DMSO-d₆) δ 7.97 (1H, d), 7.62 (1H, s), 7.42 (1H, d), 7.21 (1H, d), 6.80 (1H, d), 4.89 (1H, s).

Preparation of B

To a solution of 3-chloro-4-((7-chloro-1-hydroxy-1,3-dihydrobenzo[c][1,2]oxaborol-6-yl)oxy)benzonitrile (0.95 g, 3 mmol) in THF (50 mL) was added BH₃ solution in THF (1M, 30 mL, 30 mmol), then stirred at 40° C. overnight. After the reaction was completed, it was quenched with HCl, concentrated and purified by pre-HPLC to give B (200 mg).

¹H NMR (400 MHz DMSO-d₆) δ 9.32 (1H, s), 8.50 (3H, s), 7.81 (1H, s), 7.44 (2H, t), 7.22 (1H, d), 6.80 (1H, d), 5.02 (2H, s), 4.01 (2H, s); ESI-MS (m/z): 307 (M−NH₂)⁺

Example 3

6-(4-(1-aminoethyl)-2-fluorophenoxy)benzo[c][1,2]oxaborol-1(3H)-ol (C)

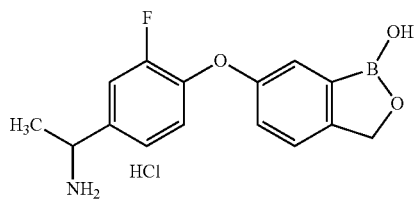 [SMILES: CC(N)c1ccc(Oc2ccc3c(c2)B(O)OC3)c(F)c1 ; Cl]

Preparation of (E)-1-(3-fluoro-4-hydroxyphenyl)ethan-1-one oxime

To a solution of 1-(3-fluoro-4-hydroxyphenyl)ethan-1-one (500 mg, 3.24 mmol) in ethanol (5 mL) was added a mixture of hydroxylamine hydrochloride (675 mg, 9.72 mmol) and NaHCO₃ (408 mg, 4.86 mmol) in water (5 mL). The reaction mixture was heated under reflux for 4 h, cooled to rt and concentrated under reduced pressure. The residue was diluted with EtOAc, washed with water, dried over MgSO₄ and filtered. The solvent was removed under reduced pressure to give (E)-1-(3-fluoro-4-hydroxyphenyl)ethan-1-one oxime (550 mg, 100%) as a yellow solid.

¹H NMR (400 MHz, CDCl₃) δ 7.50-7.67 (m, 2H), 7.07 (t, J=8.4 Hz, 1H), 6.23 (s, 1H), 2.56 (s, 3H).

Preparation of 4-(1-aminoethyl)-2-fluorophenol

A mixture of (E)-1-(3-fluoro-4-hydroxyphenyl)ethan-1-one oxime (546 mg, 3.23 mmol) and Pd—C (10%, 300 mg) in AcOH (8 mL) was stirred under a H₂ atmosphere (1 atm) at rt for 16 h. The mixture was filtered, washed with AcOH and concentrated under reduced pressure. The residue was dissolved in water, washed with EtOAc, cooled to 0° C. and basified with 20% NaOH to pH of 10. The mixture was filtered, washed with cold water and dried to give 4-(1-aminoethyl)-2-fluorophenol (298 mg, 60%) as a pink solid.

¹H NMR (400 MHz, DMSO-d₆) δ 7.10 (d, J=8.8 Hz, 1H), 6.92 (d, J=9.2 Hz, 1H), 6.82 (t, J=8.4 Hz, 1H), 3.85 (m, 1H), 1.17 (d, J=7.6 Hz, 3H).

Preparation of tert-butyl (1-(3-fluoro-4-hydroxyphenyl)ethyl)carbamate

To a solution of 4-(1-aminoethyl)-2-fluorophenol (190 mg, 1.22 mmol) and triethylamine (0.51 ml, 3.67 mmol) in THF (10 mL) at room temperature was added (Boc)₂O (0.34 mL, 1.46 mmol). The reaction mixture was stirred for 16 h and concentrated under reduced pressure. The residue was purified by column chromatography on silica gel, eluting with EtOAc-Petroleum Ether (1:10) to afford tert-butyl (1-(3-fluoro-4-hydroxyphenyl)ethyl)carbamate (245 mg, 79%) as a colorless oil.

¹H NMR (400 MHz, CDCl₃) δ 7.07-7.15 (m, 3H), 4.76 (s, 1H), 1.54-1.57 (m, 12H).

Preparation of tert-butyl (1-(4-(3-bromo-4-formylphenoxy)-3-fluorophenyl)ethyl)carbamate To a solution of tert-butyl (1-(3-fluoro-4-hydroxyphenyl)ethyl)carbamate (200 mg, 0.78 mmol) in DMSO (5 mL) at room temperature was added t-BuOK (105 mg, 0.94 mmol). After 5 min, 2-bromo-4-fluorobenzaldehyde (191 mg, 0.94 mmol) was added and the reaction mixture was heated at 70° C. for 3 h. The mixture was cooled to room temperature and diluted with EtOAc (10 mL). The organic layer was washed with water, dried with MgSO$_4$ and filtered. The solvent was removed under reduced pressure and the crude product was purified by column chromatography on silica gel, eluting with EtOAc-Petroleum Ether (1:20 to 1:10) to afford tert-butyl (1-(4-(3-bromo-4-formylphenoxy)-3-fluorophenyl)ethyl)carbamate (170 mg, 50%) as a white solid.

$^1$H NMR (400 MHz, CDCl$_3$) δ: 10.24 (s, 1H), 7.89 (d, J=8.8 Hz, 1H), 7.12-7.19 (m, 4H), 6.96 (dd, J=8.4 Hz, 2.4 Hz, 1H), 4.81 (s, 1H), 1.44-1.47 (s, 12H).

Preparation of tert-butyl (1-(3-fluoro-4-(4-formyl-3-(4,4,5,5-tetramethyl-1,3,2-dioxaborolan-2-yl)phenoxy)phenyl)ethyl)carbamate A solution of tert-butyl (1-(4-(3-bromo-4-formylphenoxy)-3-fluorophenyl)ethyl)carbamate (160 mg, 0.37 mmol), bis(pinacolato)diboron (185 mg, 0.73 mmol), Pd(dppf)Cl$_2$ (54 mg, 0.074 mmol) and KOAc (109 mg, 1.11 mmol) in 1,4-dioxane (4 mL) was bubbled with argon for 30 min and heated at 100° C. for 3 h. The mixture was cooled to rt and filtered. The solvent was removed under reduced pressure. The residue was purified by column chromatography on silica gel, eluting with EtOAc-Petroleum Ether (1:30 to 1:5) to afford tert-butyl (1-(3-fluoro-4-(4-formyl-3-(4,4,5,5-tetramethyl-1,3,2-dioxaborolan-2-yl)phenoxy)phenyl)ethyl)carbamate (62 mg; 35%) as a white solid.

$^1$H NMR (400 MHz, CDCl$_3$) δ 10.40 (s, 1H), 7.92 (d, J=8.4 Hz, 1H,), 7.45 (d, J=2.4 Hz, 1H), 7.05-7.14 (m, 3H), 6.95 (dd, J=8.4 Hz, 2.0 Hz, 1H), 4.47 (s, 1H), 1.38-1.44 (m, 24H).

Preparation of C

To a solution of tert-butyl (1-(3-fluoro-4-(4-formyl-3-(4,4,5,5-tetramethyl-1,3,2-dioxaborolan-2-yl)phenoxy)phenyl)ethyl)carbamate (50 mg, 0.10 mmol) in MeOH (2 mL) was slowly added NaBH$_4$ (12 mg, 0.31 mmol). The reaction mixture was stirred for 2 h and treated with 1M HCl (1.3 mL). The mixture was stirred at 30° C. for 16 h, filtered and concentrated under reduced pressure to give C (30 mg) as a white solid.

$^1$H NMR (400 MHz, DMSO-d$_6$) δ 9.20 (s, 1H), 8.60 (s, 3H), 7.64 (d, J=12.4 Hz, 1H), 7.43 (t, J=6.0 Hz, 1H), 7.37 (d, J=8.0 Hz, 1H), 7.27 (s, 1H), 7.16-7.22 (m, 2H), 4.97 (s, 2H), 4.45 (m, 1H), 1.54 (d, J=6.8 Hz, 3H).

Example 4

6-(4-(aminomethyl)-2-fluorophenoxy)-7-methyl-benzo[c][1,2]oxaborol-1(3H)-ol (D)

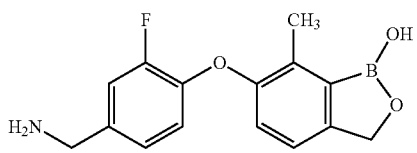 [SMILES: Cc1c(Oc2ccc(CN)cc2F)ccc2c1B(O)OC2]

Preparation of 3-fluoro-4-(4-formyl-3-hydroxy-2-methylphenoxy)benzonitrile

To a solution of 2,4-dihydroxy-3-methylbenzaldehyde (5.78 g, 37.96 mmol) in DMSO (90 mL) was added t-BuOK (4.26 g, 37.96 mmol). After 5 min, 3,4-difluorobenzonitrile (4.40 g, 31.63 mmol) was added and the reaction mixture was heated at 70° C. for 4 h. The mixture was cooled to room temperature, diluted with EtOAc (100 mL) and neutralized with 1M HCl (40 mL) to pH 7. The organic layer was separated, washed with water, dried with MgSO$_4$ and filtered. The solvent was removed under reduced pressure and the crude product was purified by column chromatography on silica gel, eluting with Petroleum Ether-DCM (4:1 to 3:2) to give 3-fluoro-4-(4-formyl-3-hydroxy-2-methylphenoxy)benzonitrile (1.23 g, 14%) as a white solid.

$^1$H NMR (400 MHz, CDCl$_3$) δ 11.42 (s, 1H), 8.13 (dd, J=6.4 Hz, 2.0 Hz, 1H), 7.75 (d, J=8.8 Hz, 1H), 7.66 (d, J=8.4 Hz, 1H), 7.29 (t, J=8.8 Hz, 1H), 6.59 (d, J=8.4 Hz, 1H), 2.12 (s, 3H).

Preparation of 3-(4-cyano-2-fluorophenoxy)-6-formyl-2-methylphenyl trifluoromethanesulfonate To a mixture of 3-fluoro-4-(4-formyl-3-hydroxy-2-methylphenoxy)benzonitrile (500 mg, 1.84 mmol) and pyridine (0.70 ml, 9.2 mmol) in DCM (5 mL) at 0° C. was slowly added a solution Tf$_2$O (0.7 ml, 4.6 mmol) in DCM (3 mL). The reaction mixture was stirred for 30 min and diluted with EtOAc (10 mL). The organic solution was washed with 1M HCl (10 mL×3), dried over MgSO$_4$, filtered and concentrated under reduced pressure. The residue was purified by column chromatography on silica gel, eluting with Petroleum Ether-EtOAc (95:5) to give 3-(4-cyano-2-fluorophenoxy)-6-formyl-2-methylphenyl trifluoromethanesulfonate (585 mg, 78%) as a white solid.

$^1$H NMR (400 MHz, CDCl$_3$) δ 10.17 (s, 1H), 7.84 (d, J=8.8 Hz, 1H), 7.52-7.58 (m, 2H), 7.21 (d, J=8.0 Hz, 1H), 6.87 (d, J=8.4 Hz, 1H), 2.44 (s, 1H).

Preparation of 3-fluoro-4-(4-formyl-2-methyl-3-(4,4,5,5-tetramethyl-1,3,2-dioxaborolan-2-yl)phenoxy)benzonitrile A mixture of 3-(4-cyano-2-fluorophenoxy)-6-formyl-2-methylphenyl trifluoromethanesulfonate (585 mg, 1.45 mmol), bis(pinacolato)diboron (736 mg, 2.89 mmol), Pd (dppf)Cl$_2$ (212 mg, 0.29 mmol) and KOAc (427 mg, 4.32 mmol) in 1,4-dioxane (15 mL) was stirred at rt for 30 min and heated at 100° C. for 3 h. The mixture was cooled to room temperature and filtered. The solvent was removed under reduced pressure and the residue was purified by column chromatography on silica gel, eluting with Petroleum Ether-DCM (4:1 to 1:1) to afford 3-fluoro-4-(4-formyl-2-methyl-3-(4,4,5,5-tetramethyl-1,3,2-dioxaborolan-2-yl)phenoxy)benzonitrile (300 mg, 54%) as a white solid.

$^1$H NMR (400 MHz, CDCl$_3$) δ 9.88 (s, 1H), 7.61 (d, J=8.4 Hz, 1H), 7.47 (dd, J=10.0 Hz, 2.0 Hz, 1H,), 9.37 (dd, J=8.8 Hz, 1.2 Hz, 1H), 6.86-6.98 (m, 2H), 2.34 (s, 3H), 1.45 (s, 12H).

Preparation of 3-fluoro-4-((1-hydroxy-7-methyl-1,3-dihydrobenzo[c][1,2]oxaborol-6-yl)oxy)benzonitrile To a solution of 3-fluoro-4-(4-formyl-2-methyl-3-(4,4,5,5-tetramethyl-1,3,2-dioxaborolan-2-yl)phenoxy)benzonitrile (150 mg, 0.39 mmol) in methanol (5 mL) at room temperature was slowly added NaBH$_4$ (44 mg, 1.17 mmol). The reaction mixture was stirred for 2 h and to it was slowly added 1M HCl (1 mL). The reaction mixture was stirred at room temperature for 16 h and concentrated under reduced pressure. The residue was washed with water and dried to afford 3-fluoro-4-((1-hydroxy-7-methyl-1,3-dihydrobenzo[c][1,2]oxaborol-6-yl)oxy)benzonitrile (74 mg, 64%) as a white solid.

$^1$H NMR (400 MHz, DMSO-d$_6$) δ 9.14 (s, 1H), 8.04 (d, J=10.8 Hz, 1H), 7.58 (d, J=8.0 Hz, 1H), 7.31 (d, J=8.8 Hz, 1H), 7.20 (d, J=8.0 Hz, 1H), 6.77 (t, J=8.8 Hz, 1H), 4.98 (s, 2H), 2.26 (s, 3H).

Preparation of E

To a solution of LiAlH$_4$ (117 mg, 3.08 mmol) in THF (10 mL) at 0° C. was slowly added a solution of 3-fluoro-4-((1-hydroxy-7-methyl-1,3-dihydrobenzo[c][1,2]oxaborol-6-yl)oxy) benzonitrile (349 mg, 1.23 mmol) in THF (5 mL). The reaction mixture was stirred for 2 h and quenched with 1M HCl (5 mL) and water (10 mL). The mixture was stirred for 1 h, filtered, and concentrated under reduced pressure. The residue was washed with EtOAc and methanol, and dried to give E (150 mg, 42%) as a white solid.

$^1$H NMR (400 MHz, DMSO-d$_6$) δ 9.11 (d, 1H), 8.35 (s, 3H), 7.56 (d, J=8.4 Hz, 1H), 7.24 (m, 2H), 7.00 (d, J=8.0 Hz, 1H), 6.84 (d, J=8.0 Hz, 1H), 4.96 (s, 2H), 4.00 (s, 2H), 2.32 (s, 3H).

Example 5

6-(4-(1-aminoethyl)-2-fluorophenoxy)-7-methyl-benzo[c][1,2]oxaborol-1(3H)-ol (E)

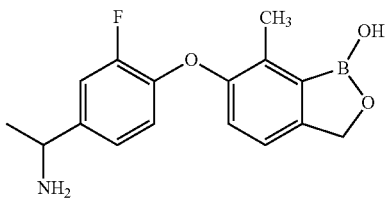 [SMILES: Cc1c(Oc2ccc(C(C)N)cc2F)ccc2c1B(O)OC2]

Preparation of 3-fluoro-4-(3-hydroxy-4-(hydroxymethyl)-2-methylphenoxy)benzonitrile To a solution of 3-fluoro-4-(4-formyl-3-hydroxy-2-methylphenoxy)benzonitrile (320 mg, 1.18 mmol) in methanol (10 mL) at room temperature was slowly added NaBH$_4$ (49 mg, 1.29 mmol). The reaction mixture was stirred at room temperature for 30 min, quenched with 1N HCl (10 mL) and extracted with EtOAc (20 mL×3). The combined organic layers were dried over anhydrous Na$_2$SO$_4$ and concentrated under reduced pressure to give crude 3-fluoro-4-(3-hydroxy-4-(hydroxymethyl)-2-methylphenoxy)benzonitrile (393 mg, 100%) as yellow solid.

Preparation of 4-(4-(((tert-butyldimethylsilyl)oxy)methyl)-3-hydroxy-2-methylphenoxy)-3-fluorobenzonitrile To a solution of 3-fluoro-4-(3-hydroxy-4-(hydroxymethyl)-2-methylphenoxy)benzonitrile (393 mg, 1.18 mmol) and imidazole (120 mg, 1.77 mmol) in DCM (10 mL) at 5° C. was slowly added a solution of TBSCl (194 mg, 1.29 mmol) in DCM (1 mL). The reaction mixture was warmed to room temperature and stirred for 24 hr. The mixture was concentrated under reduced pressure to remove the solvent. The residue was purified by column chromatography on silica gel eluting with Petroleum Ether-EtOAc (20:1 to 10:1) to give 4-(4-(((tert-butyldimethylsilyl)oxy)methyl)-3-hydroxy-2-methylphenoxy)-3-fluorobenzonitrile (200 mg) as white solid.

Preparation of 6-(((tert-butyldimethylsilyl)oxy)methyl)-3-(4-cyano-2-fluorophenoxy)-2-methylphenyl trifluoromethanesulfonate To a solution of 4-(4-(((tert-butyldimethylsilyl)oxy)methyl)-3-hydroxy-2-methylphenoxy)-3-fluorobenzonitrile (150 mg, 0.39 mmol) in DCM (2 mL) at −10° C. was added DIEA (0.3 mL, 3.9 mmol) followed by a solution of Tf$_2$O (0.14 mL, 0.78 mmol) in DCM (0.5 mL). The mixture was warmed to 0° C., stirred for 20 min and quenched with saturated NaHCO$_3$ (2 mL). The organic layer was separated and the aqueous layer was extracted with DCM (3 mL). The combined organic layers were washed with brine (2 mL), dried over anhydrous Na$_2$SO$_4$ and then concentrated under reduced pressure. The residue was purified by Prep-TLC (Petroleum Ether-EtOAc, 10:1) to give 6-(((tert-butyldimethylsilyl)oxy)methyl)-3-(4-cyano-2-fluorophenoxy)-2-methylphenyl trifluoromethanesulfonate (137 mg, 69%) as pale yellow solid.

Preparation of 3-(4-acetyl-2-fluorophenoxy)-6-(((tert-butyldimethylsilyl)oxy)methyl)-2-methylphenyl trifluoromethanesulfonate To a solution of 6-(((tert-butyldimethylsilyl)oxy)methyl)-3-(4-cyano-2-fluorophenoxy)-2-methylphenyl trifluoromethanesulfonate (5.1 g, 9.8 mmol) in THF (50 mL) at −10° C. was slowly added MeMgBr (1.6M in THF, 30.6 mL, 49.1 mmol). The reaction mixture was warmed to room temperature and stirred for 16 hr. The mixture was quenched with H$_2$O (40 mL) and extracted with EtOAc (100 mL×3). The combined organic layers were washed with brine (100 mL), dried over anhydrous Na$_2$SO$_4$ and then concentrated under reduced pressure. The residue was purified by column chromatography on silica gel, eluting with Petroleum Ether-EtOAc (5:1) to give crude 3-(4-acetyl-2-fluorophenoxy)-6-(((tert-butyldimethylsilyl)oxy)methyl)-2-methylphenyl trifluoromethanesulfonate (2.6 g, 49%) as pale yellow oil.

Preparation of 1-(4-(4-(((tert-butyldimethylsilyl) oxy)methyl)-2-methyl-3-(4,4,5,5-tetramethyl-1,3,2-dioxaborolan-2-yl)phenoxy)-3-fluorophenyl)ethan-1-one To a mixture of 3-(4-acetyl-2-fluorophenoxy)-6-(((tert-butyldimethylsilyl)oxy)methyl)-2-methylphenyl trifluoromethanesulfonate (200 mg, 0.49 mmol), Pd(dppf)Cl$_2$ (18 mg, 0.025 mmol) and potassium acetate (110 mg, 1.1 mmol) in dioxane (10 mL) was added (PinB)$_2$ (498 mg, 1.96 mmol). The reaction mixture was heated at 100° C. for 16 hr and additional Pd(dppf)Cl$_2$ (18 mg, 0.025 mmol), potassium acetate (110 mg, 1.1 mmol) and (PinB)$_2$ (498 mg, 1.96 mmol) was added to it. The mixture was heated at 100° C. for further 24 hr and then cooled to room temperature. The mixture was diluted with EtOAc (50 mL) and filtered. The filtrate was washed with H$_2$O (50 mL) and brine (20 mL), dried over anhydrous MgSO$_4$ and then concentrated under reduced pressure to remove the solvent. The residue was purified by column chromatography, eluting with Petroleum Ether-EtOAc (10:1) to give 1-(4-(4-(((tert-butyldimethylsilyl)oxy)methyl)-2-methyl-3-(4,4,5,5-tetramethyl-1,3,2-dioxaborolan-2-yl)phenoxy)-3-fluorophenyl)ethan-1-one (75 mg, 30%) as pale yellow oil.

Preparation of 1-(3-fluoro-4-((1-hydroxy-7-methyl-1,3-dihydrobenzo[c][1,2]oxaborol-6-yl)oxy)phenyl)ethan-1-one A mixture of 1-(4-(4-(((tert-butyldimethylsilyl)oxy)methyl)-2-methyl-3-(4,4,5,5-tetramethyl-1,3,2-dioxaborolan-2-yl)phenoxy)-3-fluorophenyl)ethan-1-one (50 mg, 0.10 mmol) in THF (2 mL) and 6M HCl (3 mL) was stirred at room temperature for 16 hr, diluted with EtOAc (20 mL), washed with H₂O (10 mL) and brine (5 mL). The organic layer was separated, dried over anhydrous MgSO₄ and then concentrated under reduced pressure to give crude 1-(3-fluoro-4-((1-hydroxy-7-methyl-1,3-dihydrobenzo[c][1,2]oxaborol-6-yl)oxy)phenyl)ethan-1-one (45 mg, 100%) as yellow oil, which was directly used in the next step.

Preparation of (Z)-1-(3-fluoro-4-((1-hydroxy-7-methyl-1,3-dihydrobenzo[c][1,2]oxaborol-6-yl)oxy)phenyl)ethan-1-one oxime To a solution of crude 1-(3-fluoro-4-((1-hydroxy-7-methyl-1,3-dihydrobenzo[c][1,2]oxaborol-6-yl)oxy)phenyl)ethan-1-one (45 mg, 0.10 mmol) and NH₂OH.HCl (20.6 mg, 0.30 mmol) in ethanol (2 mL) at room temperature was added K₂CO₃ (69 mg, 0.50 mmol). The mixture was heated under reflux for 1 hr, cooled to room temperature and diluted with H₂O (10 mL). The mixture was extracted with EtOAc (10 mL×3) and the combined organic layers were dried over anhydrous Na₂SO₄ and then concentrated under reduced pressure to give (Z)-1-(3-fluoro-4-((1-hydroxy-7-methyl-1,3-dihydrobenzo[c][1,2]oxaborol-6-yl)oxy)phenyl)ethan-1-one oxime (25 mg, 79%) as yellow solid.

Preparation of E

To a mixture of (Z)-1-(3-fluoro-4-((1-hydroxy-7-methyl-1,3-dihydrobenzo[c][1,2]oxaborol-6-yl)oxy)phenyl)ethan-1-one oxime (1 g, 3.2 mmol) and anhydrous NiCl₂ (1.3 g, 10 mmol) in methanol (50 mL) at −10° C. was slowly added NaBH₄ (1.21 g, 32 mmol) over a period of 40 min. The reaction mixture was warmed to room temperature, diluted with methanol (50 mL) and filtered, which was purified by preparative HPLC to afford E.

¹H NMR (400 MHz, CD₃OD) δ 7.56 (dd, J=2.0, 11.6 Hz, 1H), 7.38 (d, J=8.0 Hz, 1H), 7.35 (d, J=8.8 Hz, 1H), 7.16 (d, J=8.0 Hz, 1H), 6.98 (t, J=8.8 Hz, 1H), 5.21 (s, 2H), 4.63 (q, J=7.2 Hz, 1H), 2.50 (s, 3H), 1.80 (d, J=6.8 Hz, 3H); ESI-MS (m/z) 285 [M−NH₂]⁺

Example 6

Preparation of H

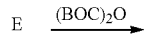

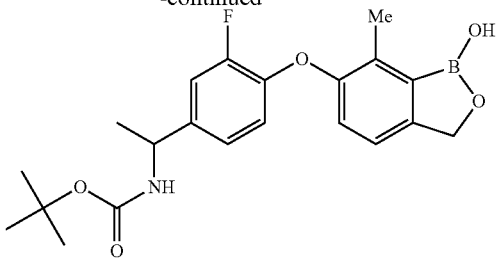

H

To the filtrate at room temperature was added (Boc)₂O (3.49 g, 16 mmol) and the mixture was stirred for 2 hr. The mixture was concentrated under reduced pressure to remove the solvent and the residue was purified by column chromatography on silica gel, eluting with Petroleum Ether-EtOAc (10:1 to 2:1) followed by Prep-HPLC to give H as white solid.

Example 7

Preparation of J

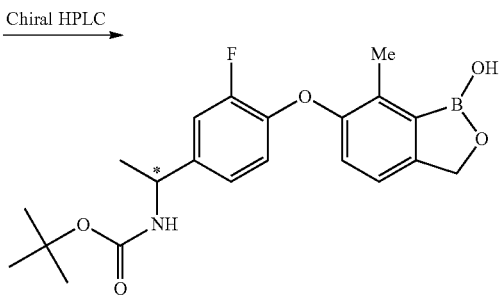

J

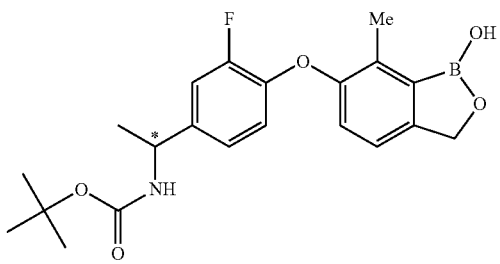

K

*: Chiral

J was obtained as Peak-1 by a chiral preparative HPLC separation of H.

Example 8

Preparation of K

K was obtained as Peak-2 by a chiral preparative HPLC separation of H.

Example 9

Preparation of F

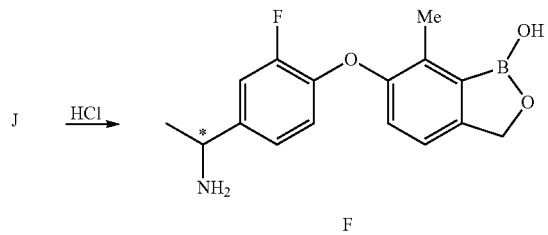

*: Chiral

A solution of compound J (75.2 mg, 0.19 mmol) in methanol (10 mL) and 6M HCl (4 mL) at room temperature was stirred for 3 hr. The solvent was removed in vacuo and the residue was purified by Prep-HPLC to give F (43 mg, 67%).

$^1$H NMR (400 MHz, CD$_3$OD) δ 7.56 (dd, J=2.0, 11.6 Hz, 1H), 7.38 (d, J=8.0 Hz, 1H), 7.35 (d, J=8.8 Hz, 1H), 7.16 (d, J=8.0 Hz, 1H), 6.98 (t, J=8.8 Hz, 1 H), 5.21 (s, 2H), 4.63 (q, J=7.2 Hz, 1H), 2.50 (s, 3H), 1.80 (d, J=6.8 Hz, 3H). MS (ESI+) m/z: 285 [M−NH$_2$]$^+$

Example 10

Preparation of G

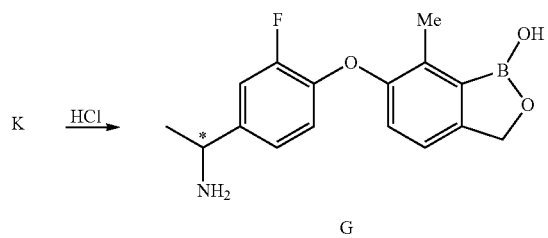

*: Chiral

A solution of compound K (76.7 mg, 0.19 mmol) in methanol (10 mL) and 6M HCl (4 mL) at room temperature was stirred for 3 hr. The solvent was removed in vacuo and the residue was purified by Prep-HPLC to give G (42 mg, 67%).

$^1$H NMR (400 MHz, CD$_3$OD) δ 7.56 (dd, J=2.0, 11.6 Hz, 1H), 7.38 (d, J=8.0 Hz, 1H), 7.35 (d, J=8.8 Hz, 1H), 7.16 (d, J=8.0 Hz, 1H), 6.98 (t, J=8.8 Hz, 1H), 5.21 (s, 2H), 4.63 (q, J=7.2 Hz, 1H), 2.50 (s, 3H), 1.80 (d, J=6.8 Hz, 3H). MS (ESI+) m/z: 285 [M−NH$_2$]$^+$.

Example 11 tert-butyl 2-fluoro-3-(1-hydroxy-7-methyl-1,3-dihydrobenzo[c][1,2]oxaborol-6-yloxy)benzylcarbamate (L)

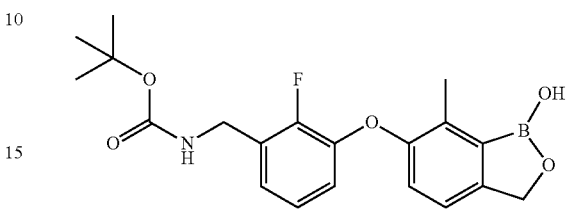

Step 1: Preparation of 2-(2-bromo-4-fluorophenyl)-1,3-dioxolane

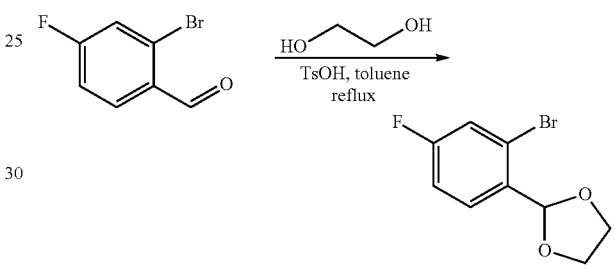

The mixture of 2-bromo-4-fluorobenzaldehyde (12.0 g, 59.1 mmol), ethane-1,2-diol (36.7 g, 591 mmol) and TsOH (1.02 g, 5.91 mmol) in Toluene (300 mL) was stirred at 110° C. for 16 h. EA (400 mL) was added and the mixture was washed with water (100 mL×2), dried over Na$_2$SO$_4$, filtered and concentrated under reduced pressure. The residue was purified by column chromatography on silica gel by elution with PE:EA=10:1 to give 2-(2-bromo-4-fluorophenyl)-1,3-dioxolane (8.76 g, yield 60%) as a white solid. $^1$H NMR (400 MHz, CDCl$_3$) δ (ppm) 7.60 (dd, J=8.8 Hz, 1H), 7.31 (dd, J=8.8 Hz, 1H), 7.08-7.04 (m, 1H), 6.04 (s, 1H), 4.17-4.10 (m, 2H), 4.08-4.04 (m, 2H).

Step 2: 2-(2-bromo-4-fluoro-3-methylphenyl)-1,3-dioxolane

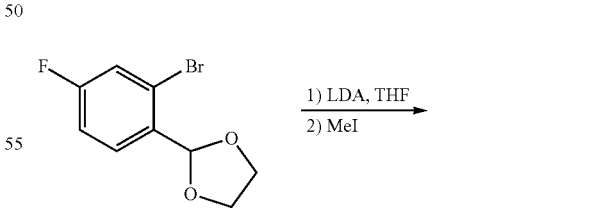

A solution of 2-(2-bromo-4-fluorophenyl)-1,3-dioxolane (7.5 g, 30 mmol) in THF (100 mL) was cooled to −78° C. and treated dropwise with LDA (2M in THF, 16.7 mL, 33.4 mmol). The mixture was stirred for 1 h at −78° C. and then was added iodomethane (5.17 g, 36.4 mmol) dropwise. Stirring continued for an additional 30 min and then kept it stirred at r.t overnight. The reaction was quenched with 50 mL sat.NH$_4$Cl at 0° C. and then diluted with ethyl acetate (100 mL×2). The organic layers were dried over Na$_2$SO$_4$ and concentrated under reduced pressure. The residue was purified by silica gel column chromatography using PE:EA=20:1 as an eluent to give 2-(2-bromo-4-fluoro-3-methylphenyl)-1,3-dioxolane (3.25 g, yield 41%) as a yellow solid. $^1$H NMR (400 MHz, CDCl$_3$) δ (ppm) 7.45 (dd, J=8.8 Hz, 1H), 7.02 (t, J=8.8 Hz, 1H), 6.11 (s, 1H), 4.16-4.10 (m, 2H), 4.08-4.05 (m, 2H), 2.36 (s, 3H); MS: m/z=261.0 (M+H, ESI+).

Step 3: Preparation of
2-bromo-4-fluoro-3-methylbenzaldehyde

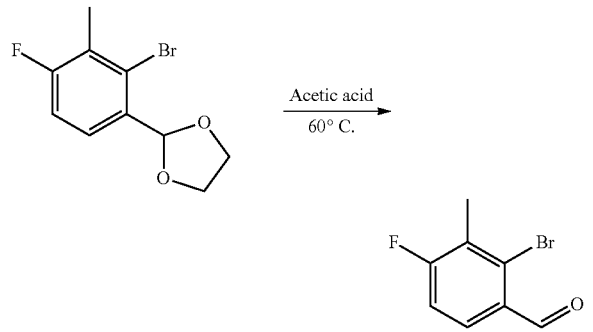

A solution of 2-(2-bromo-4-fluoro-3-methylphenyl)-1,3-dioxolane (3.0 g, 11 mmol) in acetic acid (40 mL) was stirred at 60° C. for 2 h. Water (20 mL) was added and the aqueous layer was extracted with EA (60 mL×2). The combined organic layers were dried over Na$_2$SO$_4$ and concentrated under reduced pressure. The residue was purified by silica gel column chromatography using PE:EA=10:1 as an enluent to give 2-bromo-4-fluoro-3-methylbenzaldehyde (3.1 g, 88% yield) as a white solid.

$^1$H NMR (400 MHz, CDCl$_3$) δ (ppm) 10.36 (s, 1H), 7.82 (dd, J=8.8 Hz, 1H), 7.12 (t, J=8.8 Hz, 1H), 2.41 (s, 3H).

Step 4: Preparation of
2-fluoro-3-methoxybenzaldehyde

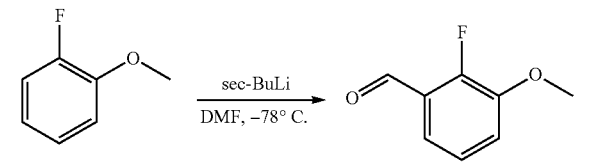

A solution of 2-fluoro-anisole (6.0 g, 47 mmol) and N,N,N',N'-tetramethylethylenediamine in THF (250 mL) was cooled to −78° C. and treated dropwise with sec-butyl lithium (1.3M in cyclohexane, 38 mL, 49 mmol). The mixture was stirred for 2 h at −78° C. and then treated with dimethylformamide (3.6 mL, 47 mmol). Stirring continued for an additional 10 min and then acetic acid (20 mL) followed by water (150 mL) was added to the mixture. The mixture was warmed to ambient temperature and then diluted with ethyl acetate. The organic layer was washed with 1M HCl, and brine. The organic layer was dried over Na$_2$SO$_4$ and concentrated under reduced pressure to give crude 2-flouro-3-methoxybenzaldehyde (4.7 g, yield 64%) as a yellow solid. $^1$H NMR (400 MHz, CDCl$_3$) (ppm) 10.40 (s, 1H), 7.45-7.40 (m, 1H), 7.23-7.18 (m, 2H), 3.94 (s, 3H).

Step 5: Preparation of
2-fluoro-3-methoxybenzaldehyde oxime

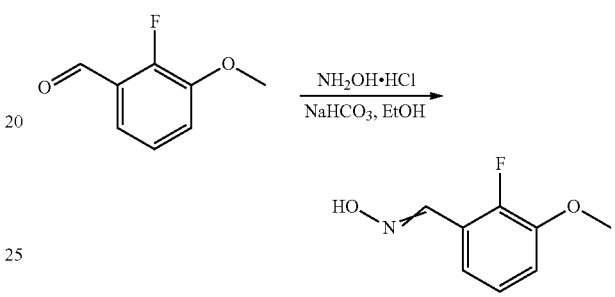

To a stirred solution of sodium hydrogen carbonate (2.73 g, 32.5 mmol) in water (50 mL) was added hydroxylamine hydrochloride (2.30 g, 33.2 mmol) in portions over 30 min. The resultant solution was added to a vigorously stirred suspension of 2-fluoro-3-methoxybenzaldehyde (5.0 g, 32.5 mmol) in ethanol (45 mL) and the reaction mixture stirred at r.t for 16 h. The resultant precipitate was removed by filtration and washed with water (100 mL×3) and then allowed to dry in air to afford 2-fluoro-3-methoxybenzaldehyde oxime (4.69 g, yield 85%) as a white crystalline solid. MS: m/z=170.1 (M+H, ESI+).

Step 6: Preparation of
2-fluoro-3-methoxyphenyl)methanamine
hydrochloride

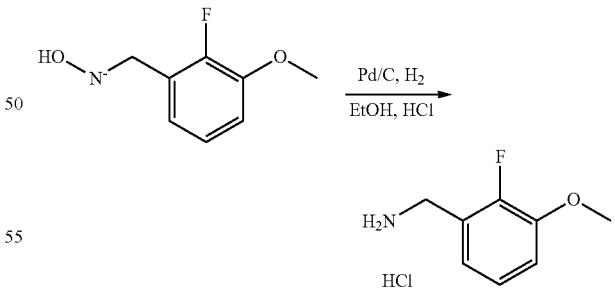

To a mixture of 10% palladium carbon (2.4 g), 10M hydrochloric acid (8.3 mL) in ethanol (200 mL) was added 2-fluoro-3-methoxybenzaldehyde oxime (12.8 g, 75.7 mmol). The mixture was stirred at room temperature for 3 h under hydrogen atmosphere of about 1 atm. The reaction mixture was filtrated through Celite. The filtrate was concentrated under reduced pressure to give 2-fluoro-3-methoxybenzylamine hydrochloride (8.2 g, yield 57%) as a white solid. MS: m/z=156.2 (M+H, ESI+).

Step 7: Preparation of 3-(aminomethyl)-2-fluorophenol hydrobromide

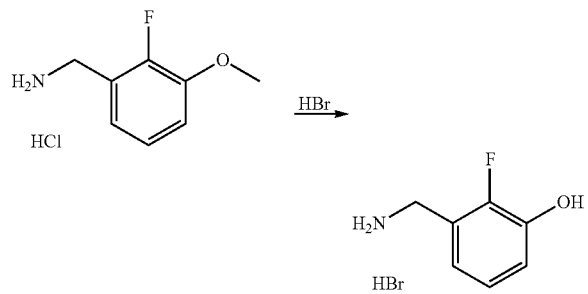

A solution of 2-fluoro-3-methoxybenzylamine hydrochloride (4.0 g, 20.9 mmol) in 48% HBr (15 mL) was refluxing with heating for 5 h. The reaction mixture left to stand for cooling to about room temperature was concentrated under reduced pressure to give 2-fluoro-3-hydroxybenzylamine hydrobromide (4.0 g, yield 86%) which was directly used in next step without additional purification.

Step 8: Preparation of tert-butyl 2-fluoro-3-hydroxybenzylcarbamate

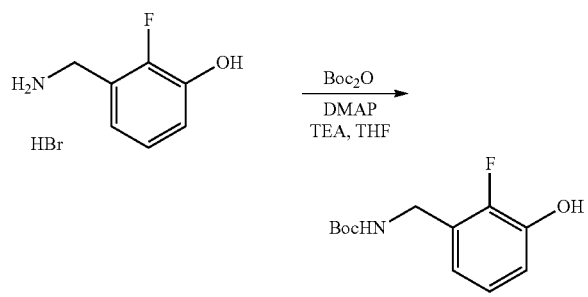

A mixture of 2-fluoro-3-hydroxybenzylamine hydrobromide (2.6 g, 11.7 mmol), di-tert-butyl dicarbonate (4.9 g, 22.5 mmol), triethylamine (6.4 mL, 90.4 mmol) and about 0.1 g of 4-dimethylaminopyridine in THF (30 mL) was stirred at a room temperature for 6 h. Thereafter, water (50 mL) was added to the reaction mixture, and it was then extracted with ethyl acetate (100 mL×2). The organic layers were successively washed with 5% hydrochloric acid, water, a saturated sodium bicarbonate aqueous solution and brine, and it was then dried over $Na_2SO_4$, followed by concentration under reduced pressure to give tert-butyl 2-fluoro-3-hydroxybenzylcarbamate (2.0 g, yield 70%) as a white solid. MS: m/z=264.1 (M+Na$^+$, ESI+).

Step 9: Preparation of tert-butyl tert-butyl 3-(3-bromo-4-formyl-2-methylphenoxy)-2-fluorobenzyl-carbamate

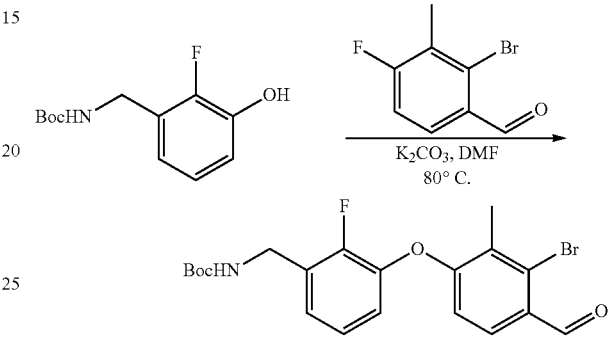

A mixture of tert-butyl 3-(3-bromo-4-formylphenoxy)-2-fluorobenzylcarbamate (2.0 g, 8.3 mmol), 2-bromo-4-fluoro-3-methylbenzaldehyde (1.98 g, 9.13 mmol) and $K_2CO_3$ (3.4 g, 25 mmol) in DMF (40 mL) was stirred at 80° C. overnight. Water (50 mL) was added and the mixture was extracted with EA (100 mL×2). The combined organic layers were dried over $Na_2SO_4$, filtered and concentrated under reduced pressure. The residue was purified by silica gel column chromatography using PE:EA=10:1 as an eluent to give tert-butyl 3-(3-bromo-4-formyl-2-methylphenoxy)-2-fluorobenzylcarbamate (2.4 g, yield 66%) as a white solid. $^1$H NMR (400 MHz, CDCl$_3$) δ (ppm) 10.29 (s, 1H), 7.64 (d, J=8.8 Hz, 1H), 7.19-7.16 (m, 1H), 7.07 (t, J=8.0 Hz, 1H), 6.94 (dd, J=8.0 Hz, 1H), 6.60 (d, J=8.4 Hz, 1H), 4.91 (s, 1H), 4.33 (d, J=6.0 Hz, 2H), 2.46 (s, 3H), 1.38 (s, 9H); MS: m/z=382.0 (M-butyl, ESI+).

Step 10: Preparation of tert-butyl 3-(3-(5,5-dimethyl-1,3,2-dioxaborinan-2-yl)-4-formyl-2-methylphenoxy)-2-fluorobenzylcarbamate

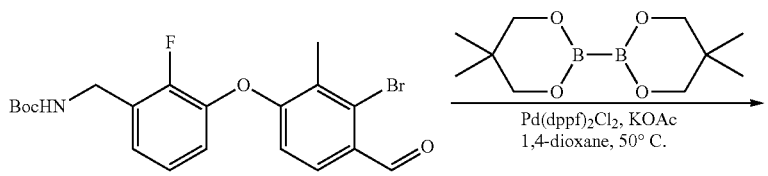

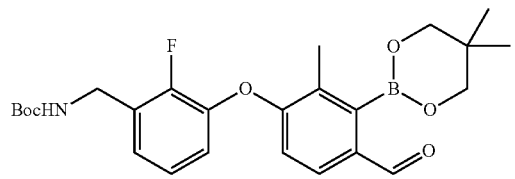

A mixture of tert-butyl 3-(3-bromo-4-formyl-2-methylphenoxy)-2-fluorobenzylcarbamate (2.4 g, 5.48 mmol), 5,5,5',5'-tetramethyl-2,2'-bi(1,3,2-dioxaborinane) (4.95 g, 21.9 mmol), Pd(dppf)$_2$Cl$_2$ (220 mg, 0.3 mmol) and KOAc (4.30 g, 43.84 mmol) was stirred at 50° C. overnight under N$_2$ atomsphere. The mixture was then cooled to room temperature, filtered and the solvent was concentrated by rotary evaporation. The residue was purified by silica gel column chromatography using PE:EA=5:1 as an eluent to give tert-butyl 3-(3-(5,5-dimethyl-1,3,2-dioxaborinan-2-yl)-4-formyl-2-methylphenoxy)-2-fluorobenzylcarbamate (1.24 g, 48%) as a white solid. It was used in next step directly.

Step 11: Preparation of tert-butyl 2-fluoro-3-(1-hydroxy-1,3-dihydrobenzo[c][1,2]oxaborol-6-yloxy)benzylcarbamate (L)

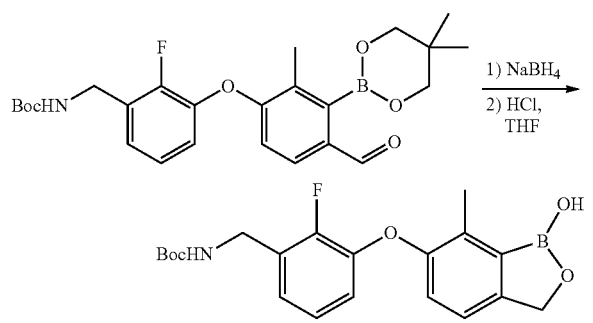

To a mixture of tert-butyl 3-(3-bromo-4-formylphenoxy)-2-fluorobenzylcarbamate (600 mg, 1.37 mmol) in THF (20 mL) was added NaBH$_4$ (104 mg, 2.74 mmol) at 0° C. and the mixture was stirred at room temperature for 4 h. 6M HCl (2 mL) was added and continued to stir for 2 h. The mixture was concentrated and the residue was purified by Preparative HPLC to give tert-butyl 2-fluoro-3-(1-hydroxy-7-methyl-1,3-dihydrobenzo[c][1,2]oxaborol-6-yloxy)benzylcarbamate (212 mg, yield 40%) as a white solid.

$^1$H NMR (400 MHz, DMSO-d$_6$) δ (ppm) 9.09 (s, 1H), 7.45 (t, J=5.6 Hz, 1H), 7.22 (d, J=8.0 Hz, 1H), 7.07-6.97 (m, 3H), 6.70 (t, J=8.0 Hz, 1H), 4.95 (s, 1H), 4.21 (d, J=5.6 Hz, 2H), 2.33 (s, 3H), 1.40 (s, 9H); HPLC purity: 94.57% at 214 nm and 100% at 254 nm; MS: m/z=410.1 (M+Na, ESI+).

Example 12

6-(3-(aminomethyl)-2-fluorophenoxy)-7-methylbenzo[c][1,2]oxaborol-1(3H)-ol (M)

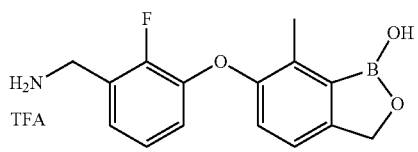

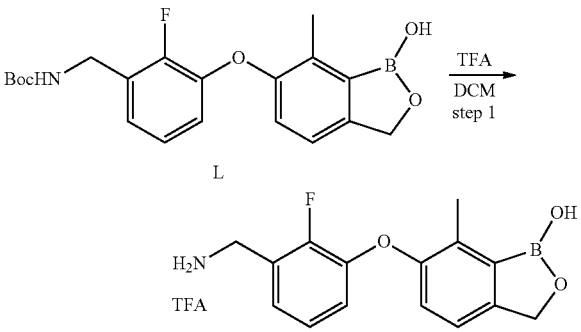

To a solution of tert-butyl 2-fluoro-3-(1-hydroxy-7-methyl-1,3-dihydrobenzo[c][1,2]oxaborol-6-yloxy)benzylcarbamate (150 mg, 0.39 mmol) in DCM (5 mL) was added TFA (0.8 mL) dropwise at 0° C., then the mixture was stirred at room temperature overnight. The solvent was removed and the residue was purified by preparative HPLC under acidic condition to give TFA salt 6-(3-(aminomethyl)-2-fluorophenoxy)-7-methylbenzo[c][1,2]oxaborol-1(3H)-ol (25 mg, yield 17%) as a white solid. $^1$H NMR (400 MHz, DMSO-d$_6$) δ (ppm) 9.14 (s, 1H), 8.30 (b, 3H), 7.27-7.16 (m, 3H), 7.01 (d, J=8.4 Hz, 1H), 6.87 (t, J=8.0 Hz, 1H), 4.97 (s, 2H), 4.14 (s, 2H), 2.33 (s, 3H) ppm; HPLC purity: 100% at 220 nm and 100% at 254 nm; MS: m/z=288.2 (M+H, ESI+).

Example 13

6-(4-(aminomethyl)-2-chlorophenoxy)-7-isopropylbenzo[c][1,2]oxaborol-1 (3H)-ol (N)

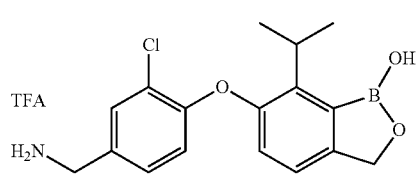

Step 1: Preparation of 1-(2,6-dimethoxyphenyl)ethanone

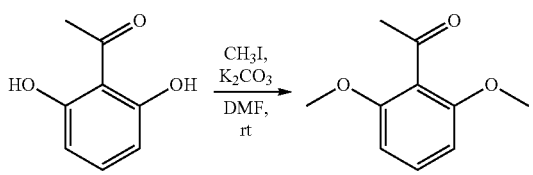

To a solution of compound 1-(2,6-dihydroxyphenyl)ethanone (25.0 g, 164.5 mmol) and potassium carbonate (68.1 g, 493.4 mmol) in DMF (100 mL) was added iodomethane (24.3 mL, 411.2 mmol) slowly at room temperature. The mixture was stirred for 16 h at room temperature. The mixture was poured into ice water (500 mL) and stirred for 30 min. The precipitate was filtered, washed with water and dried to give 1-(2,6-dimethoxyphenyl)ethanone as a light yellow solid (25 g, yield 84%). MS: m/z=181.0 (M+H, ESI+).

Step 2: Preparation of 2-(2, 6-dimethoxyphenyl)propan-2-ol

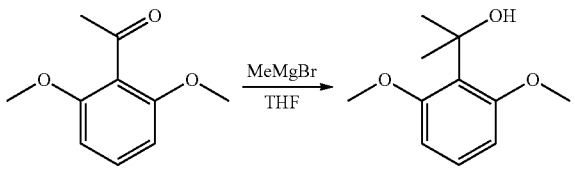

To a solution of 1-(2,6-dimethoxyphenyl)ethanone (25.0 g, 138.9 mmol) in THF (250 mL) was added MeMgBr (3M in THF, 185.2 mL, 555.6 mmol) dropwise at 0° C. The reaction mixture was stirred for 16 h at room temperature. The mixture was quenched by solution of NH$_4$Cl at 0° C. and extracted with EA (100×3 mL). The organic layers were washed with water and brine, dried over Na$_2$SO$_4$, filtered, and concentrated. The resulting oil was purified by silica gel column chromatography using PE:EA=20:1 as an eluent to give 2-(2,6-dimethoxyphenyl)propan-2-ol (20.4 g, yield 75%) as a yellow oil. MS: m/z=179.0 (M−OH, ESI+).

Step 3: Preparation of 2-isopropyl-1,3-dimethoxybenzene

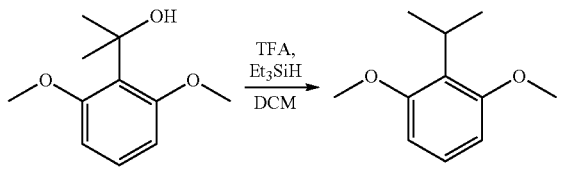

To a solution of 2-(2,6-dimethoxyphenyl)propan-2-ol (20.4 g, 104.1 mmol) in DCM (150 mL) was added TFA (23 mL, 312 mmol) and Et$_3$SiH (47.5 mL, 312 mmol) slowly at −30° C. Then the mixture was stirred for 6 h at rt. EA (250 mL) was added and the solution was washed with water (100 mL×3), dried over Na$_2$SO$_4$, filtered and concentrated under the reduced pressure. The residue was purified by silica gel column chromatography using PE:EA=30:1 as an eluent to give 2-isopropyl-1,3-dimethoxybenzene (14 g, yield 75%) as light yellow oil. $^1$H NMR (400 MHz, CDCl$_3$) δ (ppm) 7.10 (t, J=8.4 Hz, 1H), 6.54 (d, J=8.4 Hz, 2H), 3.80 (s, 6H), 3.64-3.57 (m, 1H), 1.28 (d, J=6.8 Hz, 6H).

Step 4: Preparation of 2-isopropylbenzene-1, 3-diol

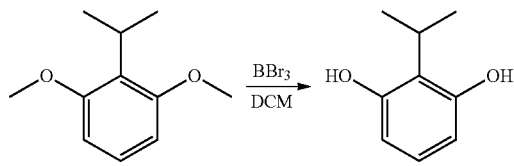

To a solution of 2-isopropyl-1,3-dimethoxybenzene (14.0 g, 77.8 mmol) in DCM (100 mL) was added BBr$_3$ (3M in DCM, 65 mL, 195 mmol) slowly at −30° C. Then the mixture was stirred for 16 h at room temperature. The resulting solution was poured into ice water and extracted with EA. The combined organic layers were washed with brine, dried over Na$_2$SO$_4$, filtered and concentrated under the reduced pressure. The residue was purified by silica gel column chromatography using PE:EA=10:1 as an eluent to give 2-isopropylbenzene-1,3-diol (9.5 g, yield 80%) as a white solid. $^1$H NMR (400 MHz, CDCl$_3$) δ (ppm) 6.88 (t, J=8.0 Hz, 1H), 6.32 (d, J=8.0 Hz, 2H), 4.82 (b, 2H), 3.50-3.43 (m, 1H), 1.36 (d, J=7.6 Hz, 6H); MS: m/z=153.0 (M+H, ESI+).

Step 5: Preparation of 2, 4-dihydroxy-3-isopropylbenzaldehyde

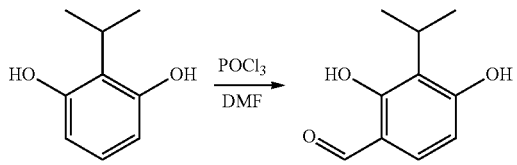

To a solution of DMF (10 mL) was added POCl$_3$ (17 mL, 188 mmol) slowly at 0° C. The reaction mixture was stirred for 20 min at 0° C., then the solution of 2-isopropylbenzene-1,3-diol (9.5 g, 62.5 mmol) in DMF (8 mL) was added slowly at 0° C. The mixture was stirred for 3 h at room temperature. The resulting solution was poured into ice water and stirred for 1 h, and the solution was placed over night. The precipitate was filtered, washed with water and dried to give 2,4-dihydroxy-3-isopropylbenzaldehyde (6.75 g, yield 65%) as a white solid. $^1$H NMR (400 MHz, CDCl$_3$) δ (ppm) 11.79 (s, 1H), 9.66 (s, 1H), 7.24 (d, J=8.4 Hz, 1H), 6.40 (d, J=8.4 Hz, 1H), 3.55-3.48 (m, 1H), 1.35 (d, J=6.8 Hz, 6H) m; MS: m/z=181.0 (M+H, ESI+).

Step 6: Preparation of 4-(benzyloxy)-2-hydroxy-3-isopropylbenzaldehyde

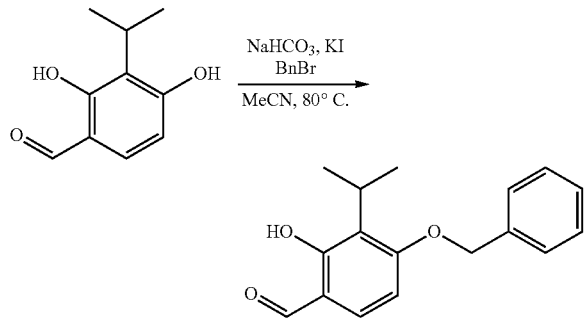

A mixture of 2,4-dihydroxy-3-isopropylbenzaldehyde (6.75 g, 37.5 mmol), NaHCO$_3$ (9.45 g, 112.5 mmol) and KI (1.25 g, 7.5 mmol) in MeCN (100 mL) was slowly warmed to 60° C. At this time, benzyl bromide (5.05 mL, 41.25 mmol) was added and the mixture was heated to 80° C. and stirred overnight. The mixture was then cooled to room temperature, filtered and the solvent was concentrated by rotary evaporation. The residue was purified by silica gel column chromatography using PE:EA=10:1 as an eluent to give 4-(benzyloxy)-2-hydroxy-3-isopropylbenzaldehyde as a yellow solid (6.9 g, yield 68%).

$^1$H NMR (400 MHz, CDCl$_3$) δ (ppm) 11.60 (s, 1H), 9.69 (s, 1H), 7.43-7.35 (m, 5H), 7.32 (d, J=8.4 Hz, 1H), 6.59 (d, J=8.4 Hz, 1H), 5.17 (s, 2H), 3.70-3.62 (m, 1H), 1.32 (d, J=6.8 Hz, 6H); MS: m/z=271.0 (M+H, ESI+).

Step 7: Preparation of 3-(benzyloxy)-6-formyl-2-isopropylphenyl trifluoromethanesulfonate

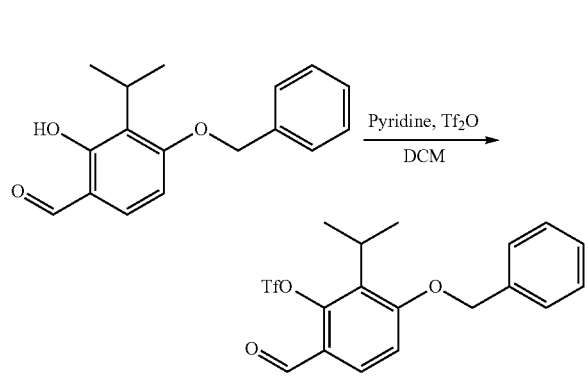

To a solution of 4-(benzyloxy)-2-hydroxy-3-isopropylbenzaldehyde (6.9 g, 26 mmol) and pyridine (10.5 mL, 128 mmol) in DCM (100 mL) was added Tf$_2$O (12.1 mL, 63.85 mmol) slowly at 0° C. The reaction mixture was stirred for 3 h at room temperature. The mixture was poured into water and extracted with EA (75 mL×3). The combined organic layers were washed with brine, dried over Na$_2$SO$_4$, filtered and concentrated under the reduced pressure. The residue was purified by silica gel column chromatography using PE:EA=20:1 as an eluent to give 3-(benzyloxy)-6-formyl-2-isopropylphenyl trifluoromethanesulfonate (5.65 g, yield 55%) as a light yellow solid. MS: m/z=403.1 (M+H, ESI+).

Step 8: Preparation of 4-(benzyloxy)-2-(5,5-dimethyl-1,3,2-dioxaborinan-2-yl)-3-isopropylbenzaldehyde

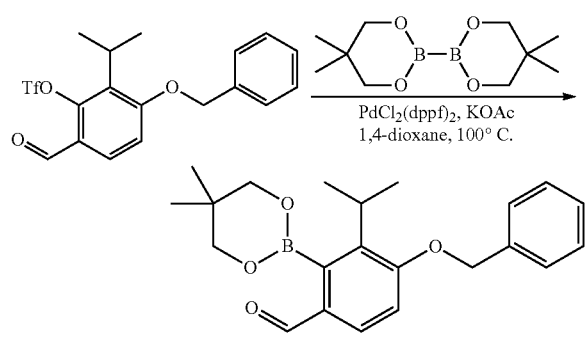

A mixture of 3-(benzyloxy)-6-formyl-2-isopropylphenyl trifluoromethanesulfonate (5.65 g, 14.1 mmol), KOAc (6.9 g, 70 mmol), 5,5,5',5'-tetramethyl-2,2'-bi(1,3,2-dioxaborinane) (9.5 g, 42 mmol) and PdCl$_2$(dppf)$_2$ (565 mg, 0.77 mmol) in 1,4-dioxane (150 mL) was heated to 100° C. and stirred for 16 h under nitrogen atmosphere. The mixture was then cooled to room temperature, filtered and the solvent was concentrated by rotary evaporation. The residue was purified by silica gel column chromatography using PE:EA=5:1 as an eluent to give 4-(benzyloxy)-2-(5,5-dimethyl-1,3,2-dioxaborinan-2-yl)-3-isopropylbenzaldehyde as a yellow solid (3.6 g, yield 70%). It was used in next step directly.

Step 9: Preparation of 6-(benzyloxy)-7-isopropylbenzo[c][1,2]oxaborol-1(3H)-ol

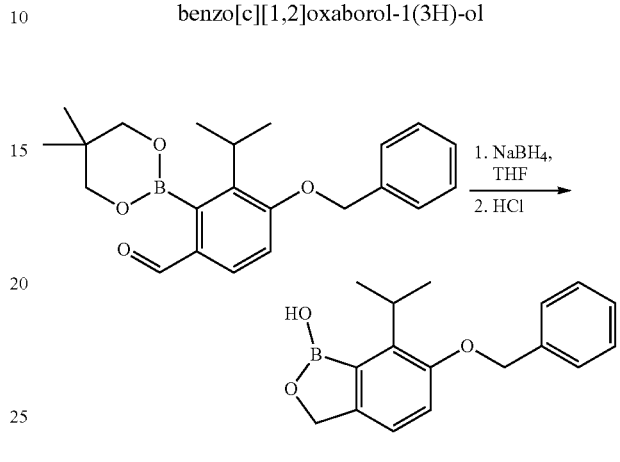

To a solution of 4-(benzyloxy)-2-(5,5-dimethyl-1,3,2-dioxaborinan-2-yl)-3-isopropylbenzaldehyde (3.6 g, 9.85 mmol) in THF (50 mL) was added NaBH$_4$ (0.75 g, 20 mmol). The reaction mixture was stirred at r.t for 3 h, then it was slowly added 6M HCl (5.0 mL) on an ice bath. The mixture was continued to stir for 16 h at room temperature. The reaction mixture was poured into water and extracted with EA (75 mL×3). The combined organic layers were washed with brine, dried over Na$_2$SO$_4$, filtered and concentrated under the reduced pressure. The residue was purified by silica gel column chromatography using PE:EA=20:1 as an eluent to give 6-(benzyloxy)-7-isopropylbenzo[c][1,2]oxaborol-1(3H)-ol (2.1 g, yield 75%) as a white solid. $^1$H NMR (400 MHz, DMSO-d$_6$) δ (ppm) 9.00 (s, 1H), 7.31-7.47 (m, 5H), 7.17 (d, J=8.0 Hz, 1H), 7.13 (d, J=8.0 Hz, 1H), 5.11 (s, 2H), 4.88 (s, 2H), 3.74-3.67 (m, 1H), 1.28 (d, J=7.2 Hz, 6H); MS: m/z=283.1 (M+H, ESI+).

Step 10: Preparation of 7-isopropylbenzo[c][1,2]oxaborole-1,6(3H)-diol

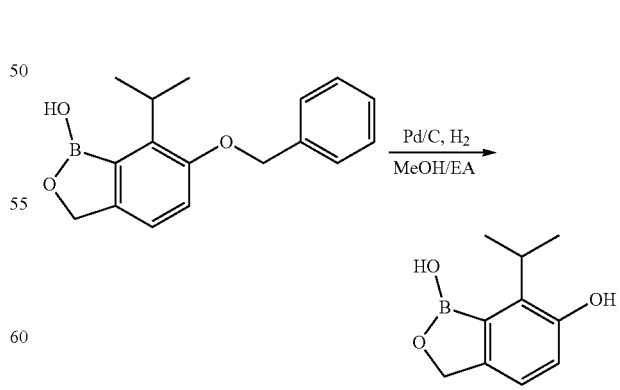

To a solution of 6-(benzyloxy)-7-isopropylbenzo[c][1,2]oxaborol-1(3H)-ol (2.1 g, 7.45 mmol) in MeOH (25 mL) and EA (25 mL) was hydrogenated using 10% Pd/C (745 mg) as a catalyst under atmospheric pressure overnight. The catalyst was removed by filtration through Celite and the solvent was evaporated under the reduced pressure. The residue was purified by silica gel column chromatography using PE:EA=2:1 as an eluent to give 7-isopropylbenzo[c][1,2]oxaborole-1,6(3H)-diol (1.14 g, yield 80%) as light yellow oil.

$^1$H NMR (400 MHz, DMSO-d$_6$) δ (ppm) 8.99 (s, 1H), 8.86 (s, 1H), 6.96 (d, J=8.0 Hz, 1H), 6.87 (d, J=8.0 Hz, 1H), 4.83 (s, 2H), 3.63-3.56 (m, 1H), 1.26 (d, J=6.8 Hz, 6H); MS: m/z=193.1 (M+H, ESI+).

Step 11: Preparation of 3-chloro-4-(1-hydroxy-7-isopropyl-1,3-dihydrobenzo[c][1,2]oxaborol-6-yloxy)benzonitrile

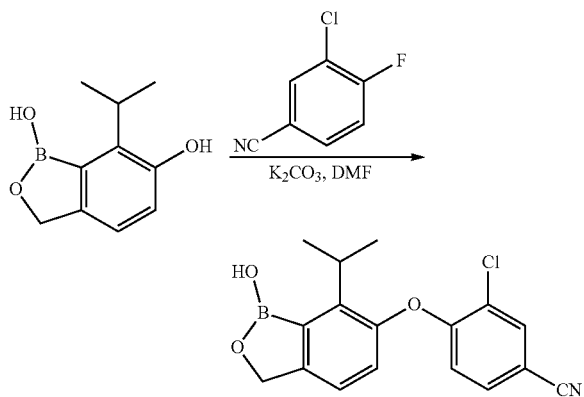

To a solution of 7-isopropylbenzo[c][1,2]oxaborole-1,6 (3H)-diol (540 mg, 2.81 mmol) and K$_2$CO$_3$ (775 mg, 5.62 mmol) in DMF (20 mL) was added 3-chloro-4-fluorobenzonitrile (481 mg, 3.09 mmol). The reaction mixture was heated to 80° C. for 16 h. The resulting mixture was filtered and the filtration was purified by preparative HPLC to give 3-chloro-4-(1-hydroxy-7-isopropyl-1,3-dihydrobenzo[c][1,2]oxaborol-6-yloxy)benzonitrile (368 mg, yield 40%) as a white solid.

$^1$H NMR (400 MHz, DMSO-d$_6$) δ (ppm) 9.28 (s, 1H), 8.21 (d, J=2.0 Hz, 1H), 7.72 (dd, J=8.8, 2.0 Hz, 1H), 7.33 (d, J=8.0 Hz, 1H), 7.16 (d, J=8.0 Hz, 1H), 6.72 (d, J=8.8 Hz, 1H), 5.00 (s, 2H), 3.43-3.39 (m, 1H), 1.22 (d, J=7.2 Hz, 6H); HPLC purity: 100% at 220 nm and 100% at 254 nm; MS: m/z=328.1 (M+H, ESI+).

Step 12: Preparation of 6-(4-(aminomethyl)-2-chlorophenoxy)-7-isopropylbenzo[c][1,2]oxaborol-1 (3H)-ol (N)

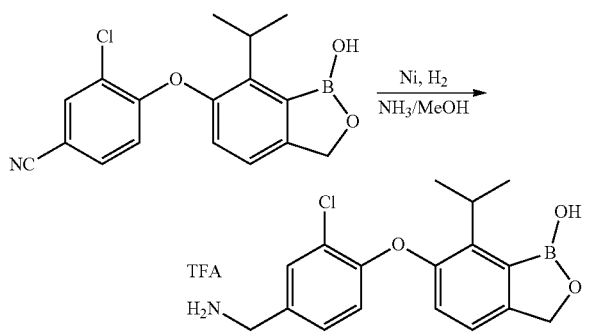

To a solution of 3-chloro-4-(1-hydroxy-7-isopropyl-1,3-dihydrobenzo[c][1,2]oxaborol-6-yloxy)benzonitrile (100 mg, 0.30 mmol) in MeOH (2 mL) and 7M MeOH NH$_3$ (2 mL) was hydrogenated using Rany Ni (20 mg) as a catalyst under atmospheric pressure for 2 h. The catalyst was removed by filtration through Celite and the solvent was evaporated under the reduced pressure. The residue was purified by preparative HPLC to give TFA salt 6-(4-(aminomethyl)-2-chlorophenoxy)-7-isopropylbenzo[c][1,2]oxaborol-1(3H)-ol (42 mg, yield 43%) as a white solid.

$^1$H NMR (400 MHz, DMSO-d$_6$) δ (ppm) 9.24 (s, 1H), 8.09 (b, 3H), 7.71 (d, J=2.0 Hz, 1H), 7.33 (dd, J=8.4, 2.0 Hz, 1H), 7.28 (d, J=8.4 Hz, 1H), 6.98 (d, J=8.4 Hz, 1H), 6.71 (d, J=8.4 Hz, 1H), 4.98 (s, 2H), 4.00 (s, 2H), 3.41-3.49 (m, 1H), 1.25 (d, J=7.2 Hz, 6H); HPLC purity: 100% at 214 nm and 100% at 254 nm; MS: m/z=315.1 (M−NH$_2$, ESI+).

Example 2

In Vitro Assays

Materials:
6-(4-(aminomethyl)-2-chlorophenoxy)benzo[c][1,2]oxaborol-1(3H)-ol, was synthesized at Anacor Pharmaceuticals as described in U.S. Pat. No. 8,039,450; most of the analogs were synthesized using methods as outlined in Akama T. et al., *Bioorg Med Chem Lett.* 2013 Mar. 15; 23(6):1680-3. All lots used had purity >95% as assessed by HPLC and $^1$H-NMR. Animals. Sprague-Dawley rats were purchased from Charles River Laboratories (Hollister, Calif.). SHR rats were obtained from Shanghai, SLA Laboratory, Animal Co, Ltd. All animal studies were performed with the approval of Institutional Animal Care and Use Committees in accordance with the Guide for the Care and Use of Laboratory Animals.

Cytokine Secretion Inhibition:
Measurement of the inhibition of cytokine secretion from stimulated human peripheral blood mononuclear cells by drugs was performed as described in Dong C. et al., *J Pharmacol Exp Ther.* 2013 February; 344(2):436-46; and Akama T. et al., *Bioorg Med Chem Lett.* 2013 Mar. 15; 23(6):1680-3. Briefly PBMC were incubated with drug, and stimulators; LPS for 24 hours to release TNF-α, and IL-6; PHA for 24 hours, to release IL-2 and IFN-γ, and PHA for 48 hours, to release IL-5 and IL-13. The cell culture supernatants were collected for cytokine determinations using Cisbio HTRF cytokine determination kits. Compounds were prepared using an eight point 1:10 dilution series starting at 10 or 100 uM; the resulting dose-response curves were fit to the four parameter sigmoid equation.

| Results: | | |
|---|---|---|
| | Inhibition of TNF-a Secretion from LPS Stimulated hPBMC [IC50, uM] | Inhibition of hROCK1 Phosphorylation [IC50, uM] |
| A | 3.61 | 0.29 |
| B | 98.97 | 11.03 |
| C | 11.97 | 0.54 |
| D | 12.30 | 0.34 |
| E | 5.40 | 0.42 |
| F | 20.51 | 0.54 |
| G | 5.18 | 0.17 |
| L | | 0.72 |
| M | | 0.247 |
| N | 5.63 | 0.596 |

Jurkat Cell Growth:

Log phase Jurkat, Clone E6-1 (ATCC® TIB-152™), at 2×10^4 cells per well, were cultured for 3 days at 37° C. in the presence and absence of drug. Growth was assessed using the MTT [3-(4,5-dimethylthiazol-2-yl)-2,5 diphenyl-tetrazolium bromide] mitochondrial reduction assay. Under these conditions, untreated Jurkat cells grow at least 2 doublings in 3 days. Percent inhibition or dose response $IC_{50}$ were calculated as for the trypanosome tests above.

Kinase Binding Panel:

Kinase inhibition potency was measured using KINOM-Escan™ technology across 402 human kinases [Fabian et al., Nat Biotechnol. 2005 March; 23(3):329-36] (DiscoverRx, Inc., (Fremont, Calif.)). The assay is based on a competition binding assay which quantitatively measures the ability of a compound to compete with an immobilized, active-site directed ligand. The assay has been shown to accurately assess the affinity of inhibitors for kinases as compared to phosphorylation based kinase assays [Karaman et al., Nat Biotechnol. 2008 January; 26(1):127-32; Fabian et al., Nat Biotechnol. 2005 March; 23(3):329-36]. The assay is performed by combining three components: DNA-tagged kinase; immobilized ligand; and a test compound. Binding reactions were assembled by combining, for 1 hr at room temperature, kinases, liganded affinity beads, and test compounds in binding buffer (20% SeaBlock, 0.17×PBS, 0.05% Tween-20, 6 mM DTT). The assay plates were washed and then re-suspended in elution buffer for 30 min. (PBS, 0.05% Tween 20, 0.5 μM non-biotinylated affinity ligand). The kinase concentration in the eluates was measured by qPCR.

Results:

|   | ROCK1 IC50 (μM) | ROCK2 IC50 (μM) |
|---|---|---|
| A | 0.29 | 0.25 |
| B | 23 | 16 |
| C | 0.54 | 0.45 |
| D | 0.34 | 0.25 |
| E | 0.42 | 0.25 |
| F | 0.54 | 0.51 |
| G | 0.17 | 0.17 |
| L | 0.72 | 0.664 |
| M | 0.247 | 0.216 |
| N | 0.0596 | 0.0472 |

Phosphorylation of activity of ROCK1 and ROCK2 and those of other kinases, AKT1, GRK2, PKA, PKCa and RSK1 were performed by Reaction Biology (Malvern, Pa.) (Ma et al., 2008) The ROCK1 enzyme tested was GST[1-535] ROCK1 (Genbank, NP 005397), ROCK2 was GST[5-554] (Genbank, 3327051). For the kinase assay buffers contained 20 mM Hepes, 10 mM $MgCl_2$, 2 mM DTT, 0.02 mg/mL BSA, 0.1% DMSO, 1 mM EGTA, 0.02% Brij-35, 10 uM ATP, [γ$P^{33}$]-ATP and for ROCK enzymes, 20 uM long S6-peptide (32 amino acids length). Appropriate substrates and activation was applied for the other kinases tested. Each enzyme was preincubated with test compound for 15 min., and the reaction started by addition of ATP. Samples were incubated at room temperature for 120 min, and applied to P81 ion exchange paper and washed extensively; the radioactive content of the filters were determined. For all the enzymes tested the Km[ATP] was measured as follows: ROCK1, 16 uM; ROCK2, 17.5 uM; AKT1, 35 uM; GRK2, 54 uM; PKA, 19 uM; PKCa, 10 uM; and RSK1, 26 uM. Selectivity ratio is the value for PKA/ROCK2.

Results:
IC50 (nM)

|   | C | D | E | F | G |
|---|---|---|---|---|---|
| ROCK1 | 0.54 | 0.34 | 0.42 | 0.54 | 0.17 |
| ROCK2 | 0.45 | 0.25 | 0.25 | 0.51 | 0.17 |
| SELECTIVITY RATIO | >111 | 16.29 | 24.74 | 21.51 | 10.40 |
| AKT1 | >30 | 9.25 | 21.5 | 44.1 | 10.87 |
| GRK2 | >20 | >20 | >20 | >20 | 13.88 |
| PKA | >50 | 4.06 | 6.09 | 10.97 | 1.79 |
| PKCa | >20 | >20 | >20 | >20 | 15.64 |
| RSK1 | >50 | 5.01 | 8.31 | 17.17 | 3.62 |

IC50 (nM)

|   | L | M | N |
|---|---|---|---|
| ROCK1 | 0.72 | 0.25 | 0.060 |
| ROCK2 | 0.66 | 0.22 | 0.047 |
| SELECTIVITY RATIO | 11.87 | 15.65 | 1.17 |
| AKT1 | >30 | >30 | 4.22 |
| GRK2 | >30 | >30 |  |
| PKA | 7.88 | 3.38 | 0.055 |
| PKCa | >30 | >30 | 10.8 |
| RSK1 | 25.00 | 5.19 | 0.195 |

Intracellular MYPT1 phosphorylation assay used the procedures of Garton et al. with minor modifications (Garton et al. Methods Enzymol. 2008; 439:491-500). PANC-1 cells (ACTT, CRL-1469), 18×10³/well, grown over night in DMEM medium supplemented with 4.5 g/L glucose, L-glutamine, sodium pyruvate and 10% FBS at 37° C. Compounds were applied to the cells for one hour (DMSO final 1%) and the cells were then lysed. Phosphorylated-MYPT1 was detected using plate immobilized anti-MYPT1 antibody (BD Biosciences, cat. 612165), anti-phospo-MYPT1(T853), US Biological, cat. M9925-08) and secondary HRP-conjugated goat anti-rabbit IgG antibody (Jackson Laboratories, cat. 111-035-003), phospho-MYPT1 was quantified using color formed by the tetramethylbenzidine (TMB) HRP substrate.

Results:

| IC50: Inhib p-MYPT1 Phosphorylation in H. sapiens PANC-1 cells, .0417 days [uM] | IC50: ROCK1: H. sapiens [uM] |
|---|---|
| C | 48.15 | 0.54 |
| D | 18.23 | 0.34 |
| E | 39.69 | 0.42 |
| F | 56.35 | 0.54 |
| G | 18.70 | 0.17 |

Relaxation of rat aorta smooth muscle was assessed using rat thoracic aorta as outlined in Eltze and Boer (Eltze Metal. Eur J Pharmacol. 1992 Dec. 2; 224(2-3):125-36) using tissue isolated from adult Wistar rats, in oxygenated Kerbs-Ringer buffer at 37° C. Tests started from a resting tension of 1 g. Agonist mode, contraction, testing and relaxation testing were preformed for all compounds; which were applied from DMSO stocks with the final concentration of 0.5% DMSO. Relaxation testing was performed in tissues pre-contracted with 1 uM norepinephrine, this dose is approximately 8-fold the norepinephrine contraction $IC_{50}$. Compounds were applied for 5 min before the tension was measured. Two separate tissues were used for each measurement of the response to each drug dose.

Relaxation of trachea smooth muscle was assessed using guinea pig trachea as detailed in Wasserman and Griffin (Wasserman M A et al., *Eur J Pharmacol.* 1977 Dec. 15; 46(4):303-13) using tissue isolated from adult Dunkin-Hartley guinea pigs. Tests were conducted in Kerbs solution with 2.8 uM indomethacin present to suppress prostaglandin production and allow a stable baseline. Test conditions and procedures were similar to the aorta tests with carbacol at 1 uM, used to pre-contract the tissue for relaxation tests. Compounds were applied for 30 min before the tension was measured. Six separate tissues were used for each measurement of the response to each drug dose.

Pharmacokinetics of 6-(4-(aminomethyl)-2-chlorophenoxyl)benzo[c][1,2] xaborol-1(3H)-ol in rats were studied using methods similar to Dong et al. (Dong C. et al., *J Pharmacol Exp Ther.* 2013 February; 344(2):436-46). Adult male Sprague-Dawley rats, received 6-(4-(aminomethyl)-2-chlorophenoxyl)benzo[c][1,2]oxaborol-1(3H)-ol either by intravenous injection with 2 mg/kg in a solution composed of 50% saline, 40% PEG400, and 10% DMSO, pH 5.7, or by oral gavage using 10 mg/kg in 84/16 water/cyclodextrin (pH 4.6). Blood samples were collected and analyzed for drug content by HPLC/MS/MS (Dong C. et al., *J Pharmacol Exp Ther.* 2013 February; 344(2):436-46).

In vivo Blood pressure in SHR Rat: Male adult, 300-400 g, spontaneously hypertensive rats (3/group) were anesthetized with ketamine and a radio transmitter pressure and heart rate monitor (DSI model No. C50-PXT) was implanted into the abdomen of each rat. The pressure catheter was inserted into the descending aorta below the renal artery and secured to the abdominal musculature. ECG leads were placed intramuscularly, one at the right shoulder and the other at the lower left chest. The animals were individually housed and allowed to recover for at least 3 days. 6-(4-(aminomethyl)-2-chlorophenoxyl)benzo[c][1,2]oxaborol-1 (3H)-ol 600 mg/kg in vehicle, Losartan 10 mg/kg in vehicle, or vehicle (15% cyclodextrin in water), was administered to each rat by oral gavage. Blood pressure (BP) and heart rate (HR) data were recorded continuously for 48 hours (Data System International) Animals were fully conscious for all dosing and recording procedures. All dosing of animals occurred at approximately 0900 (based on a 0700 to 1900 light cycle). Blood pressure and heart rate was analyzed at 10-minute intervals and hourly means were plotted. Independent t-tests compared BP and HR values following treatment with 6-(4-(aminomethyl)-2-chlorophenoxyl) benzo[c][1,2]oxaborol-1(3H)-ol and Losartan with the vehicle control. This study and a similar study in normal rats were conducted by WuXi AppTec, Co., Suxhou, China, in accordance with AAALAC International and PRC, Ministry of Science and Technology Regulations.

Crystallization and structure of ROCK2 with 6-(4-(aminomethyl)-2-chlorophenoxyl)benzo[c][1,2]oxaborol-1(3H)-ol bound was performed by Proteros Biostructures (Martinsried, Germany). ROCK2, residues 27-417 (Genbank 3327051), was expressed in Sf9 insect cells and ROCK2 protein was purified by affinity and gel filtration, yielding homogenous protein with >95% purity, judged by coomassie stained SDS-PAGE. It was co-crystallized with 6-(4-(aminomethyl)-2-fluorophenoxy)benzo[c][1,2]oxaborol-1(3H)-ol, from solutions that were 9 mg/mL ROCK2 and 2 mM 6-(4-(aminomethyl)-2-fluorophenoxy)benzo[c][1,2]oxaborol-1(3H)-ol, the crystallization buffer contained 1.2M Na-citrate, 2 mM DTT, pH 6.0. The X-ray diffraction data were collected from the ROCK2-6-(4-(aminomethyl)-2-fluorophenoxy)benzo[c][1,2]oxaborol-1(3H)-ol crystals at the SWISS LIGHT SOURCE synchrotron facility (SLS, Villigen, Switzerland) using cryogenic conditions. The crystals belong to space group C2, and diffract to 2.79 Å. Data were processed using the programs XDS and SCALA. The crystals showed 35081 unique reflections with multiplicity of 2.5, completeness of 95.7%, $R_{sym}$ of 6.5%, $R_{meas}$ of 9.2%, $I/\_(I)$ of 6.5, and Mean(I)/sd of 7.9. Residues 391-393 were not defined in the structure and are omitted from the structure deposited in PDB as 4L6Q.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound which has a structure according to the following formula:

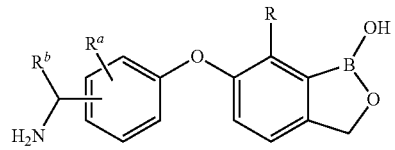

wherein
$R^a$ is halogen,
$R^b$ is H or unsubstituted $C_1$-$C_4$ alkyl,
when $R^b$ is unsubstituted $C_1$-$C_4$ alkyl, then R is H or halogen or unsubstituted $C_1$-$C_4$ alkyl,
when $R^b$ is H, then R is halogen or unsubstituted $C_1$-$C_4$ alkyl,
or a salt thereof.

2. The compound of claim 1, or a salt thereof, which has a structure according to the following formula:

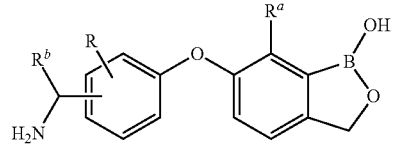

wherein
$R^a$ is halogen,
$R^b$ is unsubstituted $C_1$-$C_4$ alkyl,
R is H or halogen or unsubstituted $C_1$-$C_4$ alkyl.

3. The compound of claim 1, or a salt thereof, which has a structure which is:

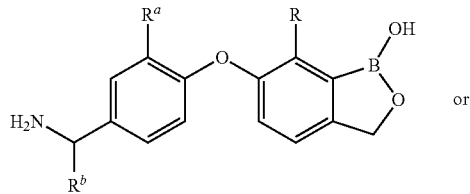

or

-continued

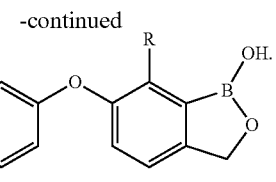

4. The compound of claim 1, or a salt thereof, in which R is F, Cl, methyl, ethyl, or isopropyl.

5. The compound of claim 1, or a salt thereof, in which $R^a$ is F or Cl.

6. The compound of claim 1, or a salt thereof, in which $R^b$ is methyl.

7. The compound of claim 1, or a salt thereof, in which $R^a$ is F or Cl, and $R^b$ is methyl.

8. The compound of claim 1, or a salt thereof, in which $R^a$ is Cl and $R^b$ is methyl.

9. The compound of claim 1, or a salt thereof, in which $R^a$ is F or Cl, $R^b$ is methyl, and R is methyl.

10. The compound of claim 1, or a salt thereof, in which $R^a$ is F or Cl, $R^b$ is methyl, and R is ethyl.

11. The compound of claim 1, or a salt thereof, in which $R^a$ is F or Cl, $R^b$ is methyl, and R is isopropyl.

12. A combination comprising:
(a) the compound of claim 1, or a salt thereof, and
(b) an additional therapeutic agent.

13. A pharmaceutical formulation comprising:
(a) the compound of claim 1, or a salt thereof, and
(b) a pharmaceutically acceptable excipient.

14. A method of inhibiting a kinase, comprising contacting said kinase with the compound of claim 1, or a salt thereof, thereby inhibiting said kinase whereby said kinase is ROCK1 or ROCK2.

15. A method of treating a disease, comprising administering to an animal in need of treatment a therapeutically effective amount of the compound of claim 1, or a salt thereof, thereby treating said disease, wherein the disease is selected from the group consisting of glaucoma, asthma, pulmonary hypertension, angina, heart failure, wound healing, and spinal cord injury.

16. The method of claim 15, wherein said disease is glaucoma.

17. The method of claim 15, wherein said disease is pulmonary hypertension.

18. The method of claim 15, wherein said animal is a human.

19. The method of claim 15, wherein said disease is glaucoma, and the glaucoma is selected from the group consisting of a primary glaucoma, a developmental glaucoma, a secondary glaucoma and absolute glaucoma.

* * * * *